United States Patent
Beaulieu et al.

(10) Patent No.: US 9,394,565 B2
(45) Date of Patent: Jul. 19, 2016

(54) ALLELE-SPECIFIC SEQUENCE VARIATION ANALYSIS

(75) Inventors: Martin Beaulieu, San Diego, CA (US); Dirk J. Van Den Boom, La Jolla, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 0 days.

(21) Appl. No.: 10/933,611

(22) Filed: Sep. 2, 2004

(65) Prior Publication Data

US 2005/0089904 A1    Apr. 28, 2005

Related U.S. Application Data

(60) Provisional application No. 60/500,489, filed on Sep. 5, 2003.

(51) Int. Cl.
*C12Q 1/68* (2006.01)

(52) U.S. Cl.
CPC ................... *C12Q 1/6827* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,762,823 A | 8/1988 | Watanabe et al. | |
| 4,826,360 A | 5/1989 | Iwasawa et al. | |
| 4,851,018 A | 7/1989 | Lazzari et al. | |
| 5,003,059 A | 3/1991 | Brennan | |
| 5,079,342 A | 1/1992 | Alizon et al. | |
| 5,118,937 A | 6/1992 | Hillenkamp et al. | |
| 5,122,457 A | 6/1992 | Reim et al. | |
| 5,173,418 A | 12/1992 | Molin et al. | |
| 5,210,412 A | 5/1993 | Levis et al. | |
| 5,252,478 A | 10/1993 | Margarit Y Ros et al. | |
| 5,256,775 A * | 10/1993 | Froehler ............... C07H 21/00 536/23.1 | |
| 5,264,563 A | 11/1993 | Huse | |
| 5,387,518 A | 2/1995 | Sawayanagi et al. | |
| 5,391,490 A | 2/1995 | Varshavsky et al. | |
| 5,427,927 A | 6/1995 | Meyer et al. | |
| 5,436,150 A | 7/1995 | Chandrasegaren | |
| 5,440,119 A | 8/1995 | Labowsky | |
| 5,453,247 A | 9/1995 | Beavis et al. | |
| 5,453,613 A | 9/1995 | Gray et al. | |
| 5,498,545 A | 3/1996 | Vestal | |
| 5,503,980 A | 4/1996 | Cantor | |
| 5,506,137 A | 4/1996 | Mathur | |
| 5,536,649 A | 7/1996 | Fraiser et al. | |
| 5,547,835 A | 8/1996 | Koster | |
| 5,578,443 A | 11/1996 | Santamaria et al. | |
| 5,580,733 A | 12/1996 | Levis et al. | |
| 5,604,098 A | 2/1997 | Mead et al. | |
| 5,605,798 A | 2/1997 | Koster | |
| 5,622,824 A | 4/1997 | Koster | |
| 5,631,134 A | 5/1997 | Cantor et al. | |
| 5,635,713 A | 6/1997 | Labowsky | |
| 5,646,020 A | 7/1997 | Swiggen et al. | |
| 5,686,656 A | 11/1997 | Amirav et al. | |
| 5,691,141 A | 11/1997 | Koster | |
| 5,700,672 A | 12/1997 | Mathur et al. | |
| 5,714,330 A | 2/1998 | Brenner et al. | |
| 5,753,439 A | 5/1998 | Smith et al. | |
| 5,777,324 A | 7/1998 | Hillenkamp | |
| 5,786,146 A | 7/1998 | Herman et al. | |
| 5,792,664 A | 8/1998 | Chait et al. | |
| 5,795,714 A | 8/1998 | Cantor et al. | |
| 5,807,522 A | 9/1998 | Brown et al. | |
| 5,830,712 A * | 11/1998 | Rampersad et al. ......... 435/91.1 | |
| 5,837,832 A | 11/1998 | Chee et al. | |
| 5,843,669 A | 12/1998 | Kaiser et al. | |
| 5,849,542 A | 12/1998 | Reeve | |
| 5,851,765 A | 12/1998 | Koster | |
| 5,853,979 A | 12/1998 | Green et al. | |
| 5,858,705 A | 1/1999 | Wei et al. | |
| 5,861,242 A | 1/1999 | Chee et al. | |
| 5,864,137 A | 1/1999 | Becker | |
| 5,869,240 A | 2/1999 | Patterson | |
| 5,869,242 A | 2/1999 | Kamb | |
| 5,871,911 A | 2/1999 | Dahlberg et al. | |
| 5,872,003 A | 2/1999 | Koster | |
| 5,874,283 A | 2/1999 | Harrington et al. | |
| 5,885,841 A | 3/1999 | Higgs, Jr. et al. | |
| 5,888,795 A | 3/1999 | Hamilton | |
| 5,900,481 A | 5/1999 | Lough et al. | |
| 5,928,870 A | 7/1999 | Lapidus et al. | |
| 5,928,906 A | 7/1999 | Koster et al. | |
| 5,932,451 A | 8/1999 | Wang et al. | |

(Continued)

FOREIGN PATENT DOCUMENTS

| | | | | |
|---|---|---|---|---|
| AU | 758454 B2 | 3/2003 | | |
| BE | WO00/66771 | * 11/2000 | ............... | C12Q 1/68 |
| BE | WO0066771 | * 11/2000 | ............... | C12Q 1/68 |
| EP | 0103677 | 3/1984 | | |
| EP | 0269520 | 1/1988 | | |
| EP | 0296781 | 6/1988 | | |
| EP | 0299652 | 7/1988 | | |
| EP | 0332435 | 9/1989 | | |
| EP | 0395481 | 4/1990 | | |
| EP | 0534858 | 3/1993 | | |

(Continued)

OTHER PUBLICATIONS

Jurinke et al. (1998, Rapid Comm. In Mass Spec. vol. 12, p. 50-52).*

(Continued)

*Primary Examiner* — Stephanie K Mummert

(74) *Attorney, Agent, or Firm* — Grant IP, Inc.

(57) ABSTRACT

Fragmentation-based methods and systems, particularly mass spectrometry based methods and systems, for the analysis of sequence variations including haplotypes are provided. Also provided are methods for obtaining a specific allele from a nucleic acid mixture, such as genomic DNA.

26 Claims, 5 Drawing Sheets

(56) References Cited

U.S. PATENT DOCUMENTS

| | | |
|---|---|---|
| 5,948,902 A | 9/1999 | Honkanen et al. |
| 5,952,176 A | 9/1999 | McCarthy et al. |
| 5,965,363 A | 10/1999 | Monforte et al. |
| 5,975,492 A | 11/1999 | Brenes |
| 5,976,806 A | 11/1999 | Mahejan et al. |
| 6,017,704 A | 1/2000 | Herman et al. |
| 6,022,688 A | 2/2000 | Jurinke et al. |
| 6,024,925 A | 2/2000 | Little et al. |
| 6,043,031 A | 3/2000 | Koster et al. |
| 6,051,378 A | 4/2000 | Monforte et al. |
| 6,054,276 A | 4/2000 | Macavicz |
| 6,059,724 A | 5/2000 | Campell et al. |
| 6,074,823 A | 6/2000 | Koster et al. |
| 6,090,549 A | 7/2000 | Mirzabekov et al. |
| 6,090,558 A | 7/2000 | Butler et al. |
| 6,090,606 A | 7/2000 | Kaiser et al. |
| 6,099,553 A | 8/2000 | Hart et al. |
| 6,104,028 A | 8/2000 | Hunter et al. |
| 6,107,039 A | 8/2000 | Hanna |
| 6,110,426 A | 8/2000 | Shalon et al. |
| 6,111,251 A | 8/2000 | Hillenkamp |
| 6,111,261 A | 8/2000 | Bolza-Schunemann et al. |
| 6,112,161 A | 8/2000 | Dryden |
| 6,113,436 A | 9/2000 | Kuwahara et al. |
| 6,133,436 A | 10/2000 | Koster et al. |
| 6,140,053 A | 10/2000 | Koster et al. |
| 6,146,854 A | 11/2000 | Koster et al. |
| 6,188,064 B1 | 2/2001 | Koster |
| 6,190,865 B1 | 2/2001 | Jendrisak et al. |
| 6,194,144 B1 | 2/2001 | Koster |
| 6,194,180 B1 | 2/2001 | Joyce |
| 6,197,498 B1 | 3/2001 | Koster |
| 6,200,756 B1 | 3/2001 | Herman et al. |
| 6,207,370 B1 | 3/2001 | Little et al. |
| 6,214,556 B1 | 4/2001 | Olek et al. |
| 6,221,605 B1 * | 4/2001 | Koster ............... 435/6 |
| 6,225,450 B1 | 5/2001 | Koster |
| 6,235,478 B1 | 5/2001 | Koster |
| 6,238,871 B1 | 5/2001 | Koster |
| 6,258,538 B1 | 7/2001 | Koster et al. |
| 6,265,167 B1 | 7/2001 | Carmichael et al. |
| 6,265,171 B1 | 7/2001 | Herman et al. |
| 6,265,716 B1 | 7/2001 | Hunter et al. |
| 6,268,131 B1 | 7/2001 | Kang et al. |
| 6,270,835 B1 | 8/2001 | Hunt et al. |
| 6,270,962 B1 | 8/2001 | Chamberlin et al. |
| 6,271,037 B1 | 8/2001 | Chait et al. |
| 6,277,573 B1 | 8/2001 | Koster et al. |
| 6,297,006 B1 | 10/2001 | Drmanac et al. |
| 6,300,076 B1 | 10/2001 | Koster |
| 6,309,833 B1 * | 10/2001 | Edman et al. ............ 435/6 |
| 6,322,970 B1 | 11/2001 | Little et al. |
| 6,326,174 B1 | 12/2001 | Joyce et al. |
| 6,331,427 B1 | 12/2001 | Robison |
| 6,383,775 B1 | 5/2002 | Duff et al. |
| 6,423,965 B1 | 7/2002 | Hashimoto et al. |
| 6,423,966 B2 | 7/2002 | Hillenkamp et al. |
| 6,428,955 B1 | 8/2002 | Koster et al. |
| 6,436,635 B1 | 8/2002 | Fu et al. |
| 6,440,705 B1 * | 8/2002 | Stanton et al. ............ 435/91.2 |
| 6,475,736 B1 | 11/2002 | Stanton, Jr. |
| 6,475,807 B1 | 11/2002 | Geysen et al. |
| 6,500,621 B2 * | 12/2002 | Koster ............... 435/6 |
| 6,522,477 B2 | 2/2003 | Anhalt |
| 6,537,746 B2 | 3/2003 | Arnold et al. |
| 6,558,902 B1 | 5/2003 | Hillenkamp |
| 6,566,055 B1 | 5/2003 | Monforte et al. |
| 6,569,385 B1 | 5/2003 | Little |
| 6,589,485 B2 | 7/2003 | Koster |
| 6,602,662 B1 | 8/2003 | Koster et al. |
| 6,884,586 B2 | 4/2005 | Van Ness |
| 6,994,960 B1 * | 2/2006 | Foote et al. ............ 435/6 |
| 6,994,969 B1 | 2/2006 | Zabeau et al. |
| 7,332,275 B2 | 2/2008 | Braun et al. |
| 7,608,394 B2 | 10/2009 | van den Boom et al. |
| 7,820,378 B2 | 10/2010 | van den Boom et al. |
| 2001/0008615 A1 | 7/2001 | Little et al. |
| 2002/0009394 A1 | 1/2002 | Koster et al. |
| 2002/0042112 A1 | 4/2002 | Koster et al. |
| 2002/0120127 A1 | 8/2002 | Church et al. |
| 2002/0155587 A1 | 10/2002 | Opalsky et al. |
| 2003/0013099 A1 | 1/2003 | Lasek et al. |
| 2003/0017483 A1 | 1/2003 | Ecker et al. |
| 2003/0027169 A1 | 2/2003 | Zhang et al. |
| 2003/0082600 A1 | 5/2003 | Olek et al. |
| 2003/0087235 A1 | 5/2003 | Dairkee et al. |
| 2003/0129589 A1 | 7/2003 | Koster et al. |
| 2003/0180748 A1 | 9/2003 | Braun et al. |
| 2003/0180749 A1 | 9/2003 | Braun et al. |
| 2003/0180779 A1 | 9/2003 | Lofton-Day et al. |
| 2003/0190644 A1 | 10/2003 | Braun et al. |
| 2004/0014101 A1 | 1/2004 | Liu et al. |
| 2004/0029258 A1 | 2/2004 | Heaney et al. |
| 2004/0102905 A1 | 5/2004 | Adorjan et al. |
| 2004/0253141 A1 | 12/2004 | Schembri et al. |
| 2005/0009053 A1 | 1/2005 | Boecker et al. |
| 2005/0019762 A1 | 1/2005 | Olek |
| 2005/0026183 A1 | 2/2005 | Fan et al. |
| 2005/0064406 A1 | 3/2005 | Zabarovsky |
| 2005/0064428 A1 | 3/2005 | Berlin |
| 2005/0069879 A1 | 3/2005 | Berlin |
| 2005/0089904 A1 | 4/2005 | Beaulieu et al. |
| 2005/0112590 A1 | 5/2005 | van den Boom et al. |
| 2005/0153316 A1 | 7/2005 | Jeddeloh |
| 2005/0153347 A1 | 7/2005 | Shapero |
| 2005/0164193 A1 | 7/2005 | Berlin |
| 2005/0164246 A1 | 7/2005 | Fan et al. |
| 2005/0272070 A1 | 12/2005 | Mathias et al. |
| 2006/0073501 A1 | 4/2006 | van den Boom et al. |
| 2006/0210992 A1 | 9/2006 | van den Boom et al. |
| 2006/0252061 A1 | 11/2006 | Zabeau et al. |

FOREIGN PATENT DOCUMENTS

| | | | |
|---|---|---|---|
| EP | 0596205 | 5/1994 | |
| EP | 0655501 | 5/1995 | |
| EP | 1197567 | 4/2002 | |
| EP | 1179589 | 12/2002 | |
| FR | 2749662 | 12/1997 | |
| GB | 2329475 | 8/1998 | |
| JP | 2003-245087 | * 9/2003 | ............... C12Q 1/68 |
| WO | WO 92/13969 | 8/1992 | |
| WO | WO 93/15407 | 8/1993 | |
| WO | WO 93/21592 | 10/1993 | |
| WO | WO 94/00562 | 1/1994 | |
| WO | WO 94/15219 | 7/1994 | |
| WO | WO 94/16101 | 7/1994 | |
| WO | WO 94/21663 | 9/1994 | |
| WO | WO 94/21822 | 9/1994 | |
| WO | WO 95/25281 | 9/1995 | |
| WO | WO 96/29431 | 9/1996 | |
| WO | WO 96/32504 | 10/1996 | |
| WO | WO 96/36732 | 11/1996 | |
| WO | WO 96/36986 | 11/1996 | |
| WO | WO 97/03210 | 1/1997 | |
| WO | WO 97/08306 | 3/1997 | |
| WO | WO 97/08308 | 3/1997 | |
| WO | WO 97/33000 | 9/1997 | |
| WO | WO 97/37041 | 10/1997 | |
| WO | WO 97/40462 | 10/1997 | |
| WO | WO 97/42348 | 11/1997 | |
| WO | WO 97/43617 | 11/1997 | |
| WO | WO 97/47766 | 12/1997 | |
| WO | WO 98/03684 | 1/1998 | |
| WO | WO 98/12355 | 3/1998 | |
| WO | WO 98/12734 | 3/1998 | |
| WO | WO 98/20019 | 5/1998 | |
| WO | WO 98/20020 | 5/1998 | |
| WO | WO 98/20166 | 5/1998 | |
| WO | WO 98/20453 | 5/1998 | |
| WO | WO 98/24935 | 6/1998 | |
| WO | WO 98/33808 | 8/1998 | |
| WO | WO 98/35609 | 8/1998 | |
| WO | WO 98/40520 | 9/1998 | |

(56) References Cited

FOREIGN PATENT DOCUMENTS

| | | |
|---|---|---|
| WO | WO 98/54571 | 12/1998 |
| WO | WO 99/05323 | 2/1999 |
| WO | WO 99/12040 | 3/1999 |
| WO | WO 99/28498 | 6/1999 |
| WO | WO 99/31278 | 6/1999 |
| WO | WO 00/18967 | 4/2000 |
| WO | WO 00/22130 | 4/2000 |
| WO | WO 00/31300 | 6/2000 |
| WO | WO 00/51053 | 8/2000 |
| WO | WO 00/56446 | 9/2000 |
| WO | WO 00/60361 | 10/2000 |
| WO | WO 00/06771 | 11/2000 |
| WO | WO 01/27857 | 4/2001 |
| WO | WO 01/55455 | 8/2001 |
| WO | WO 02/13122 | 2/2002 |
| WO | WO 02/25567 | 3/2002 |
| WO | WO 02/37398 | 5/2002 |
| WO | WO 02/086163 | 10/2002 |
| WO | WO 02/086794 | 10/2002 |
| WO | WO 02/101353 | 12/2002 |
| WO | WO 03/000926 | 1/2003 |
| WO | WO 03/002760 | 1/2003 |
| WO | WO 03/031649 | 4/2003 |
| WO | WO 03/038121 | 5/2003 |
| WO | WO 03/038726 | 5/2003 |
| WO | WO 03/044232 | 5/2003 |
| WO | WO 03/057909 | 7/2003 |
| WO | WO 03/078657 | 9/2003 |
| WO | WO 03/080863 | 10/2003 |
| WO | WO 2004/013284 | 2/2004 |
| WO | WO 2004/050839 | 6/2004 |
| WO | WO 2004/097369 | 11/2004 |
| WO | WO 2005/040399 | 5/2005 |
| WO | WO 2005/093095 | 10/2005 |
| WO | WO 2007/016668 | 2/2007 |

OTHER PUBLICATIONS

Bocker et al. (2003, Bioinformatics, 19(1), pp. i44-i53).*
Ding et al. (2003, PNAS, vol. 100, No. 12, p. 7449-7453).*
De Noronha et al. (1992, PCR Methods and Applications, 2(2), p. 131-6).*
Puskas et al. (Genome Research, 1995, vol. 5, p. 309-311).*
Schuette et al. (Journal of Pharmaceutical and Biomedical Analysis, 1995, vol. 13, p. 1195-1203).*
Chen et al. (Analytical Biochemistry, 1996, vol. 239, p. 61-69).*
Parsons et al. (Environmental and Molecular Mutagenesis, 1998, vol. 32, p. 200-211).*
Parsons et al. (Mutagenesis, 1998, vol. 13, No. 6, p. 581-588).*
Michalatos-Beloin et al. (Nucleic Acids Research, 1996, 24(23):4841-4843).*
Bocker (2003, Bioinformatics, 19(1), pp. i44-i53).*
Cline et al. (Nucleic Acids Research, 1996, 24(18):3546-3551).*
Holland et al. (PNAS, 1991, vol. 88, p. 7276-7280).*
Ellington et al. (Curr Protocols in Mol. Biol., 1998, 2.11.1-2.11.25).*
Knight et al. (Nature Genetics, 2003, vol. 33, p. 469-475).*
McKinzie et al. (Mutation Research, 2002, vol. 517, p. 209-220).*
Orou et al. (Human Mutation, 1995, vol. 6, 163-169).*
Aebersold and Mann, Nature, 422:198-207 (2003).
Amir et al., Nature Genet. 23:185-188 (1999).
Anderson, S., Nucleic Acids Res., 9(13): 3015-3027 (1981).
Anker, R. et al., Hum. Mol. Genet., 1(2): 137 (1992).
Amheim et al., Proc. Natl. Acad. Sci. USA, 82:6970-6974 (1985).
Arrand at al., J. Biol. Chem., 261.(20):9079-9082 (1986).
Bader and Hogue, BMC Bioinformatics. Jan. 13, 2003;4:2, Epub Jan. 13, 2003. http://www.biomedcentral.com/1471-2105/4/2.
Badger et al., Proteins: Structure, Function, and Genetics, 35(11):25-33 (1999).
Bains and Smith, J. Theoret. Biol., 135:303-307 (1988).
Banerjee, A. et al., Science, 263(5144): 227-230 (1994).
Barlow, D.P. and H. Leach, Trends Genet., 3: 167-171(1987).
Beaulieu et al., Am. J. Hum. Genet., 73(5):441—(2003).

Beck et al., Nucl. Acids Res., 17(13):5115-5123 (1989).
Beckmann, J.S. and J.L. Weber, 12: 627-631 (1992).
Berkenkamp, S. et al., Proc. Natl.Acad. Sci. U.S.A., 93(14): 7003-7007 (1996).
Bertina et al., Nature, 369:647 (1994).
Bessho et al., Nucl. Acids Res., 27(4):979-983 (1999).
Biemann, K., Methods in Enzyrnol., 193: 455-479(1990).
Bird, A., Genes and Development, 16(1): 6-21 (2002).
Bjelland at al., Nucl. Acids Res., 15(7):2787-2800 (1987).
Bleczinski at al., Rapid Communications in Mass Spectrometry, 12:1737-1743(1998).
Bocker, S., Bioinformatics 19(Suppl. 1):i44-i53 (2003).
Boecker, Lect. Notes Comp. Sci. 2818:476-487 (2003) (http://gi.cebitec.uni-bielefeld.de/people/boecker/dcwnload/Preprint_2003-04_Sequencing_SBoecker.pdf).
Boecker, Technical Report (http://gi.cebitec.uni-bielefeld.de/people/boecker/download/Preptint_003-07_WeightedSC_SBoecker.pdf).
Boguski, M.S. et al., J. Biol. Chem., 255(5): 2160-2163 (1980).
Braun et al., Clinical Chemistry, 43(7):1151-1158 (1997).
Braun et al., Genomics,46:18-23 (1997).
Breen, G., et al., BioTechniques, 28(3):464-470, (2000).
Bregman et al, J. Biol.Chem.. 266(11):7207-7213 (1991).
Browne, K. A., J.Am. Chem. Soc., 124(27): 7950-7962 (2002).
Buetow, et al., Proc. Natl. Acad. Sci. USA, (2001), 581-584, 98(2).
Burton at al., Proc. Natl. Acad. Sci. USA, 94:11067-11072 (1997).
Cai and Harrington., J. Chem. Inf. Comput. Sci 38: 1181-1170 (1998).
Caldwell and Joyce, PCR Methods and Applications 2:28-33 (1992).
Cannistraro, V.J. and D. Kennell, Eur. J. Biochem., 181(2): 363-370 (1989).
Carr et al., J. Biol. Chem., 287(19):13376-13382 (1992).
Carr et al., J. Biol.Chem., 266(22):14188-14192 (1991).
Caskey, C. T. et al., Science 256(5058): 784-789 (1992).
Cavalli-Sforza, L.I.,Trends in Genetics 14(2): 60-65 (1998).
Chait, B.T. and S.B.H. Kent, Science, 257(5078): 1885-1894(1992).
Chakrabarti, L. et al., Nature, 328(6130): 543-547 (1987).
Chechetkin et al., Biomol. Struct. Dyn., 18(1):83-101 (2000).
Chiu et al, Clin. Chem., 45:1578 (1999).
Chiu et al., Nucl. Acids. Res., 28(8):e31 (2000).
Chung, M.H. et al., Mutat. Res., 254(1): 1-12, (1991).
Clausen et al., J. Clinical Investigation, 98(5):1195-1209 (1996).
Clegg or al., Proc. Natl. Acad. Sci. USA, 85:3703-3707(1988).
Cleveland, D.W. et al., J. Biol. Chem., 252(3): 1102-1106 (1977).
Coghlan at al., Science, 267:108-111 (1995).
Cohen et al., Advanced Chromatography, 36:127?162 11996).
Colledge et al., Trends in Cell Biology, 8:216-221(1999).
Collins et al., Genome Research, 8:1229-1231 (1998).
Corder et al., Science, 261:921-923 (1993).
Costello et al., Nature Genet., 24:132-138 (2000).
Database WPI, Derwent publication #007515331.
Database WPI, Derwent publication # 011635345.
Dausset, J. et al., Genomics, 6(3): 575-577(1990).
Delagrave et al., Protein Engineering, 6:327-331 (1993).
Ding and Cantor, Proc. Natl. Acad. Sci. USA, 100(13):7449-7453 (2003).
Dittmar, M., Anthropol Anz. 53(4): 289-315 (1995).
Dodgson et al., Poultry Science 76: 1108-1114 (1997).
Donis-Keller, H. et al., Nucleic Acids Res., 4(8): 2527-2537 (1977).
Donis-Keller, H., Nucleic Acids Res., 8(14): 3133-3142 (1980).
Downes, Kate, et al., BioTechniques, (2004), 840-845, 36(5).
Dunham, I. et al., Nature 402(6761): 489-495 (1999).
Edwards, M.C. et al.Nucleic Acids Res., 19(17): 4791 (1991).
Eftedal et al., Nucl. Acids Res., 21191:2095-2101 (1993).
Eggertsen et al., Clinical Chemistry 30(10):2125-2129 (1993).
Ehrlich, S.D. et al., Biochemistry 10(11):2000-2009 (1971).
Eitan et al., Nucleic Acids Res. 30(12):E62.1-E62.8 (2002).
Elso et al., Genome Res. 12(9):1428-1433 (2002).
Faux et al., Trends Biochem., 21:312-315 (1996).
Fei and Smith., Rapid Commun. Mass. Spectrom., 14(11):950-959 (2000).
Foster et al., Genome Research, 8:755-757 (1998).
Fu et al., Genetic Analysis:Biomolecular Engineering, 12:137-142 (1996).

(56) References Cited

OTHER PUBLICATIONS

Fu et al., Nature Biotechnol., 16:381-384 (1998).
Fu et al., Proc. Natl. Acad. Sci. USA, 92:10162-10166 (1995).
Fu et al., Nucl. Acids Res. 25(3):677-679 (1997).
Gabbita et al., J Neurochemistry, 73(4):1660-1666 (1999).
Gardiner-Gordon et al., J. Mol. Biol. 196:261-281 (1987).
German, J. and E. Passarge, Clin. Genet., 35: 57-69 (1989).
Germer et al, Genome Research, 10:258-266 (2000).
Germino, J. and D. Bastis, Proc. Natl. Acad. Sci. U.S.A., 81(15):4692-(1984).
Glantz et al., J. Biol. Chem., 2681171:12796-12804 (1993).
Gogos, J.A. et al., Nucleic Acids Res., 18(23): 6807-6817 (1990).
Goldmacher et al, Bioconj. Chem., 3:104-107 (1992).
Goldman and Youvan, Biotechnology 10:1557-1561 (1992).
Graber et al., Genetic Analysis: Biomolecular Engineering, 14:215-219 (1999).
Griffin et al., Nature Biotechnology, 15:1368-1372 (1997).
Grunau et al., Nucl. Acid Res., 29:C65 (2001).
Guatelli et al, Proc. Natl. Acad. Sci. USA, 87:1874-1878 (1990).
Gupta, R.C. and K. Randerath, Nucleic Acids Res., 4(6):1957-1978 (1977).
Gust, I.D. et al., Intervirology, 20: 1-7 (1983).
Gut, I. G. and S. Beck, Nucleic Acids Res., 23(8): 1367-1373 (1995).
Guyader, M. et al., Nature, 326(6114): 662-669 (1987).
Haff and Smirnov, Genome Research, 7:378-388 (1997).
Haffey, M. L. et al., DNA,6(6): 565-571 (1987).
Hahner, S. et al., Nucleic Acids Res., 25(10): 1957-1964 (1997).
Hanish, J. and M. McClelland, Gene, Gene. Anal. Tech., 5: 105-107 (1988).
Harrington, J.J. and M.R. Lieber, Genes and Develop., 8(11): 1344-1355 (1994).
Hartmer et al., Nucleic Acids Res., 31(9):E47.1-E47.10 (2003).
Hausken et al., J. Biol. Chem., 271(46):29016-29022 (1996).
Hazum et al., in Pept., Proc. Eur. Pept. Symp., 16th, Brunfeldt, K., (Ed.), pp. 105-110 (1981).
Herman et al., Proc. Natl. Acad. Sci. 93:9821-26 (1996).
Hey, J., Trends in Genetics 14(8): 303-305 (1998) (with reply by L. Cavalli-Worn).
Higgins et al., BioTechniques, 23(4):710-714 (1997).
Higgins et al., Methods in Enzymology, 68:50-71(1979).
Higley et al., Mutation Research, DNA Repair, 294;109-116 (1993).
Hillenkamp, F. and M. Karas, Anal. Chem., 63(24): 1193A-1202A (1991).
Hinton et al., Laboratory Automation & Information Management, vol. 21 No. 2103, pp. 223-227, Dec. 1, 1993.
Hoogendoom, et al., Hum Genet. (2000) 107:488-493.
Hsu, I-C. et al., Carcinogenesis, 15(8): 1657-1662 (1994).
Huang et al., Journal of Biological Chemistry, 272(12):8057-8064 (1997).
Huang et al., Proc. Natl. Acad. Sci. USA, 94:11104-11189 (1997).
Huang, Z.-H. et al., Anal. Biochem., 268(2):305-317 (1999).
Hubbard et al., Trends Biochem. Sci., 18:172-177 (1993).
Ikemoto, S., Nippon Hoigaku Zasshi 49(6): 419-431 (1995).
Jahnen et al., Biochem. Biophys. Res. Commun.,166(1): 139-145 (1990).
Jahnsen et al , J.Biol. Chem., 261(26):12352-12361 (1986).
Jeffreys et al., Nature, 314:67-73 (1985).
Jiang-Baucom et al., Analytical Chemistry, 61:4894-4898 (1997}.
Johnson, R. S. et al., Intl. J. Mass Spectrom. Ion Processes,86: 137-154 (1988).
Ju, L.-Y., et al., Electrophoresis 12(4):270-273 (1991).
Jurinke at el., Genetic Analysis: Biomolecular Engineering. 13:67-71(1996).
Jurinke et al , Genetic Analysis: Biomolecular Engineering, 14:97-102 (1998).
Jurinke et al., Anal. Biochem., 237:174-181 (1996).
Jurinke et al., Anal. Chem., 69:904-910 (1997).
Jurinke, C. et al., Methods Mol. Biol., 187: 179-192 (2002).
Jurinke, C. et al., Adv. Biochem. Eng. Biotechnol., 77: 57-74 (2002).
Kario et al., Thromb. Haemost., 73:617-22 (1995).
Klauck et al., Science, 271:1589-1592 (1998).
Koster et al., Nucl. Acids Res., Symposium Series No. 24 (1991) 318-321.
Koster et al.,Nature Biotechnology, 14:1123-1128 (1996).
Krebs et al., Nucleic Acids Res., 31(7):E37.1-E37.8 (2003).
Kruglyak and Nickerson., Nature Genetics, 27-234-236 (2001).
Kuchino, Y. and S. Nishimura, 180: 154-163 (1989).
Kwoh et al., Proc. Natl. Acad. Sci. USA,:86:1173-1177 (1989).
Kwok et al., Nucl. Acids Res.,18(4): 999-1005 (1990).
Lai, E. et al., Genomics, 54(1): 31-38 (1998).
Laken et al., Nature Biotechnology, 16:1352-1356 (1998).
Laken et al., Nature Genetics, 17:79-83 (1995).
Lam et al., Diabetologia, 41:760-766 (1998).
Landegren et al., Genome Res., 8:769-776 (1998).
Lasko et al, Mutation Research, 236:277-287 (1990).
Le hellard, et al., Nucleic Acids Research, (2002) 1-10, 30(15).
Lee et al., Proc. Natl. Acad. Sci. USA, 80:3608-3612 (1983).
Lehman, I.R.,Science, 186:790-797(1974).
Li et al., Anal. Chem., 68(13):2090-2096 (1996).
Li et al., Cell, 69:915-926 (1992).
Li et al., Nucl. Acids Res., 22(4):632-636 (1994).
Li, J., Abstract—Eleventh IEEE Symposium on Computer-Based Medical Systems, pp. 252-255 (1998).
Lindahi et al, Annu. Rev. Biochem., 61:251-281 (1992).
Litt, M. and J.A. Luty, Nucleic Acids Res., 18(14): 4301 (1990).
Litt, M. et al., NucleicAcids Res., 18(19): 5921 (1990).
Little et al., International Journal of Mass Spectrometry and Ion Processes,169-170:323-330 (1997).
Little et al., Anal. Chem., 69:4540-4546 (1997).
Little et al., Eur. J. Clin. Chem. Clin. Biochem.,35(7),:545-548 (1997).
Little et al., J. Mol. Med., 75:745-750 (1997).
Little et al., Nature Medicine, 3:1413-1416 (1997).
Paterson, A.H., Genome Research 5(4): 321-333 (1995).
Pena et al., J. Mol. Med. 73: 555-564 (1995).
Perlman, P.S. and R.A. Butow, "Mobile Introns and Intron-Encoded Proteins",Science, 246(4934): 1106-1109 (1989).
Pevzner, J. Biomol. Struct. Dyn., 7:63-73 (1989).
Pevzner, PNAS USA, 98(17):9748-9753 (2001).
Ploos et al., "Tetranucleotide repeat polymorphism in the vWF gene", NucleicAcids Res., 18(16): 4957 (1990).
Podhajska et al., Gene, 40:175-182 (1985).
Polettini et al., Journal of Chromatography B 713; 265-279 (1998).
Polymeropoulos et al., "Tetranucleotide repeat polymorphism at the humanaromatase cytochrome P-450 gene (CYP19)", Nucl. Acids Res., 19(1): 195 (1991).
Polymeropoulos, M.H. et al., "Tetranucleotide repeat polymorphism at the humanc-fes/fps proto-oncogene (FES)", Nucleic Acids Res., 19(14): 4018 (1991).
Polymeropoulos, M.H. et al., Nucl. Acids Res., 19(15): 4306 (1991).
Polymeropoulos, M.H. et al., , Nucl. Acids Res., 18(24): 7468 (1990).
Ratner, L. et al., "Complete nucleotide sequence of the AIDS virus, HTLV-III",Nature, 313: 227-284 (1985).
Red Tape; It's in You to Give: Ottawa Citizen Saturday Final Edition Oct. 5, 2002.
Reymer et al-, Nature Genetics, 10:28-34 (1995).
Risch and Ten., Genome Research,(1998), 8:1273-1288.
Robertson et al., Nature Rev. Genet. 1:11-19 (2000).
Rodi et al., Biotechniques 32(Suppl):S62-S69 (2002).
Rojo, M.A. et al., "Cusativin, a new cytidine-specific ribonuclease accumulated inseeds of *Cucumis sativus* L"; Planta, 194: 328-338 (1994).
Ross et al., Analytical Chemistry 69:4197-4202 (1997).
Ross et al., Analytical Chemistry 69:3966-3972 (1997).
Ross et al., Nature Biotechnology 16:1347-1351 (1998).
Ross, et al., BioTechniques, (2000) 29(3):620-629.
Ruppert et al.,Anal. Biochem., 230:130-134 (1995).
Samson et al., Nature, 382:722-725 (1996).
Santoro, S. W. and G. F. Joyce, "A general purpose RNA-cleaving DNA enzyme",Prot. Natl. Acad. Sci. U.S.A., 94(9): 4262-4266 (1997).
Saparbaev et al., Nucl. Acids Res., 23(18):3750-3755 (1995).

(56) References Cited

OTHER PUBLICATIONS

Sargent, T.D. et al., "Isolation of Differentially Expressed Genes", MethodsEnzymol., 152: 423-432 (1987).
Saris, C.J.M. et al., "Hydrcocylamine Cleavage of Proteins in Polyacrylamide Gels",Anal. Biochem., 132(1): 54-67 (1983).
Sarkar et al. , Moire Inst. Oswaldo Cruz, 93(51:693-694 (1998).
Sarkar et al., Analytical Biochemistry 186:64-68 (1990).
Sarkar et al., Biotechniques 10(4):436-440 (1991).
Sasaki, et al., Am. J. Hum, Genet. (2001) 68:214-218.
Schachter et al., Nature Genetics, 6:29-32 (1994).
Scott et al., J. Biol. Chem., 265(35):21561-21566 (1990).
Scott, J., 50:123-145(1991).
Seela, F. and A. Kehne, "Palindromic octa- and dodecanucleotides containing 2'-deoxytubercidin: synthesis, hairpin formation, and recognition by the endodeoxyribonuclease EcoRI", Biochemistry, 26(8): 2232-2238 (1987).
Senko et al., J. Am. Soc. Mass Spectrom., 6:52-56 (1995).
Senter et al., Photochem. Photobiol., 42:231-237.(1985).
Sequenom, Application Notes from company website: "SNP Discovery Using theMassARRAY System", http://www. sequenom.com/Assets/pdfs/appnotes/SNP __Discovery_Application_Note.pdf (accessed on Jun. 29, 2004).
Shchepinov et al., "Matrix-induced fragmentation of P3'-N5'-phosphoroamidatecontaining DNA: high-throughput MALDI-TOF analysis of genomic sequence polymorphisms", Nucleic Acids Res. 29(18):3864-3872 (2001).
Shriner et al., Am. J. Hum. Genet., 60:957-964 (1997).
Siegert et al., Anal. Biochem., 24 :55-65 (1996).
Simoncsits et al., "New rapid gel sequencing method for RNA", Nature, 269: 833-836 (1977).
Siuzdak, G., "The emergence of mass spectrometry in biochemical research", Proc. Natl. Acad. Sci, U.S.A., 91(24): 11290-11297 (1994).
Smith, D. B. and K. S. Johnson, "Single-step purification of polypeptides expressed in *Escherichia coli* as fusions with glutathione S-transferase", Gene, 67: 31-40 (1988).
Smith, L.M., Nature Biotechnology, 14:1084-1085 (1996).
Sommer et al., Biotechniques, 12(1):82-87 (1992).
SpectroCHIP BioArray , Sequenom Product Advertisement.
Springer, B. et al., "Two-laboratory collaborative study on identification of mycobacteria: molecular versus phenotypic methods", J. Clin. Microbiol., 34(2):296-303 (1996).
Srinivasan et al. , Rapid Communications in Mass Spectrometry, 11:1144-1150 (1997).
Stanssens et al., Genomic Res., 14:126-133 (2004).
Stevens, A., "Pyrimidine-specific cleavage by an endoribonuclease of *Saccharomyces cerevisiae*", J. Bacteriol., 1641): 57-62 (1985).
Stults, J. T. et al., "Simplification of high-energy collision spectra of peptides byamino-terminal derivatization", Anal. Chem., 65(13): 1703-1708 (1993).
Sugisaki et al., Gene, 16:73-78 (1981).
Szybalski et al., Gene, 100:13-26 (1991).
Takio et al., Proc. Natl. Acad. Sci. USA, 79:2644-8(1982).
Tammen et al.,, J. Cromatogr. A. 852:285-295.
Tang et al., Nucl. Acids Res., 23(16):3126-3131 (1995).
Tang et al., Int. J. Mass Spectrometry, 226(1):37-54 (2003).
Little, D. P. et al., Nat. Med., 3(12): 1413-1416 (1997).
Lizardi et al., BioTechnology, 6:1197-1202 (1988).
Lu, A.-L. and I.-C. Hsu, "Detection of Single DNA Base Mutations with MismatchRepair Enzymes", Genomics, 14(1): 249-255 (1992).
Luty, J.A. and M. Litt, "Dinucleotide repeat polymorphism at the D 14S45 locus",Nucleic Acids Res., 19(15): 4308 (1991).
Luty, J.A. et al., "Five Polymorphic Microsatellite VNTRs on the Human XChromosome", Am. J. Hum. Genet., 46: 776-783 (1990).
Marotta, C.A. at al., "Preferred sites of digestion of a ribonuclease fromEnterobacter species in the sequence analysis of Bacillus stearothermophilus 5Sribonucleic acid", Biochemistry, 12(15): 2901-2904 (1973).
Maxam, A.M. and W. Gilbert, "A new method for sequencing DNA", Proc. Natl.Acad. Sci. U.S.A., 74(2): 560-564(1977).

McClelland, M. et al., "A single buffer for all restriction endonucleases", NucleicAcid Res., 16(1): 364 (1988).
McKinnon, P.J., Hum. Genet., 75(3): 197-208 (1987).
McKinzie et al., Mutation Research, 517(1-2):209-220 (2002).
McLafferty, F.W., ,Acc. Chem. Res., 27(11): 379-386 (1994).
Miki and Eddy., J. Biol. Chem., 273(51):34384-34390.
Miki et al., J. Biol. Chem.274(41):29057-29062 (1999).
Minshull and Stemmer Curr. Opin. Chem. Biol., 3(3):284-290 (1999).
Mochly-Rosen, D.,Science, 268:247-251 (1995).
Morris et al., J. Infect. Dis., 171: 954-960 (1995).
Moskovitz et al., Proc. Natl. Acad. Sci. USA, 95:14071-14075 (1998).
Muller et al., Human Molecular Genetics, 9(5):757-763, 2000.
Murante, R. S. et al., J. Biol. Chem., 269(2): 1191-1196 (1994).
Nagai, K. and H. C.Thogersen, Nature, 309: 810-812(1984).
Nagamura et al, Plant Molecular Biology 35: 79-87 (1997).
Nakamura, Y. et al., Science, 235: 1616-1622 (1987).
Nelson et al. , Journal of Magnetic Resonance 84:95-109 (1989).
Nikodem, V. and J.R. Fresco, "Protein Fingerprinting by SDS-Gel Electrophoresisafter Partial Fragmentation with CNBr", Anal. Biochem., 97(21 382-386 (1979).
Nilges et al., J. Mol. Biol., 269:408-422 (1997).
Nishimura, D.Y. and J.C. Murray, "A tetranucleotide repeat for the F13B locus",Nucleic Acids Res., 20(5): 1167 (1992).
Nordhoff, E. et al., "Ion stability of nucleic acids in infrared matrix-assisted laserdesorption/ionization mass spectrometry"; Nucleic Acids Res., 21(15): 3347-3357(1993).
Nucleases 2nd ed., Linn, S.M. at al., (Eds.), Cold Spring Harbor Laboratory Press (1993).
Okano et al., Cell, 99: 247-257 (1999).
Olek et al., Nucl. Acid Res., 24:5064-5066 (1996).
Tang et al., Proc. Natl. Acad. Sci. USA, 96(18):10016-10020 (1999).
Taranenko et al, Genetic Analysis: Biomolecular Engineering. 13:87-94 (1996).
Tautz, D., "Hyperyariability of simple sequences as a general source forpolymorphic DNA markers . . . ", Nucleic Acids Res., 17(16): 6463-6471 (1989).
The International SNP Map Working Group, "A Map of human genome sequencevariation containing 1.42 million single nucleotide polymorphisms", Nature,409(6822): 928-933 (2001).
Thompson, Laboratory Automation and Information Management, 31:173-193 (1996).
Tost et al., Nucl. Acid Res., 31:C50 (2003).
van den Boom et al., Anal. .Biochem., 256:127-129 (1998).
van den Boom et al., Int. J. Mass Spectrom., 238(2):173-188 (2004).
van den Boom et al., J. Biochem. Biophys. Methods, 35:69-79 (1997).
Vanfleteren, J.R. et al., "Peptide Mapping and Microsequencing of ProteinsSeparated by SDS-Page After Limited In Situ Acid Hydrolysis", BioTechniques,12(4): 550-557 (1992).
Vath, J. E. et al., "Method for the derivatization of organic compounds at the sub?nanomole level with reagent vapor", Fresenius' Zeitschrfl fur analytische Chemie,331: 248-252 (1988).
Vaughan et al., Genetic Analysis: Biomolecular Engineering, 14:169-175.(1999).
von Wintzingerode, F. et al., "Base-specific fragmentation of amplified 16S rRNAgenes analyzed by mass spectrometry: A tool for rapid bacterial identification",Proc. Natl. Acad. Sci. U.S.A., 99(10): 7039-7044 (2002).
von Wintzingerode, F. et al., "Phylogenetic Analysis of an Anaerobic,Trichlorobenzene-Transforming Microbial Consortium", Appl. Environ. Mcrobiol.,65(1): 283-286 (1999).
Wada, J. Mass Spectrometry, 33:187-192 (1998).
Waga et al., J. Biol. Chem., 269(14)10923-10934 (1994).
Wagner, D. S. et al., "Derivatization of Peptides to Enhance Ionization Effiencyand Control Fragmentation During Analysis by Fast Atom Bombardment TandemMass Spectrometry", Biol. Mass Spectrom., 20(7): 419-425 (1991).
Wain-Hobson, S. et al., "Nucleotide sequence of the AIDS virus, LAV", Cell, 40:9-17 (1985).
Wang et al, J. Mol. Spectrosc., 194(20):256-268 (1999).
Wang et al., Science, 280:1077-1082 (1998).

(56) References Cited

OTHER PUBLICATIONS

Weber, J.L and P.E. May, "Abundant class of human DNA polymorphisms whichcan be typed using the polymerase chain reaction", Am. J. Hum. Genet., 44: 388?396 (1989).
Weiler et al., Nucleic Acids Res., 25:2792-2799 (1997).
Weissenbach et al., Nature, 359(6358):794-801 (1992).
Wilson et al., Annu. Rev. Genet., 25:585-627(1991).
Yasuda et al., Japanese Journal of Legal Medicine 51: 407-416 (1997).
Yates, J. Mass Spec., 33:1-19 (1998).
Yen et al, Makromol. Chem., 190:69-82 (1989).
Yule, A., "Amplification-Based Diagnosis Target TB", Bio/Technology, 12: 1335?1337 (1994).
Zaia, J. and K. Biemann, "Comparison of Charged Derivatives for High EnergyCollision-Induced Dissociation Tandem Mass Spectrometry", J. Am. Soc. MassSpectrom., 6(5): 428-436 (1995).
Zaia, J., in: Protein and Peptide Analysis by Mass Spectrometry, J. R. Chapman (ed.), pp. 29-41, Humana Press, Totowa, N.J., (1996).
Zhou, et al., Nucl. Acids Res., (2001), 29(19 e93):1-11.
Zuliani, G. and H.H. Hobbs, "Tetranucleotide repeat polymorphism in the LPLgene", Nucleic Acids Res., 18(16): 4958 (1990).
Akiyama, Y. et al., "Cell-Type-Specific Repression of the Maspin Gene is. Disrupted Frequently by Demethylation at the . . . " Amer. J. of Pathology, 2003, 1911-1919,163, Japan.
Baylin and Bestor, "Altered methylation pattersn in cancer cell genomes: cause or consequence?" Cancer Cell. May 2002;1(4):299-305.
Blazewicz et al., "On some properties on DNA graphics," Discrete Applied Mathematics, vol. 98, 1999, pp. 1-19.
Blazewicz et al., "On the recognition of de Bruijn graphs and their induced subgraphs," Discrete Applied Mathematics, vol. 245, 81-92 Feb. 28, 2002.
Buck et al., "Design Strategies and Performance of Custom DNA Sequencing Primers" BioTechniques. Sep. 1999. 27:528-536.
Chen et al., "Detectionin fecal DNA or colon cancer specific methylation of the nonexpressed vimentin gene," J Natl Cancer Inst., Aug. 3, 2005;97(15):1124-1132.
Costello, J. et al., "Methylation matters: a new spin on maspin" Nature Genetics, 2002, 123-124,31 USA.
Dahl, et al., "DNA methylation analysis techniques," Biogerontology, 2003, vol. 4 pp. 233-250; especially pp. 242-245.
Downes, Kate, et al., SNP allele frequency estimation in DNA pool and variance components analysis, BioTechniques, (2004), 840-846, 36(6), The Wellcome Trust Sanger Institute.
Egland, K. et al., "Characterization of Overlapping XAGE-1 Transcripts Encoding a Cancer Testis Antigen Expressed in . . . " Molecular Cancer Therapeutics, 2002,441-450, USA.
Futscher, B. et al., "Aberrant Methylation of the Maspin Promoter is an Early Event in Human Breast Cancer" Neoplasia, 2004,380-389, 6, USA.
Futscher, B., et al., "Role for DNA methylation in the control of cell type-specific maspin expression", Nature Genetics, 2002, 175-179, 31, USA.
Genbank Accession AC005730.
Genbank Accession AF021833.
Genbank Accession AF096289.
Genbank Accession AJ242973.
Genbank Accession AW195104.
Genbank Accession AW874187.
Genbank Accession NM007202.
Genbank Accession No. AF037439, Chatterjee et al. Dec. 1997.
Genbank Accession X86173.
Germer, Saren, et al, High-throughput SNP Allele-Frequency Determination in Pooled DNA Samples by Kinetic PCR, Methods, Genome Research, (2000). 258-266, 10, Cold Spring Harbor Laboratory Press.
Heighway, J. et al., "Expression profiling of primary non-small cell lung cancer for target identification", Oncogene, 2002, 7749-7763,21, UK.
Herman et al., "Methylation-specific PCR: A Novel PCR Assay for Methylation Status of CpG Islands," PNAS 93:9821-9826 (1996).
Heym, B. et al., Lancet, 344(8918): 293-298 (1994).
Hurtubise, A. et al., "Evaluation of antineoplastic action of 5-aza-2rdeoxycytidine . . . (Dacogen) and docetaxel (Taxotere) on . . . " Anti-Cancer Drugs, 2004. 161-1 67,15, Canada.
Instrumentation; "Genesis 200/8" (200 cm with including an 8-tip arm) liquid handling systems; Tecan AG of Switzerland ("Tecan"), Tecan Products for Diagnostics and Life Science, located at http://www.tecan.ch/index.htm.
Instrumentation; "Model CRS A 255" robot"Digital Servo Gripper" "Plate Cube" system."lid parking station" "shaker" Robocon Labor- und Industrieroboter Ges.m.b.H of Austria ("Robocon").
Instrumentation; "Multimek 96" automated pipettor; Beckman Coulter, Inc. located at http://www.coulter.com, Sep. 8, 1999.
Instrumentation; "Nano-Plotter" from GeSiM, Germany, located at http:/www.gesim.de/np-intro.htm
Instrumentation; Bar code systems, including one and two dimensional bar codes, readable and readable/writable codes and systems; Datalogic S.p.A. of Italy ("Datalogic") located at http://www.datalogic.com.
Instrumentation; DYNABEADS, streptavidin-coated magnetic beads; from Dynal, Inc. Great Neck, NY and Oslo Norway.
Instrumentation;"MJ Microseal" plate sealer; Thermal Cycler Accessories: Sealing Options, Sealing Products, MJ Research, located at http://www.mjresearch.com/html/consumables/ealing/sealing_products.html.
International Search Report for International Application No. PCT/US00/08111, Date of Mailing Nov. 13, 2000.
International Search Report for International Application No. PCT/US005/32441 Oct. 2, 2006.
Jurinke et al., "Detection of RET proto-oncogene codon 634 mutations using mass spectrometry", J. Mol. Med., 75:745-750, (1997).
Kim, S. et al., "Maspin Expression is Transactivated by P63 and is Critical for the Modulation of Lung Cancer Progression" Cancer Research, 2004, 6900-6905, 64, Korea.
Kirk, et al., "Single Mucleotide polymorphism seeking long term association with complex disease," Nucleic Acids Res. 2002, vol. 30, No. 5, pp. 3295-3311.
Lindahl et al., Annu. Rev Biochem., 61:251-281 (1992).
Ling, X. et al., "Proteomics-Based Identification of Maspin Differential Expression in Bronchial Epithelia Immortalized . . . " Chinese J. of Cancer, 2003,463-466, 22, China.
Liu, X. et al., "XAGE-1, A New Gene That is Frequently Expressed in Eqing's Sarcoma" Cancer Research, 2000, 4752-4755, 60, USA.
Maass, N. et at., "Decline in the expression of the serine proteinase inhibitor maspin is associated with tumour progression . . . " J. of Pathology, 2001, 321-326,195, Germany.
Maass, N., et al., "Hyiperrnethylation and histone deacetylation lead to silencing of the maspin gene in human breast cancer . . . " BBRC, 2002, 125-128,297, USA.
Moon, C. et al. "Aquaporin Expression in Human Lymphocytes and Dentritic Cells" American Journal of Hematotogy, 2004 128,-133, 75, USA.
Moon, C. et al., "Involvement of aquaporins in colorectal carcinogenesis" Oncogene, 2003,6699-6703,22, USA.
Murakami, J. et al., "Effects of dernethylating agent 5aza-2'deoxycytidine and histone deacetylase inhibitor FR901228 on rnaspin . . . " Oral Oncology 2004,597-603,40, Japan.
NCBI GenBank Accession No. NM_002639.
Ogasawara, S. et al., "Disruption of cell-type-specific methylation at the Maspin gene promoter is frequently involved in . . . " Oncogene, 2004, 11 17-1 124, 23, Japan.
Oshio, K. et al., "Aquaporin-1 expression in human glial tumors suggests a potential novel therapeutic target for tumor-associated . . . " Acta Neurochir, 2003,494-502, 86, USA.
Saadoun, S. et al., "Increased aquaporin 1 water channel expression in human brain tumours", British J. of Cancer, 2002, 621-623,87, UK.
Sakai et al., American Journal of Human Genetic, 1991 vol. 48, pp. 880-888.

(56) References Cited

OTHER PUBLICATIONS

Sato, N. et al. "Identification of rnaspin and S100P as novel hypomethylation targets in pancreatic cancer using global gene expression profiling", 2004, 1531-1538,23, USA.
Sequenom Advances the Industrial Genomics Revolution with the Launch of its DNA MassArray Automated Process Line, Press Release: Sep. 28, 1998, http://www.sequenom.com/pressrelease.htm.
Sequenom and Gemini Identify Genes Linked to Cardiovascular Disease, Press Release: Nov. 28, 2000, http://www/sequenom.com/ir/ir_prs.asp.
Sequenom Announces Publication of Results From Large-Scale SNP Study With the National Cancer Institute, Press Release: Jan. 16, 2001, http://www/sequenom.com/ir/ir_prs.asp.
Sequenom Completes Design of More Than 400,000 SNP Assays; Mass Extendtm Assay Portfolio Covers Majority of SNPs in the Public Domain, Press Release; Oct. 10, 2000, http://www/sequenom.com/ir/ir_prs.asp.
Sequenom: Technologies and Tools, located at http://www.sequenom-san.com/tech/tools.html, dated Aug. 29, 1999.
Sheng et al., "Tagged probe interval graphs," Journal of Combinatorial Optimization. 2001 vol. 5, pp. 133-142.
Sigaloiti, L. et al., "Cancer testis antigens expression in mesotheliomasole of DNA methylation . . . " British J. of Cancer, 2002, 979-982, 86, UK.
Smith, S. et al., "Maspin-the most commonly-expressed gene of the 18q21.3 serpin cluster in lung cancer . . . " Oncogene, 2003, 8677-8687,22, UK.
Stomakhin et al., "DNA sequence analysis by hybridization with oligonucleotides microchips;MALDI mass spectrometry identificaiton of 5mers contiguously stacked to microchip oligonucleotides," Nucleic Acids Res. Mar. 1, 2000;28(5):1193-1198.
Takenawa, J.et al., "Transcript Levels of Aquaporin 1 and Carbonic Anhydrase IV as Predictive indicators for Prognosis of Renel Cell . . . " Int. J. Cancer, 1998, 1-7, 79, Japan.
Uracil-DNA Glycosylase (UDG), product description. New England Biolabs. http://circuit.neb.com/neb/products/mod_enzymes/280.html, (Dec. 21, 2000).
Uracil-DNA Glycosylase, product description. Roche Molecular Biochemicals Catalog Version 3, Nov. 1999 http:/biochem.roche.com/pack-insert/1269062a.pdf, (Dec. 21, 2000).
Vacca, A. et al., "Microvessel overexprssion of aquaporin 1 parallels bone marrow angiogenesis in patients with active . . . " British J. of Haematology, 2001,415-421,113, Italy.
Wada, K. et al., "Aberrant Expression of the Maspin Gene Associated,with Epigenetic Modification," J. Invest Dermatol, 2004, 805-811, 122, Japan.
Xiong et al., "Cobra: A sensitive and quantitative DNA methylation assay," Nucleic Acids Res. Jun. 15, 1997;25(12):2532-2534.
Yatabe, Y. et al., "Maspin expression in normal lung and non-small-cell lung cancers: cellular property . . . " Oncogene, 2004,4041-4049, 23, Japan.
Zendman, A. et al., "The XAGE Family of Cancer/Testis-Associated Genes: Alignment and Expression Profile in Normal Tissues . . . " Int. J. Cancer, 2002,361-369,99 Netherlands.
Zhu et a., "Use of DNA Methylation for cancer detection and molecular classification," J Biochem Mol Biol. Mar. 31, 2007;40(2):135-141.
Zou et al., "Maspin, a serpin with tumor-suppressing activity in human mammary epithelial cells," Science, Jan. 28, 1994;263(5146):526-529.
Aurup et al., Biochemistry, 31: 9636-9641 (1992).
Bachem et al., The Plant Journal, 9: 745-753 (1996).
Bonnin et al., J. Mol. Biol., 290: 241-251 (1999).
Chan et al., Oncogene, 2003, vol. 22, pp. 924-934.
Clayton et al., Curr. Opin. Microbiol., 1: 562-566 (1998).
Conrad et al., Nucleic Acids Res., 23: 1845-1853 (1995).
Contreras et al., FEBS Lett., 16: 281-283 (1971).
Crain et al., Curr. Opin. in Biotechnol., 9: 25-34 (1998).
Deng et al., Cancer Research, 1999, vol. 59, pp. 2029-2033.
Eckstein, Ann. Rev. Biochem., 54: 367-402 (1985).
Eng et al., Nature Biotechnol., 15; 422-426 (1997).
Fleischmann et al., Science, 269: 496-512 (1995).
Frommer et al., "A Genomic Sequencing Protocol that Yields a Positive Display of 5-Methylcytosine Residues in Individual DNA Strands," PNAS, vol. 89, Mar. 1, 1992 p. 1827-1831.
Gao et al., Proc. Natl. Acad. Sci. USA, 94: 407-411 (1997).
Gish et al., Nucleic Acids Symp. Ser., pp. 253-256 (1987).
Gish et al., Science, 240: 1520-1522 (1988).
Hertogs et al., Animicrob. Agents Chemother., 42: 269-276 (1998).
International Search Report and Written Opinion received in PCT/US2006/30256 mailed on: Aug. 14, 2008.
Isola et al., Anal. Chem., 71: 2266-2269 (1999).
Ivanova et al., Nucleic Acids Res., 23: 2954-2958 (1995).
Kato, Nucleic Res., 23: 3685-3690 (1995).
Lander et al., Science, 265: 2037-2048 (1994).
Lee et al.; Proc. Natl. Acad. Sci. USA, 92: 8303-8307 (1995).
Liang et al., Science, 257: 967-971 (1992).
Limbach, Mass Spectrom. Rev., 15: 297-336 (1996).
Lipshutz et al., Curr. Opin. in Struct. Biol., 4: 376-380 (1994).
Little et al., J. Am. Chem. Soc., 116: 4893-4897 (1994).
Loverix et al., Nature Struct. Biol., 5: 365-368 (1998).
Meador et al., Eur. J. Biochem., 187: 549-553 (1990).
Milligan et al., Nucleic Acids Res., 15: 8783-8798 (1987).
Murray, J. Mass Spectrom, 31; 1203-1215 (1996).
New England BioLabs Catalog, T4 DNA polymerase, T7 RNA polymerase, pp. 74-75, 1996/1997.
Nickerson et al., Nature Genet., 19: 233-240 (1998).
Nordhoff et al., J. Mass Spectrom., 30: 99-112 (1995).
Office Action mailed: Jun. 24, 2009 in U.S. Appl. No. 11/089,805, filed Mar. 24, 2005 Published as: US-2005-0272070 on Dec. 8, 2005.
Office Action mailed: Jan. 15, 2008 in U.S. Appl. No. 11/089,805, filed Mar. 24, 2005 Published as: US-2005-0272070 on Dec. 8, 2005.
Office Action mailed: Jan. 19, 2007 in U.S. Appl. No. 11/222,991, filed Sep. 8, 2005, Published as: US-2006-0073501A on Apr. 6, 2006.
Office Action mailed: Jan. 23, 2007 in U.S. Appl. No. 10/830,943, filed Apr. 22, 2004 Published as: US-2005-0009053A1 on Jan. 13, 2005.
Office Action mailed: Jan. 24, 2003 in U.S. Appl. No. 10/018,453, filed Oct. 30, 2001, Now U.S. Pat. No. 6,994,969 Issued on: Feb. 7, 2006.
Office Action mailed: Jan. 27, 2008 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Jan. 27, 2009 in U.S. Appl. No. 10/888,359, filed Jul. 9, 2004 Published as: US-2006-0210992A1 on Sep. 21, 2006.
Office Action mailed: Jan. 30, 2009 in U.S. Appl. No. 11/348,683, filed Feb. 7, 2008 Published as: US-2006-0252061A1 on Nov. 9, 2006.
Office Action mailed: Oct. 26, 2004 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Oct. 9, 2007 in U.S. Appl. No. 10/830,943, filed Apr. 22, 2004 Published as: US-2005-0009053A1 on Jan. 13, 2005.
Office Action mailed: Dec. 12, 2005 in U.S. Appl. No. 10/723,365, filed Nov. 26, 2003 Published as: US-2005-0112590A1 on May 26, 2005.
Office Action mailed: Dec. 16, 2008 in U.S. Appl. No. 11/222,991, filed Sep. 8, 2005, Published as: US-2006-0073501A on Apr. 6, 2006.
Office Action mailed: Dec. 5, 2006 in U.S. Appl. No. 10/723,365, filed Nov. 26, 2003 Published as: US-2005-0112590A1 on May 26, 2005.
Action mailed: Dec. 8, 2008 in U.S. Appl. No. 10/723,365, filed Nov. 26, 2003 Published as: US-2005-0112590A1 on May 26, 2005.
Office Action mailed: Feb. 2, 2009 in U.S. Appl. No. 11/089,805, filed Mar. 24, 2005 Published as: US-2005-0272070 on Dec. 8, 2005.
Office Action mailed: Feb. 29, 2008 in U.S. Appl. No. 10/723,365, filed Nov. 26, 2003 Published as: US-2005-0112590A1 on May 26, 2005.

(56) References Cited

OTHER PUBLICATIONS

Office Action mailed: Feb. 6, 2009 in U.S. Appl. No. 10/830,943, filed Apr. 22, 2004 Published as: US-2005-0009053A1 on Jan. 13, 2005.
Office Action mailed: Mar. 31, 2008 in U.S. Appl. No. 11/348,683, filed Feb. 7, 2006 Published as: US-2006-0252061A1 on Nov. 9, 2006.
Office Action mailed: Mar. 8, 2006 in U.S. Appl. No. 10/723,365, filed Nov. 26, 2003 Published as: US-2005-0112590A1 on May 26, 2005.
Office Action mailed: Apr. 19, 2005 in U.S. Appl. No. 10/018,453, filed Oct. 30, 2001, Now U.S. Pat. No. 6,994,969 issued on: Feb. 7, 2006.
Office Action mailed: Apr. 2, 2008 in U.S. Appl. No. 11/222,991, filed Sep. 8, 2005, Published as: US-2006-0073501A on Apr. 6, 2006.
Office Action mailed: May 16, 2007 in U.S. Appl. No. 11/222,991, filed Sep. 8, 2005, Published as: US-2006-0073501A on Apr. 6, 2006.
Office Action mailed: May 2, 2007 in U.S. Appl. No. 11/089,805, filed Mar. 24, 2005 Published as: US-2005-0272070 on Dec. 8, 2005.
Office Action mailed: May 20, 2008 in U.S. Appl. No. 10/888,359, filed Jul. 9, 2004 Published as: US-2006-0210992A1 on Sep. 21, 2006.
Office Action mailed: Jun. 1, 2004 in U.S. Appl. No. 10/018,453, filed Oct. 30, 2001, Now U.S. Pat. No. 6,994,969 Issued on: Feb. 7, 2006.
Office Action mailed: Jul. 11, 2007 in U.S. Appl. No. 11/089,805, filed Mar. 24, 2005 Published as: US-2005-0272070 on Dec. 8, 2005.
Office Action mailed: Jul. 17, 2008 in U.S. Appl. No. 10/830,943, filed Apr. 22, 2004 Published as: US-2005-0009053A1 on Jan. 13, 2005.
Office Action mailed: Jul. 3, 2007 in U.S. Appl. No. 10/888,359, filed Jul. 9, 2004 Published as: US-2006-0210992A1 on Sep. 21, 2006.
Office Action mailed: Jul. 6, 2005 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Aug. 28, 2007 in U.S. Appl. No. 10/388,359, filed Jul. 9, 2004 Published as: US-2006-0210992A1 on Sep. 21, 2006.
Office Action mailed: Aug. 28, 2006 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Sep. 2, 2008 in U.S. Appl. No. 10/830,943, filed Apr. 22, 2004 Published as: US-2005-0009053A1 on Jan. 13, 2005.
Office Action mailed: Sep. 20, 2007 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Sep. 29, 2003 in U.S. Appl. No. 10/018,453, filed Oct. 30, 2001, Now U.S. Pat. No. 6,994,969 Issued on: Feb. 7, 2006.
Parsons et al., Environmental and Molecular Mutagenisis, 1998, vol. 32, p. 200-2111.
Parsons et al., Mutagenesis, 1998, vol. 13, No. 6, p. 581-588.
Pieles et al., Nucleic Acids Res., 21: 3191-3196 (1993).
Prashar et al., Proc. Natl. Acad. Sci. USA, 93: 659-663 (1996).
Rand et al., Methods, 2002, vol. 22 (27), pp. 114-120.
Richterich et al., Nucleic Acids Res., 23: 4922-4923 (1995).
Sakai et al., "Allele-Specific Hypermethylation of the Retinoblastoma Tumor-Supressor Gene," American Journal of Human Genetics, vol. 48, No. 5, 1991 pp. 880-888.
Sakai et al., American Journal of Human Genetics, 1991, vol. 48, p. 880-888.
Sanger et al., Proc. Natl. Acad. Sci. USA. 74: 5463-5467 (1977).
Schena et al., Science, 270: 467-470 (1995).
Schinazi et al., Int. Antivir. News, 4: 95-107 (1996).
Sousa et al., EMBOL J. 14: 4609-4621 (1995).
Stanssens et al., "High-throughput MALDI-TOF discovery of genomic sequence polymprphisms." Genome Research, vol. 14, No. 1, Jan. 2004, pp. 126-133.
Stevens, J. Bacteriol., 164: 57-62 (1985).
Steyaert, Eur. J. Biochem., 274: 1-11 (1997).
Stratagene Catalog (1998), p. 39. Published by Stratagene, 11011 North Torrey Pines Road, La Jolla, CA 92037, USA.
Supplemental European Search Report received in PCT/US2005/009929 mailed on Jan. 30, 2009.
Supplemental European Search Report received in PCT/US2005/032441 mailed on Nov. 28, 2008.
Tang et al., "Matrix-Assisted Laser Desorption/Ionization of Restriction Enzyme-digested DNA," Rapid Communications in Mass Spectrometry, vol. 8, pp. 183-186, 1994.
Tost et al., "Genotyping Single Nucleotide Polymorphisms by Mass Spectrometry," Mass Spectrometry Reviews, John Wiley and Sons, New York, vol. 21, No. 6, Nov. 1, 2002, p. 388-418.
Vaughn et al., Genetic Analysis: Biomolecular Engineering (1999) vol. 14, pp. 169-175.
Vos et al., Nucleic Acids Res., 23: 4407-4414 (1995).
Wodicka et al., Nature Biotechnol., 15: 1359-1367 (1997).
Office Action mailed: Jan. 25, 2010 in U.S. Appl. No. 11/089,805, filed Mar. 24, 2005 Published as: US-2005-0272070 on Dec. 8, 2005.
Aoki E. et al., "Methylation status of the pI5INK4B gene in hematopoietic progenitors and peripheral blood cells in myelodysplastic syndromes", Leukemia 14(4):586-593 (2000).
Asimakopoulos FA et al., "ABL 1 methylation is a distinct molecular event associated with clonal evolution of chronic myeloid leukemia" Blood 94(7):2452-2460 (1999).
Bair and Tibshirani, PloS Biol 2:E108 (2004).
Bullinger L. et al. N Engl J Med 350:1605-16 (2004).
Bullinger, L., "Gene Expression Profiling in Acute Myloid Leukemia," J. Clinical Oncology. Sep. 10, 2005, vol. 23, No. 26, pp. 6296-6305.
Colella et al. Biotechniques. Jul. 2003;35(1):146-150.
Dohner et al. J Clin Oncol 20:3254-61 (2002).
Dupont JM, Tost J, Jammes H, and Gut IG. Anal Biochem, Oct. 2004; 333(1): 119-27.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Feinberg, AP Nat Genet 27:9-10 (2001).
Frigola et al. Nat Genet. May 2006;38(5):540-9.
Friso et al., "A Method to Assess Genomic DNA Methylation Using High-Performance Liquid Chromatography/Electrospray Ionization Mass Spectrometry," Anal Chem, 2002, 74, p. 4526-4531.
Frohling et al. Blood 100:4372-80 (2002).
Gebhard et al. Cancer Res. Jun. 15, 2006;66(12):6118-28.
Genebank Accession No. NM_153620, Jun. 15, 2008.
Genebank Accession No. AB025106, Jan. 7, 2000.
Genebank Accession No. AB040880, Feb. 22, 2001.
Genebank Accession No. BC013998, Sep. 11, 2007.
Genebank Accession No. NM_001031680, Jun. 15, 2008.
Genebank Accession No. NM_001394, Jun. 1, 2008.
Genebank Accession No. NM_001614, Feb. 10, 2008.
Genebank Accession No. NM_003998, May 25, 2008.
Genebank Accession No. NM_004350, Jun. 15, 2008.
Genebank Accession No. NM_004360, Jun. 15, 2008.
Genebank Accession No. NM_005522, Jun. 15, 2008.
Genebank Accession No. NM_005766, Feb. 11, 2008.
Genebank Accession No. NM_033317, Apr. 29, 2008.
Gunderson et al., "Mutation detection by ligation to complete n-mer DNA Arrays," Genome Res. Nov. 1998;8(11):1142-1153.
Issa JP, Nat Rev Cancer 4:988-93 (2004).
Jurinke et al., (1998) Rapid Comm in Mass Spec., vol. 12, p. 50-52.
Kaneko et al., Gut 52:641-646 (2003).
Laird, P.W. Nature Reviews Cancer 3, 253-266 (2003).
Litz C. E. et al., "Methylation status of the major breakpoint cluster region in Philadelphia chromosome negative leukemias" Leukemia 6(1):35-41 (1992).
Risch et al., Science, 273: 1516-1517 (1996.
Strathdee, et al., Am. J. Pathol. 158:1121-1127 (2001).
Tooke N and Pettersson M. IVDT. Nov. 2004; 41.
Toyota, M. et al., Blood 97:2823-2829 (2001).
Uhlmann, K. et al. Electrophoresis 23:4072-4079 (2002).
Valk PJ et al. N Engl J Med 350:1617-28 (2004).

(56) References Cited

OTHER PUBLICATIONS

Vaughan et al., "A novel process for mutation direction using uracil DNA-glycosolase," Nucleic Acids Research, Oxford University Press, Surrey, GB, vol. 26, No. 3, Feb. 1, 1998, pp. 810-815.
Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1657-1660, (1997).
Office Action mailed: Aug. 28, 2009 in U.S. Appl. No. 10/830,943, filed Apr. 22, 2004 Published as: US-2005-0009053A1 on Jan. 13, 2005.
Office Action mailed: Sep. 3, 2009 in U.S. Appl. No. 10/723,365, filed Nov. 26, 2003 Published as: US-2005-0112590A1 on May 26, 2005 and Issued as U.S. Pat. No. 7,820,378 on Oct. 26, 2010.
Office Action mailed: Jun. 14, 2010 in U.S. Appl. No. 10/723,365, filed Nov. 26, 2003 Published as: US-2005-0112590A1 on May 26, 2005 and Issued as U.S. Pat. No. 7,820,378 on Oct. 26, 2010.
Office Action mailed: Sep. 14, 2011 in U.S. Appl. No. 11/089,805, filed Mar. 24, 2005 Published as: US-2005-0272070 on Dec. 8, 2005.
Office Action mailed: Jun. 12, 2009 in U.S. Appl. No. 10/888,359, filed Jul. 9, 2004 Published as: US-2006-0210992A1 on Sep. 21, 2006 and Issued as U.S. Pat. No. 7,608,394 on Oct. 27, 2009.
Supplemental European Search Report dated May 7, 2010 received in EP0379490 filed on: Nov. 26, 2003 based on PCT/US0337931.
Supplemental European Search Report dated Apr. 28, 2009 received in EP05768312 filed on: Jul. 6, 2005 based on PCT/US05/023846.
European Search Report dated: Nov. 2, 2011 in European Application No. EP11006184 filed: Mar. 24, 2005.
Herman et al., "Methylation-specific PCR: a novel PCR assay for Methylation status of CpG islands," PNAS USA, vol. 93, No. 18, Sep. 3, 1996, pp. 9821-9826.
Rein et al., "Identifying 5-methylcytosine and related modifications in DNA genomes," Nucleic Acids Research, Oxford University Press, Surrey GB, vol. 26, No. 10, Jan. 1, 1998 pp. 2255-2264.
Office Action mailed: Aug. 20, 2009 in U.S. Appl. No. 11/348,683, filed Feb. 7, 2006 and published as: US 2006/0252061 on Nov. 9, 2006.
International Search Report and Written Opinion dated Nov. 8, 2006 in International Application No. PCT/US2005/32441, filed Sep. 8, 2005 and published as WO 06/031745 on: Mar. 23, 2006.
Extended European Search Report dated: Jul. 1, 2009 received in EP09157036 filed on Apr. 1, 2009.
Office Action mailed Nov. 19, 2014 in U.S. Appl. No. 11/348,683, filed Feb. 7, 2006 and published as US 2006-0252061 on Nov. 9, 2006.
Office Action mailed Jun. 20, 2013 in U.S. Appl. No. 11/348,683, filed Feb. 7, 2006 and published as US 2006-0252061 on Nov. 9, 2006.
Office Action mailed: Oct. 17, 2012 in U.S. Appl. No. 11/348,683, filed Feb. 7, 2006 and published as: US 2006/0252061 on Nov. 9, 2006.
"Phosphodiesterase" from Wikipedia, the free encyclopedia, printed on Jun. 13, 2013.
"Restriction enzyme" from Wikipedia, the free encyclopedia, printed on Jun. 13, 2013.
Clark, "Methylation Analysis," Mini-Review pp. 1-7, Jan. 1999, DNA Methylation Society.
Cline et al., Nucleic Acids Research, 1996, 24(18):3546-3551.
Ehrich et al., "Comparative Sequence Analysis by MALDI-TOF Mass Spectrometry—Utilizing the knowns to Discover the New," Chapter 3, Perspectives in Bioanalysis, vol. 2, Chapter 3, p. 97-117.
Ellington et al., Current Protocols in Molecular Biology, 1988, 2.11.1-2.11.25.
Fraga et al., "DNA Methylation: A Profile of Methods and Applications," Review in Biotechniques, 33:632-649, Sep. 2002.
Genereux et al., "Errors in bisulfate conversion of DNA: modulating inappropriate- and failed-conversion frequencies," Nucleic Acid Research, Nov. 4, 2008, vol. 36, No. 22, e150, 1-19.
Graff et al., "Mapping Patters of CpG island methylation in normal and neoplasitc cells implicates both upstream and downstream regions in de novo methylation," Journal of Biological Chemistry, The American Society of Biological Chemists, Inc., Aug. 29, 1997, pp. 22322-22329.
Griffin et al., "Direct genetic analysis by matrix-assisted laser desorption/ionization mass spectrometry" PNAS USA (1999) 96:6301-6306.
Harrison et al., "DNA Methylation: a timeline of Methods and Applications," Review Article in Frontiers in Genetics, Oct. 25, 2011, vol. 2, Article 74, p. 1-13.
Herman et al., "Methylation-specific PCR: a novel PCR assay for Methylation status of CpG islands," PNAS USA, vol. 93, No. 18, Sep. 3, 1996.
Holland et al., PNAS, 1991, vol. 88, p. 7276-7280.
Mikeska et al, "The implications of heterogeneous DNA methylation for the accurate quantification of methylation," Epigenomics, (2010) 2(4), 561-573.
Model et al., "Feature Selection for DNA Methylation Based Cancer Classification" Bioinformatics, Oxford University Press, Surrey, GB, vol. 17, No. Suppl. 01, Jan. 1, 2001.
Nosaka, K. et al., "Increasing methylation of the CDKN2A gene is associated with the progression of adult Tcell leukemia", Cancer Res. 60(4):1043-1048 (2000).
Rauch et al., "High-resolution mapping of DNA Hypermethylation and hypomethylation in lung cancer." PNAS, Jan. 8, 2008, vol. 105, No. 1, p. 257-252.
Singal et al., "DNA Methylation, Review Article." Blood, vol. 93, No. 12, Jun. 15, 1999, pp. 4059-4070.
Yang et al., "A simple method for estimating global DNA methylation using bisulfater PCR of repetitive DNA elements," Nucleic Acids Research, Feb. 18, 2004, vol. 32, No. 3, e38, 1-6.
Office Action mailed on Jul. 24, 2012 in U.S. Appl. No. 11/089,805, filed Mar. 24, 2005 and published as US 2005-0272070 on Dec. 8, 2005.
Office Action mailed on Sep. 18, 2013 in U.S. Appl. No. 11/089,805, filed Mar. 24, 2005 and published as US 2005-0272070 on Dec. 8, 2005.
Office Action mailed Mar. 24, 2014 in U.S. Appl. No. 11/348,683, filed Feb. 7, 2006 and published as US 2006-0252061 on Nov. 9, 2006.
Office Action mailed on Jun. 3, 2014 in U.S. Appl. No. 11/089,805, filed Mar. 24, 2005 and published as US 2005-0272070 on Dec. 8, 2005.

* cited by examiner

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
ggccagcgtc tgacgttatg agc                                            23

<210> SEQ ID NO 2
<211> LENGTH: 201
<212> TYPE: DNA
<213> ORGANISM: Homo sapien
<220> FEATURE:
<221> NAME/KEY: misc_feature
<222> LOCATION: (1)...(201)
<223> OTHER INFORMATION: IKBA amplicon
<220> FEATURE:
<221> NAME/KEY: misc_feature
<222> LOCATION: 23
<223> OTHER INFORMATION: n = C or T
<220> FEATURE:
<221> NAME/KEY: misc_feature
<222> LOCATION: 39
<223> OTHER INFORMATION: n = G or C
<220> FEATURE:
<221> NAME/KEY: misc_feature
<222> LOCATION: (103)...(105)
<223> OTHER INFORMATION: nnn = AAA or deletion
<220> FEATURE:
<221> NAME/KEY: misc_feature
<222> LOCATION: 147
<223> OTHER INFORMATION: n = G or A

<400> SEQUENCE: 2
ggccagcgtc tgacgttatg agngcaaagg ggctgaaana acatggactt gtatatttgt    60
acaaaaaaaa agttttattt ttctaaaaaa agaaaaaaga agnnnaaatt taagggtgt    120 acttatatcc acactgcaca ctgcctngcc caaaacgtct tattgtggta ggatcagccc   180
tcattttgtt gcttttgtga a                                            201

<210> SEQ ID NO 3
<211> LENGTH: 57
<212> TYPE: DNA
<213> ORGANISM: Artificial Sequence
<220> FEATURE:
<223> OTHER INFORMATION: Primer

<400> SEQUENCE: 3
cagtaatacg actcactata agggagaagg ctttcacaaa agcaacaaaa tgagggc       57

<210> SEQ ID NO 4
<211> LENGTH: 23
<212> TYPE: DNA
<213> ORGANISM: Artificial Sequence
<220> FEATURE:
<223> OTHER INFORMATION: Primer
```

```
<220> FEATURE:
<221> NAME/KEY: modified_base
<222> LOCATION: 23
<223> OTHER INFORMATION: n = inverted T base

<400> SEQUENCE: 4
ggccagcgtc tgacgttatg agn                                              23

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
atatccacac tgcacactgc ct                                               22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ggccagcgtc tgacgttatg agt                                              23

<210> SEQ ID NO 7
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 23
<223> OTHER INFORMATION: n = dideoxycytosine

<400> SEQUENCE: 7
ggccagcgtc tgacgttatg agn                                              23

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ggccagcgtc tgacgttatg aac                                              23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ggccagcgtc tgacgttatg aat                                              23

<210> SEQ ID NO 10
<211> LENGTH: 1998
<212> TYPE: DNA
<213> ORGANISM: Homo sapien
```

```
<220> FEATURE:
<221> NAME/KEY: misc_feature
<222> LOCATION: 22
<223> OTHER INFORMATION: n = C or A
<220> FEATURE:
<221> NAME/KEY: misc_feature
<222> LOCATION: 336, 515, 1676
<223> OTHER INFORMATION: n = G or A
<220> FEATURE:
<221> NAME/KEY: misc_feature
<222> LOCATION: 575,
<223> OTHER INFORMATION: n = A or G
<220> FEATURE:
<221> NAME/KEY: misc_feature
<222> LOCATION: 796
<223> OTHER INFORMATION: n = A or T
<220> FEATURE:
<221> NAME/KEY: misc_feature
<222> LOCATION: 1483
<223> OTHER INFORMATION: n = T or G
<220> FEATURE:
<221> NAME/KEY: misc_feature
<222> LOCATION: 1664
<223> OTHER INFORMATION: n = T or A
<220> FEATURE:
<221> NAME/KEY: misc_feature
<222> LOCATION: 1940
<223> OTHER INFORMATION: n = C or deletion

<400> SEQUENCE: 10
aagagcggag ctctccgagt gngcaattcc tgtcccttttt aagggctcac aactctaagg      60
gggtctgcat gagagggtcg tgatctattg agcaagtagc aggtacgtga ctgggggctg     120
catgcaccgg taatcagaac gaaacagaac aggacaggga tttttacaat gctctttcat     180
gcaatgtctg gaatctatag ataacataac tggttaggtc agggtccat ctttaactac      240 caggcttagg tcaggtaggc ccaggcctgg tttcgggtct ggttccttgg tttcgggtct     300
ggtctctagg cgttgggcta cctgccttta gttctcnctt ctctttctttt tctgagtata     360 aaacaatata aaacaatatg agagggtctg tctctcttct ctcagagaca ggagggtccc     420
tggaggccag gagttcaaga ccagcctggg caacatgggg agaccctgt ctctacaaaa      480 ataaaaataa gtttaaaaat cagctgtgca cggcngtgca tacctatagt cccaactact     540
caggtggctg aggagggagg atcacttgag cccangaggt tgaggctgca gtgagctatg     600
atggcaccac tgcactccag tgtgggtgac agagtaggac tccatctcaa gaaaaaaata     660
cagtccagca tttattggag tcaactatgt gttgccagat agatagatgg atagatagac     720
agagtgatca atagatttag gtatagatat aacttggcac gtagtaactg tgcattaaat     780
ataagttgat attagnctta catttattgc agttatattt gctacacttt gttttgttgc     840
actcatcctg tgaaataagt actgttacct ctgttttgca aacaaaaaaa ccacaaagct     900
cagagaaggt aggtgactta ctgaagatca cacagcctgt aagaggtggc cccaaagcct     960
gtactcttca cctatactgt actagaaatg cttaggtagt ttccaggctg tgcttgtcat    1020
tgaactcatg aggaaactga gcccacaga ggggaagaga cttgtgcgag gtcacacagc    1080
atgtgtgggg cacagtgggg agcagaagcc aggcctccag ccgggacagg ggttccctgt    1140
tccacaccct gcccagagca tctcacatgt tgtctgggag gttgggagtt gcgtctgagg    1200
aggggtccag tccttgaaac tgcccttggt ccctgcgaag ttttcttctg aggagtggac    1260
tttactccac ccaccctcca acttcctcat ttcttttcag gcagtgctgg agacctgggg    1320
cttcaacacc aaccaggaaa tcttccaaga ggtaactgcc cctgccccct gtgtggggtt    1380
tatctcacgt accccaatcc tgctctggct tcaagagccc ccacacagcc aataacacca    1440
```

```
ccaatggcaa caattataac agcgaacaca gctcctactc ggntgttcgg catggagtga    1500
agcacttagt gtgtgtgact tccttcagtg ctcacaccga ccctatgagt ggggcggtca    1560
aactgtcccc attttacaca cagggaaact tagtgaatgg caaggctggg tttgagccca    1620
gctctattgc ccccaaagat aaggctccat tccctgctcc attncccagg catagngact    1680 tgtaggggc tggaacccca ggatcaactc tgggctcaga gggccccagc aataagtgac     1740
tgttgattac tcctgatccc aaagctgact tcaggcaagc tccttggagg tcgcagcccc    1800
ttcttgctat gcccagtggc aatgatgttc ataatcccac tcctcagtgc agggttccac    1860
taagaaccca tgatctccta cctcaaatgg acctcatgct ttctgagtaa gcctccctca    1920
gctttctggt cacctcactn cccccaccca ctgcaatgac ttcttcaggc cttccctgcc    1980
atcctcaaat ctccagct                                                  1998

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
aagagcggag ctctccgagt ga                                             22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
aagagcggag ctctccgagt gc                                             22

<210> SEQ ID NO 13
<211> LENGTH: 53
<212> TYPE: DNA
<213> ORGANISM: Artificial Sequence
<220> FEATURE:
<223> OTHER INFORMATION: primer

<400> SEQUENCE: 13
cagtaatacg actcactata gggagaaggc taagagcgga gctctccgag tga           53

<210> SEQ ID NO 14
<211> LENGTH: 53
<212> TYPE: DNA
<213> ORGANISM: Artificial Sequence
<220> FEATURE:
<223> OTHER INFORMATION: primer

<400> SEQUENCE: 14
cagtaatacg actcactata gggagaaggc taagagcgga gctctccgag tgc           53

<210> SEQ ID NO 15
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: 22
<223> OTHER INFORMATION: n = inverted base
```

```
<400> SEQUENCE: 15
aagagcggag ctctccgagt gn                                              22

<210> SEQ ID NO 16
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: 22
<223> OTHER INFORMATION: n = dideoxycytosine

<400> SEQUENCE: 16
aagagcggag ctctccgagt gn                                              22

<210> SEQ ID NO 17
<211> LENGTH: 55
<212> TYPE: DNA
<213> ORGANISM: Artificial Sequence
<220> FEATURE:
<223> OTHER INFORMATION: primer

<400> SEQUENCE: 17
cagtaatacg actcactata gggagaaggc tagctggaga tttgaggatg gcagg          55

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
agctggagat ttgaggatgg cagg                                            24

<210> SEQ ID NO 19
<211> LENGTH: 23
<212> TYPE: DNA
<213> ORGANISM: Artificial Sequence
<220> FEATURE:
<223> OTHER INFORMATION: T7 tag

<400> SEQUENCE: 19
cagtaatacg actcactata ggg                                             23

<210> SEQ ID NO 20
<211> LENGTH: 25
<212> TYPE: DNA
<213> ORGANISM: Artificial Sequence
<220> FEATURE:
<223> OTHER INFORMATION: SP6 tag

<400> SEQUENCE: 20
cgatttagga gacactatag aagag                                           25
```

ALLELE-SPECIFIC SEQUENCE VARIATION ANALYSIS

RELATED APPLICATIONS

This application claims the benefit of priority under 35 U.S.C. §119(e) to U.S. Provisional Application Ser. No. 60/500,489, to Martin Beaulieu and Dirk van den Boom, filed Sep. 5, 2003, entitled "ALLELE-SPECIFIC SEQUENCE VARIATION ANALYSIS," the subject matter and disclosure of which is incorporated herein in its entirety.

The subject matter and disclosure of each of the following applications also is incorporated herein by reference in its entirety: International PCT Application PCT/US2004/028997, to Beaulieu et al., entitled "ALLELE-SPECIFIC SEQUENCE VARIATION ANALYSIS," filed Sep. 2, 2004; U.S. Provisional Application 60/429,895, to van den Boom et al., filed Nov. 27, 2002, entitled "FRAGMENTATION-BASED METHODS AND SYSTEMS FOR SEQUENCE VARIATION DETECTION AND DISCOVERY;" and U.S. application Ser. No. 10/723,365, to van den Boom et al., filed Nov. 26, 2003 entitled "FRAGMENTATION-BASED METHODS AND SYSTEMS FOR SEQUENCE VARIATION DETECTION AND DISCOVERY."

FIELD OF THE INVENTION

Methods for biomolecular analysis are provided.

BACKGROUND

The use of SNPs as polymorphic markers for linkage disequilibrium (LD) studies offers great potential. Their lack of informativeness is believed to be mostly compensated by 1) their number, over 1.4 million, and 2) their relatively homogeneous distribution throughout the human genome. In certain embodiments for genes containing multiple SNPs, haplotype structure rather than individual SNPs can be the principal determinant of phenotypic consequences. In addition, haplotype analysis is a popular tool in assessing LD and for mapping complex disease genes in association studies where SNP-phenotype associations may not be detectable. Numerous studies have indicated that haplotypes can provide additional power in detecting association.

Haplotypes are the collection of genotypes that occur in a single allele or chromosome. Due to the diploidy nature of the human genome, the challenge is to obtain genotype data from a single chromosome or allele. There are two ways to perform haplotyping: 1) Computational haplotyping and 2) Molecular haplotyping. The first involves converting diploidic genotype information into estimated haplotypes. This method offers only a statistical approximation of an individual's haplotype structure. The second method provides haplotype determination through physical allele selection followed by genotyping analysis. Such a molecular approach may provide a more accurate picture.

No high-throughput methods for allele selection are available. One available method for obtaining a specific allele involves converting diploidic cells to haploidic clones. This, however, is a cost and time prohibitive process. Other approaches use conventional Allele-Specific-PCR/genotyping. A challenge with conventional Allele-Specific PCR (AS-PCR) is potential for amplification leakage, i.e., amplification of the undesired wrong allele. Accordingly, there is a need for methods for sequence analysis of specific alleles that reduces allele leakage, and methods that permit high-throughput analysis. Accordingly, among the objects herein, it is an object to provide such methods.

SUMMARY OF THE INVENTION

Provided herein are methods for sequence analysis of specific alleles with reduced allele leakage. These methods are susceptible to high-throughput analysis. In particular, provided herein are methods for direct molecular sequence analysis (e.g., haplotyping) of a plurality of polymorphic markers (loci) in a single reaction. These methods have a variety of applications. For example, they can be used for detecting disease association for HLA-typing and for forensic analysis. Also provided are leakage-reduced allele-specific PCR (AS-PCR) methods that improve allele-specificity. These methods use a non-extendable and exonuclease resistant competitor oligonucleotide that is added to the amplification reaction. The latter exonuclease resistant feature allows the use of proofreading polymerases, which in turn permits long-range AS-PCR (e.g., amplification of regions ≥5-10 Kb). This method of AS-PCR is referred to herein as Non-Extendable Exonuclease Resistant AS-PCR (NEER-AS-PCR). The region or regions amplified can be used, for example, as templates or target nucleic acids for subsequent genotyping assays.

The methods provided herein have been used, for example, in quantitative primer mass extension reactions (such as the MassEXTEND™ reaction kit and protocol available from Sequenom, San Diego, Calif.; see e.g., U.S. Pat. No. 6,428,955 and WO 98/20166) and have demonstrated significant reduction in leakage when using an excess of the competitor. As an example of the method (see in Example 3), several regions from the CETP gene locus have been analyzed using the sequence variation analysis methods provided herein, demonstrating robustness and accuracy of the methods.

For sequence variation analysis involving multiple marker haplotypes, the markers are typically genotyped individually. In one embodiment, to circumvent this requirement, NEER-AS-PCR has been combined with a mass spectrometry based method of genotyping using base-specific cleavage (fragmentation) of nucleic acids (e.g., MassCLEAVE™ assay). The NEER-AS-PCR derived amplification product was subject to in vitro transcription and cleaved in up to four reactions at each of the respective four specific bases. The cleavage products were analyzed by MALDI-TOF MS generating sequence specific mass signal patterns. Cross-comparison of theoretical and experimental mass pattern allowed haplotype determination. The methods provided herein were applied to the determination of molecular haplotypes in the CETP gene and these haplotypes were compared to the haplotypes inferred from genotyping the respective polymorphic loci individually. A key advantage of the methods provided herein is that they are not limited to detecting known sequence variations, but can also detect haplotypes containing previously undiscovered sequence variations that can be associated with sub-haplotypes. Thus, in addition to permitting the detection of known SNPs of a particular haplotype, the methods also allow the detection of newly discovered SNPs within a particular haplotype. Using mass detection genotyping methods (e.g., MALDI-TOF MS), the methods provided herein generate comprehensive haplotype information.

Accordingly, provided herein are methods of sequence variation analysis, (such as genotyping or haplotyping), comprising:

a) modifying a mixture of nucleic acids to obtain a target nucleic acid sequence corresponding to a single or specific allele;

b) fragmenting the target nucleic acid sequence, or a nucleic acid product transcribed from the target nucleic acid sequence of step a), at a plurality of specific and predictable sites;
c) fragmenting or simulating fragmentation of a reference target nucleic acid into fragments at the same plurality of specific and predictable sites of step b); and
d) genotyping the nucleic acid sequence corresponding to a single or specific allele at one or more loci.

The sequence variation analysis can be selected from any method known to those of skill in the art including, but are not limited to, genotyping, haplotyping, HLA-typing or re-sequencing. In an exemplary embodiment of the methods provided herein, set forth in FIG. 1, two general steps are used. First, a specific allele is amplified by an Allele Specific-PCR (AS-PCR) reaction supplemented with a Non-Extendable Exonuclease Resistant competitor oligonucleotide (NEER competitor). The NEER competitor is designed to function as an extension inhibitor of the unwanted allele. Second, the amplification products generated are genotyped using any available genotyping method, such as by hME (homogeneous MassEXTEND™ reaction) or hMC (homogeneous MassCLEAVE™ assay). In this embodiment, the exonuclease-resistance feature of the NEER competitor oligo has been designed to prevent degradation by the 3'→5' exonuclease activity of DNA polymerase. This exonuclease-resistance activity can be observed when using long-range PCR enzyme mixes containing polymerases with proofreading activity, or a combination of a polymerase and a proofreading enzyme. In this embodiment, the use of a non-extendable exonuclease-resistant competitor oligo is an advantageous feature for achieving long-range molecular haplotyping.

In one embodiment, modifying a mixture of nucleic acids is conducted by amplifying a target nucleic acid to obtain a specific allele, such as by conducting Allele-Specific PCR amplification. In another embodiment, the amplification step is PCR amplification from a diluted DNA sample containing an amount of haploid genome equivalents selected from 10, 9, 8, 7, 6, 5, 4, 3, 2 or 1. When utilizing the Non-Extendable Exonuclease Resistant (NEER) AS-PCR methods provided herein, the amplification step is conducted in the presence of a competitor oligonucleotide that is non-extendable by a polymerase (see FIG. 1). In particular embodiments, the amplification step is conducted in the presence of a competitor oligonucleotide that is non-extendable and exonuclease resistant.

To render the competitor oligonucleotide non-extendable and/or exonuclease resistant, the competitor oligonucleotide comprises a modified 3'-end nucleotide. In particular embodiments, the 3'-end nucleotide modification is selected from an inverted base, a dideoxynucleotide, a ribonucleotide, a 3' Phosphate, a carbon chain spacer, or a peptide nucleic acid (PNA), and the like. In the NEER-ASPCR amplification reaction, the competitor oligonucleotide can be added to the amplification reaction in an excess amount over a concentration of the AS-PCR amplification primer selected from: 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold or 75-fold or more. The AS-PCR amplification primer is designed to anneal to the desired allele at its 3'-most nucleotide. The resulting target nucleic acid sequence obtained by the NEER-ASPCR methods provided herein corresponds to a single or specific allele having a specificity of an amount selected from greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 99.1%, 99.2%, 99.3%, 99.4%, 99.5%, 99.6%, 99.7%, 99.8%, 99.9% of the desired allele relative to the undesired allele. In particular embodiments, the NEER-ASPCR amplification step is conducted in the presence of at least one oligonucleotide primer that comprises a promoter sequence. In one embodiment, the polymerase is an RNA polymerase.

To achieve long range amplification (e.g., amplifying greater than 5-10 kb), the amplification is performed in the presence of a thermostable DNA polymerase, or a mixture of thermostable DNA polymerases, having exonuclease activity.

In one embodiment, the specific and predictable fragmentation in step b) above, is base-specific fragmentation. For example, the fragmenting steps b) and/or c) can be conducted by contacting the target nucleic acid with one or more specific cleavage reagents.

In a particular embodiment, the genotyping step comprises:
c) determining mass signals of the fragments produced in a) and b);
d) determining differences in the mass signals between the fragments produced in a) and the fragments produced in b); and
e) determining a reduced set of sequence variation candidates from the differences in the mass signals and thereby determining sequence variations in the target compared to the reference nucleic acid. The target nucleic acid can be either DNA, cDNA or RNA. This particular genotyping step can further comprise scoring the candidate sequences and determining the sequence variations in the target nucleic acid molecule.

In a particular embodiment, determining a set of reduced sequence variation candidates comprises:
a) identifying fragments that are different between the target nucleic acid and the reference nucleic acid;
b) determining compomers corresponding to the identified different fragments in step a) that are compomer witnesses; and
c) determining a reduced set of sequence variations corresponding to the compomer witnesses that are candidate sequences to determine the sequence variations in the target nucleic acid compared to the reference nucleic acid. In certain embodiments, the differences in output signals are manifested as missing signals, additional signals, signals that are different in intensity, and/or as having a different signal-to-noise ratio. In a particular embodiment, the masses are determined by mass spectrometry. In these methods, the sequence variation is typically a mutation or a polymorphism. For example, the mutation can be an insertion, a deletion or a substitution, and the polymorphism can be a single nucleotide polymorphism. The target nucleic acid molecule can be from an organism selected from among eukaryotes (e.g., a human), prokaryotes (e.g., a bacterium) and viruses.

In particular embodiments, the specific cleavage reagent is an RNAse. The RNase can be selected from RNase $T_1$, RNase $U_2$, the RNase PhyM, RNase A, chicken liver RNase (RNase CL3) and cusavitin. In another embodiment, the specific cleavage reagent is DNA glycosylase-mediated.

Also provided herein are methods of obtaining a nucleic acid genotype or haplotype, comprising:
amplifying a target nucleic acid in the presence of a competitor oligonucleotide that is non-extendable and is exonuclease resistant; and genotyping the target nucleic acid. In a particular embodiment, the competitor oligonucleotide comprises a modified 3'-end nucleotide, such that it is non-extendable by a polymerase. The modified 3'-end nucleotide can be a modification selected from an inverted base, a dideoxynucleotide, a ribonucleotide, a 3' Phosphate, a carbon-chain spacer, or a PNA. In one embodiment, the amplification step is conducted in the presence of at least one oligonucleotide primer that comprises a promoter sequence. The polymerase cab be an RNA polymerase.

In a particular embodiment, the amplification is performed in the presence of a thermostable DNA polymerase, or a mixture of thermostable DNA polymerases, having exonuclease activity. The genotyping step can be conducted using base-specific fragmentation, and can further comprise mass spectrometric analysis.

DETAILED DESCRIPTION

Outline

Figure 1:
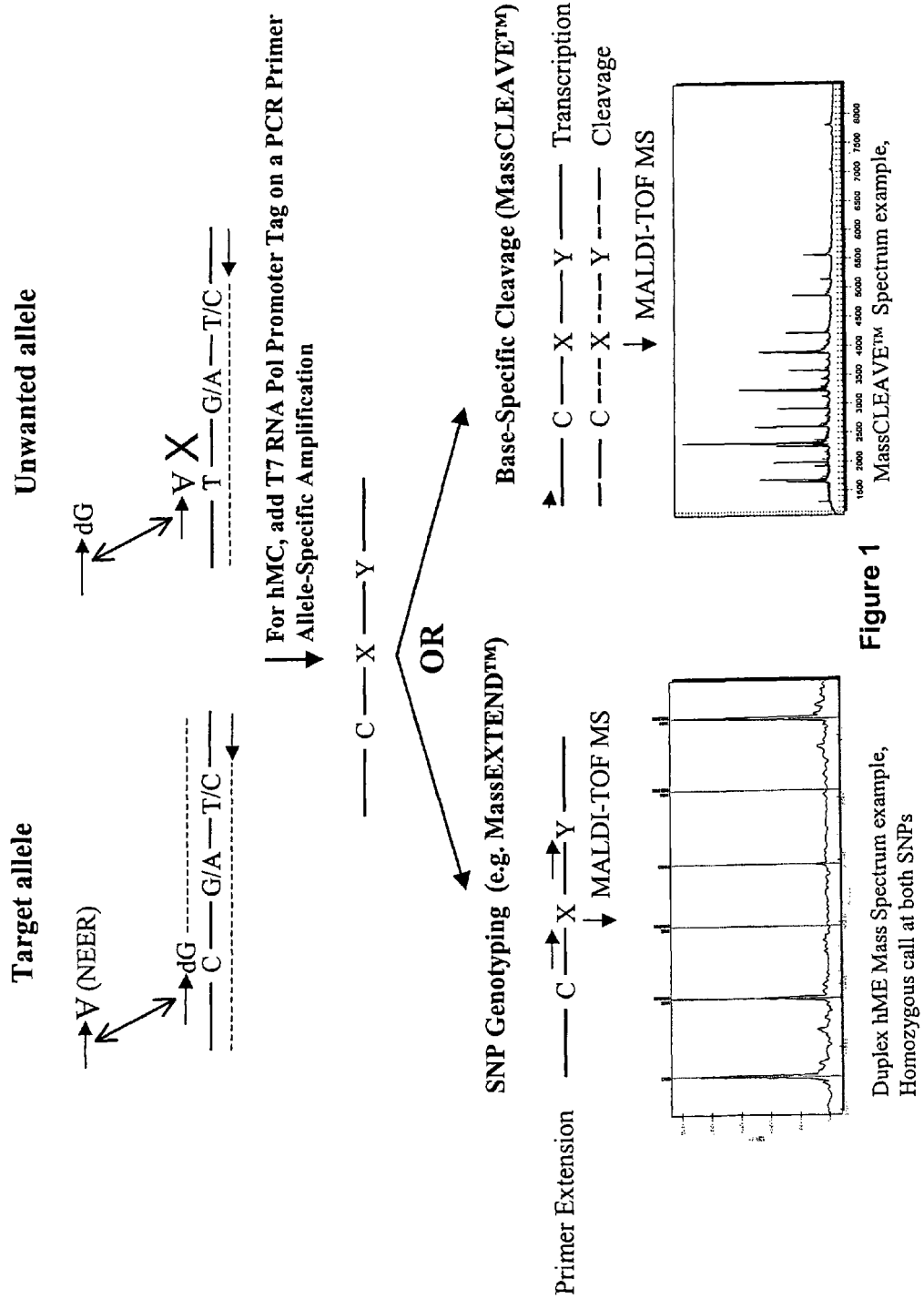
FIG. 1 shows a schematic representation of a haplotyping method provided herein. Allele-specific PCR amplification is performed using a Non-Extendable Exonuclease Resistant competitor oligonucleotide (NEER competitor). The Haplotype determination can then be achieved by genotyping the allele-specific PCR product using any genotyping method, such as a primer oligo base extension reaction (e.g., homogeneous MassEXTEND™ reaction available from Sequenom, San Diego, Calif.) and a base-specific cleavage assay (e.g. MassCLEAVE™ assay available from Sequenom, San Diego, Calif.).

A. Definitions
B. Methods of Obtaining Allele-Specific Target Nucleic Acids
  B.1. Amplification of Target
    B.1.a) NEER-AS-PCR
  B.2. Other Allele Selective Amplification Methods
    B.2.a) Double and Single Strand-based Allele Enrichment Methods
    B.2.b) Double-Stranded vs. Single-Stranded Allele Selection Methods
  B.3. Protein-based Allele Enrichment Methods
    B.3.a) Protein-based Double Stranded Allele Selection Methods
    B.3.b) Zinc Finger Proteins
    B. 3.c) Restriction Endonucleases
    B.3.d) Additional Restriction Endonuclease-Based Methods
  B.4. Nucleic Acid-based Allele Selection Methods
    B.4.a) Nucleic Acid-based Double Stranded Allele Selection Methods
    B.4.b) Other Double-Stranded Allele Selection Methods
  B.5. Allele Specific Capture of Single-Stranded DNA or RNA
C. Methods of Generating Nucleic Acid Fragments
D. Mass Acquisition
E. Techniques for Polymorphism, Mutation and Sequence Variation Discovery
  Algorithm 1: FindSequenceVariationCandidates
  Algorithm 2: FINDSNPs
  Algorithm 3: SCORESNP
F. Applications
  1. Detection of Polymorphisms
  2. Haplotyping
  3. HLA-Typing
G. System and Software Method

A. DEFINITIONS

Unless defined otherwise, all technical and scientific terms used herein have the same meaning as is commonly understood by one of skill in the art to which the inventions belong. All patents, patent applications, published applications and publications, GenBank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the phrase "sequence variation analysis" in the context of nucleic acid sequences refers to a variety of structural analyses that can be conducted to compare the physical structures of various target nucleic acids. Exemplary sequence variation analyses include genotyping, haplotyping, HLA-typing and re-sequencing, and the like.

As used herein, "haplotype" refers to the sequence (e.g., the determination of the identity of one or more nucleotides) of a segment of DNA from a single chromosome (allele). The DNA segment can include part of a gene, an entire gene, several genes, or a region devoid of genes (but that can contain DNA sequence that regulates the function of nearby genes). The term "haplotype," then, refers to a cis arrangement of two or more polymorphic nucleotides (or sequences) on a particular chromosome, e.g., in a particular gene or in two or more genes on the same chromosome. The haplotype preserves information about the phase of the polymorphic nucleotides. Thus, haplotyping provides information concerning which set of variances were inherited from one parent (and are therefore on one chromosome), and which from the other. A genotyping test does not provide information about phase unless it is performed on a single allele. For example, a subject heterozygous at nucleotide 25 of a gene (A and C are present) and also at nucleotide 100 of the same gene (G and T are present) can have haplotypes 25A-1 OOG and 25C-1 OOT, or alternatively 25A-1 OOT and 25C-100G. Only a haplotyping test can discriminate these two cases definitively. Haplotypes are generally inherited as units, except in the event of a recombination during meiosis that occurs within the DNA segment spanned by the haplotype, a rare occurrence for any given sequence in each generation. Usually the sample to be haplotyped initially includes two alleles of the chromosome segment to be haplotyped from a diploid subject. Haplotyping can include determining the nucleotide identity or nucleotide sequence of at least two polymorphic sites on a chromosome. Typically, obtaining a haplotype involves determining the nucleotide identity or nucleotide sequence of at least 3, 4, 5, 6, 7, 10, 15, 20, 25, 30, 40, 50, 100, or more polymorphic sites on the same chromosomal segment, e.g., a chromosomal segment of at least 2, 10, 50, 100, 200, 500, 1000, 2000, 3000, 4000, 5000, 10000, 20000 nucleotides or more.

As used herein, the phrase "modifying a mixture of nucleic acids to obtain a target nucleic acid sequence corresponding to a single or specific allele" refers to any known method for obtaining a specific allele from a nucleic acid mixture, such as a genomic DNA sample, RNA or cDNA. Suitable methods include amplifying a target nucleic acid to obtain a specific allele. The phrase "amplifying a target nucleic acid to obtain a specific allele" refers to any of the well-known amplification methods described hereinbelow for obtaining a single or specific allele.

As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine. Reference to a nucleic acid as a "polynucleotide" is used in its broadest sense to mean two or more nucleotides or nucleotide analogs linked by a covalent bond, including single-stranded or double-stranded molecules. The term "oligonucleotide" also is used herein to mean two or more nucleotides or nucleotide analogs linked by a covalent bond, although those in the art recognize that oligonucleotides such as PCR primers generally are less than about fifty to one hundred nucleotides in length. The term "amplifying," when used in reference to a nucleic acid, means the repeated copying of a DNA sequence or an RNA sequence, through the use of specific or non-specific means, resulting in an increase in the amount of the specific DNA or RNA sequences intended to be copied.

As used herein, the phrase "Allele-Specific PCR amplification" refers to amplification using the polymerase chain reaction to obtain a single or specific allele. One method of obtaining a single or specific allele using PCR is described in Ding and Cantor, *Proc. Natl. Acad. Sci. USA* 100(13):7449-7453 (2003), (incorporated herein by reference in its entirety) and uses a PCR amplification step from a diluted genomic DNA sample. The genomic DNA sample can be diluted down to about 10 or fewer genome equivalents of genomic DNA, such as down to 9, 8, 7, 6, 5, 4, 3, 2, or 1 haploid genome equivalent. As used herein "1 haploid genome equivalent" corresponds to the single molecule dilution of genomic DNA for the separation of two homologous genomic DNAs (e.g., the separation of two homologous chromosomes or fragments thereof).

Another method uses the NEER-AS PCR methods provided herein. As used herein, a "competitor oligonucleotide that is non-extendable" refers to an oligonucleotide designed to hybridize to the non-desired allele, such that upon binding primer extension of that allele by a polymerase does not occur.

As used herein, the term "exonuclease resistant" in the context of oligonucleotides refers to an oligonucleotide that cannot be degraded by the proofreading enzymatic activity of DNA polymerases.

As used herein, "nucleotides" include, but are not limited to, the naturally occurring nucleoside mono-, di-, and triphosphates: deoxyadenosine mono-, di- and triphosphate; deoxyguanosine mono-, di- and triphosphate; deoxythymidine mono-, di- and triphosphate; and deoxycytidine mono-, di- and triphosphate (referred to herein as dA, dG, dT and dC or A, G, T and C, respectively). Nucleotides also include, but are not limited to, modified nucleotides and nucleotide analogs such as deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mono-, di- and triphosphates, methylated nucleotides e.g., 5-methyldeoxycytidine triphosphate, $^{13}C/^{15}N$ labelled nucleotides and deoxyinosine mono-, di- and triphosphate. For those skilled in the art, it is clear that modified nucleotides, isotopically enriched, depleted or tagged nucleotides and nucleotide analogs can be obtained using a variety of combinations of functionality and attachment positions.

As used herein, the phrase "chain-elongating nucleotides" is used in accordance with its art recognized meaning. For example, for DNA, chain-elongating nucleotides include 2'deoxyribonucleotides (e.g., dATP, dCTP, dGTP and dTTP) and chain-terminating nucleotides include 2',3'-dideoxyribonucleotides (e.g., ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g., 3'dA, 3'dC, 3'dG and 3'dU) and 2',3'-dideoxyribonucleotides (e.g., ddATP, ddCTP, ddGTP, ddTTP). A complete set of chain elongating nucleotides refers to dATP, dCTP, dGTP and dTTP for DNA, or ATP, CTP, GTP and UTP for RNA. The term "nucleotide" also is well known in the art. As used herein, the term "nucleotide terminator" or "chain terminating nucleotide" refers to a nucleotide analog that terminates nucleic acid polymer (chain) extension during procedures wherein a DNA or RNA template is being sequenced or replicated. The standard chain terminating nucleotides, i.e., nucleotide terminators include 2',3'-dideoxynucleotides (ddATP, ddGTP, ddCTP and ddTTP, also referred to herein as dideoxynucleotide terminators). As used herein, dideoxynucleotide terminators also include analogs of the standard dideoxynucleotide terminators, e.g., 5-bromo-dideoxyuridine, 5-methyl-dideoxycytidine and dideoxyinosine are analogs of ddTTP, ddCTP and ddGTP, respectively.

As used herein, the phrase "a modified 3'-end nucleotide" refers to a nucleotide at the 3'-most end of an oligonucleotide that has been altered from its natural state, such that it imparts a particular functionality to the oligonucleotide, such as exonuclease resistance or non-extendibility.

As used herein, an "inverted base" (e.g., inverted T base, etc.) corresponds to a reverse linked nucleotide having an internal 3'-3' linkage therein (as opposed to the natural 5'-3' linkage), wherein the reverse linkage imparts nuclease resistance to a particular oligonucleotide to which it is reverse linked at the 3' end.

As used herein, the term "3' Phosphate" refers to the placement of the well-known phosphate group at the 3' end of an oligonucleotide in lieu of the naturally occurring hydroxyl group. The placement of the phosphate group at the 3' end of an oligonucleotide blocks chain elongation such that the oligonucleotide is rendered non-extendable.

As used herein, the phrase "carbon chain spacer" or "carbon chain linker" refers to a variety of well-known organic multi-carbon compounds (e.g., C-3 (propyl), C-5, C-7, C-9 or C-12 spacers; available from Trilink Biotechnologies, San Diego, Calif.; and see Schmidt et al., *NAR*, 24(4):573-581 (1996)) that function herein to render a primer non-extendable and/or exonuclease resistant.

The term "polypeptide," as used herein, means at least two amino acids, or amino acid derivatives, including mass modified amino acids, that are linked by a peptide bond, which can be a modified peptide bond. A polypeptide can be translated from a nucleotide sequence that is at least a portion of a coding sequence, or from a nucleotide sequence that is not naturally translated due, for example, to its being in a reading frame other than the coding frame or to its being an intron sequence, a 3' or 5' untranslated sequence, or a regulatory sequence such as a promoter. A polypeptide also can be chemically synthesized and can be modified by chemical or enzymatic methods following translation or chemical synthesis. The terms "protein," "polypeptide" and "peptide" are used interchangeably herein when referring to a translated nucleic acid, for example, a gene product.

As used herein, a fragment of biomolecule, such as biopolymer, into smaller portions than the whole. Fragments can contain from one constituent up to less than all. Typically when cleaving, the fragments are of a plurality of different sizes such that most contain more than two constituents, such as a constituent monomer.

As used herein, the phrase "fragments of a target nucleic acid" or "fragmenting the target nucleic acid" or grammatical variations thereof, refers to cleavage fragments produced by specific physical, chemical or enzymatic cleavage of the target nucleic acid. As used herein, fragments obtained by specific cleavage refers to fragments that are cleaved at a specific position in a target nucleic acid sequence based on the base/sequence specificity of the cleaving reagent (e.g., A, G, C, T or U, or the recognition of modified bases or nucleotides); or the structure of the target nucleic acid; or physical processes, such as ionization by collision-induced dissociation during mass spectrometry; or a combination thereof. Fragments can contain from one up to less than all of the constituent nucleotides of the target nucleic acid molecule. The collection of fragments from such cleavage contains a variety of different size oligonucleotides and nucleotides. Fragments can vary in size, and suitable nucleic acid fragments are typically less than about 2000 nucleotides. Suitable nucleic acid fragments can fall within several ranges of sizes including but not limited to: less than about 1000 bases, between about 100 to about 500 bases, between about 25 to about 200 bases, between about 15 to about 100 bases, between about 10 to about 75 bases, between about 5 to about 50 bases, between about 3 to about 30 bases, between about 2 to about 20 bases. In some aspects, fragments of about one nucleotide can be present in the set of fragments obtained by specific cleavage.

As used herein, a target nucleic acid refers to any nucleic acid of interest in a sample. It can contain one or more nucleotides. A target nucleotide sequence refers to a particular sequence of nucleotides in a target nucleic acid molecule. Detection or identification of such sequence results in detection of the target and can indicate the presence or absence of a particular mutation, sequence variation, or polymorphism. The phrase "target sequence" as used herein refers to either a target nucleic acid sequence or a target polypeptide or protein sequence.

As used herein, the phrase "a nucleic acid product transcribed from the target nucleic acid sequence" (e.g., of step A), refers to the product obtained when an amplified target sequence is transcribed using various selected chain-elongating nucleotides, as described herein. The resulting nucleic acid transcribed product can be DNA or RNA, or a combination thereof.

As used herein, the phrase "at a plurality of specific and predictable sites" or "specific and predictable cleavage" in the context of fragmentation of nucleic acids refers to well-known methods of fragmenting nucleic acids that can be achieved in many ways. For example, polynucleotides composed of DNA, RNA, analogs of DNA and RNA or combinations thereof, can be fragmented physically, chemically, or enzymatically, as long as the fragmentation is obtained by cleavage at a specific and predictable site in the target nucleic acid. Fragments can be cleaved at a specific position in a target nucleic acid sequence based on (i) the base specificity of the cleaving reagent (e.g., "base-specific fragmentation" using A, G, C, T or U, or the recognition of modified bases or nucleotides); or (ii) the structure of the target nucleic acid; or (iii) the physicochemical nature of a particular covalent bond between particular atoms of the nucleic acid; or a combination of any of these, are generated from the target nucleic acid. Fragments can vary in size, and suitable fragments are typically less that about 2000 nucleic acids. Suitable fragments can fall within several ranges of sizes including but not limited to: less than about 1000 bases, between about 100 to about 500 bases, from about 25 to about 200 bases, from about 3 to about 25 bases; or any combination of these sizes as further described herein. In some aspects, fragments of about one or two nucleotides are desirable.

Accordingly, contemplated herein is specific and predictable physical fragmentation of nucleic acids using for example any physical force that can break one or more particular chemical bonds, such that a specific and predictable fragmentation pattern is produced. Such physical forces include but are not limited to ionization radiation, such as X-rays, UV-rays, gamma-rays; dye-induced fragilization; chemical cleavage; or the like.

As used herein, a reference biomolecule refers to a biomolecule, which is generally, although not necessarily, to which a target biomolecule is compared. Thus, for example, a reference nucleic acid is a nucleic acid to which the target nucleic acid is compared in order to identify potential or actual sequence variations in the target nucleic acid relative to the reference nucleic acid. Reference nucleic acids typically are of known sequence or of a sequence that can be determined.

As used herein, transcription-based processes include "in vitro transcription system," which refers to a cell-free system containing an RNA polymerase and other factors and reagents necessary for transcription of a DNA molecule operably linked to a promoter that specifically binds an RNA polymerase. An in vitro transcription system can be a cell extract, for example, a eukaryotic cell extract. The term "transcription," as used herein, generally means the process by which the production of RNA molecules is initiated, elongated and terminated based on a DNA template. In addition, the process of "reverse transcription," which is well known in the art, is considered as encompassed within the meaning of the term "transcription" as used herein. Transcription is a polymerization reaction that is catalyzed by DNA-dependent or RNA-dependent RNA polymerases. Examples of RNA polymerases include the bacterial RNA polymerases, SP6 RNA polymerase, T3 RNA polymerase, T7 RNA polymerase, the mutant T7 or SP6 R&DNA™ polymerases that can incorporate dNTPs and modified dNTPs into transcripts (see, e.g., U.S. Pat. Nos. 5,849,546 and 6,107,037, incorporated herein by reference in their entirety).

The term "isolated" as used herein with respect to a nucleic acid, including DNA and RNA, refers to nucleic acid molecules that are substantially separated from other macromolecules normally associated with the nucleic acid in its natural state. An isolated nucleic acid molecule is substantially separated from the cellular material normally associated with it in a cell or, as relevant, can be substantially separated from bacterial or viral material; or from culture medium when produced by recombinant DNA techniques; or from chemical precursors or other chemicals when the nucleic acid is chemically synthesized. In general, an isolated nucleic acid molecule is at least about 50% enriched with respect to its natural state, and generally is about 70% to about 80% enriched, particularly about 90% or 95% or more. Preferably, an isolated nucleic acid constitutes at least about 50% of a sample containing the nucleic acid, and can be at least about 70% or 80% of the material in a sample, particularly at least about 90% to 95% or greater of the sample. An isolated nucleic acid can be a nucleic acid molecule that does not occur in nature and, therefore, is not found in a natural state.

As used herein, "structure" of the nucleic acid includes but is not limited to secondary structures due to non-Watson-Crick base pairing (see, e.g., Seela, F. and A. Kehne *Biochemistry* 26:2232-2238 (1987)) and structures, such as hairpins, loops and bubbles, formed by a combination of base-paired and non base-paired or mis-matched bases in a nucleic acid.

As used herein, epigenetic changes refer to variations in a target sequence relative to a reference sequence (e.g., a mutant sequence relative to the wild-type sequence) that are not dependent on changes in the identity of the natural bases (A, G, C, T/U) or the twenty natural amino acids. Such variations include, but are not limited to, e.g., differences in the presence of modified bases or methylated bases between a target nucleic acid sequence and a reference nucleic acid sequence. Epigenetic changes refer to mitotically and/or meiotically heritable changes in gene function or changes in higher order nucleic acid structure that cannot be explained by changes in nucleic acid sequence. Examples of systems that are subject to epigenetic variation or change include, but are not limited to, DNA methylation patterns in animals, histone modification and the Polycomb-trithorax group (Pc-G/tx) protein complexes. Epigenetic changes usually, although not necessarily, lead to changes in gene expression that are usually, although not necessarily, inheritable.

As used herein, a "primer" refers to an oligonucleotide that is suitable for hybridizing, chain extension, amplification and sequencing. Similarly, a probe is a primer used for hybridization. The primer refers to a nucleic acid that is of low enough mass, typically between about 5 and 200 nucleotides, generally about 70 nucleotides or less than 70, and of sufficient size to be conveniently used in the methods of amplification and methods of detection and sequencing provided herein. These primers include, but are not limited to, primers for detection and sequencing of nucleic acids, which require a sufficient number nucleotides to form a stable duplex, typically about 6-30 nucleotides, about 10-25 nucleotides and/or about 12-20 nucleotides. Thus, for purposes herein, a primer is a sequence of nucleotides contains of any suitable length, typically containing about 6-70 nucleotides, 12-70 nucleotides or greater than about 14 to an upper limit of about 70 nucleotides, depending upon sequence and application of the primer.

As used herein, reference to mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof. MALDI, particular UV and IR, are exemplary formats.

As used herein, the phrase "determining the mass signals of the fragments produced" refers to detecting the mass of the base specifically-fragmented fragments using any suitable mass detection format known to those of skill in the art, such as for example, mass spectrometry. Such formats include, but are not limited to, Matrix-Assisted Laser Desorption/Ionization, Time-of-Flight (MALDI-TOF), Electrospray ionization (ESi), IR-MALDI (see, e.g., published International PCT application No. 99/57318 and U.S. Pat. No. 5,118,937), Orthogonal-TOF (O-TOF), Axial-TOF (A-TOF), Ion Cyclotron Resonance (ICR), Fourier Transform, Linear/Reflectron (RETOF), Quadrupole mass spectrometry, Quadrupole ion trap mass spectrometry, and combinations thereof. See also, Aebersold and Mann, Mar. 13, 2003, *Nature* 422:198-207 (e.g., at FIG. 2); and Yates (1998) *J. of Mass Spec.* 33:1-19, for a review of exemplary methods for mass spectrometry suitable for use in the methods provided herein, which articles are incorporated herein in its entirety by reference. MALDI, particular UV and IR, and O-TOF are among the exemplary formats for mass spectrometry.

For example, O-TOF instruments possess a number of attributes inherent to their design which make them ideally suited for coupling liquid separation techniques to Atmospheric Pressure Ionization (API). The first attribute is the fast acquisition rates achieved by O-TOF. Acquisition rates on the order of 10's of milliseconds are not uncommon. Thus, narrow peaks (<1 second FWHM) associated with separation techniques such as capillary electrophoresis (CE) can be easily profiled. Along with fast scan rates, O-TOF mass spectrometers also has the ability to see a very broad mass range (e.g., 0-6000 Da/spectra). In addition, these instruments possess excellent sensitivity since all the ions entering the analyzer region are accelerated to the detector at high repetition rates (e.g., 5 kHz).

As used herein, mass spectrum refers to the presentation of data obtained from analyzing a biopolymer or fragment thereof by mass spectrometry either graphically or encoded numerically.

As used herein, pattern or fragmentation pattern or fragmentation spectrum with reference to a mass spectrum or mass spectrometric analyses, refers to a characteristic distribution and number of signals (such as peaks or digital representations thereof). In general, a fragmentation pattern as used herein refers to a set of fragments that are generated by specific cleavage of a biomolecule such as, but not limited to, nucleic acids and proteins.

As used herein, specific cleavage that is "DNA glycosylase-mediated" refers to the use of DNA glycosylase in combination with an endonuclease, such as AP-endonuclease, or the use of DNA glycosylase in combination with chemical or physical cleavage at abasic sites, as described herein. In addition, several methods exist where treatment of DNA with specific chemicals modifies existing bases so that they are recognized by specific DNA glycosylases. For example, treatment of DNA with alkylating agents such as methylnitrosourea generates several alkylated bases including N3-methyladenine and N3-methylguanine which are recognized and cleaved by alkyl purine DNA-glycosylase. Treatment of DNA with sodium bisulfite causes deamination of cytosine residues in DNA to form uracil residues in the DNA which can be cleaved by uracil N-glycosylase (also known as uracil DNA-glycosylase).

As used herein, signal, mass signal or output signal in the context of a mass spectrum or any other method that measures mass and analysis thereof refers to the output data, which is the number or relative number of molecules having a particular mass. Signals include "peaks" and digital representations thereof.

As used herein, the term "peaks" refers to prominent upward projections from a baseline signal of a mass spectrometer spectrum ("mass spectrum") which corresponds to the mass and intensity of a fragment. Peaks can be extracted from a mass spectrum by a manual or automated "peak finding" procedure.

As used herein, the mass of a peak in a mass spectrum refers to the mass computed by the "peak finding" procedure.

As used herein, the intensity of a peak in a mass spectrum refers to the intensity computed by the "peak finding" procedure that is dependent on parameters including, but not limited to, the height of the peak in the mass spectrum and its signal-to-noise ratio.

As used herein, "analysis" refers to the determination of certain properties of a single oligonucleotide or polypeptide, or of mixtures of oligonucleotides or polypeptides. These properties include, but are not limited to, the nucleotide or amino acid composition and complete sequence, the existence of single nucleotide polymorphisms and other mutations or sequence variations between more than one oligonucleotide or polypeptide, the masses and the lengths of oligonucleotides or polypeptides and the presence of a molecule or sequence within a molecule in a sample.

As used herein, "multiplexing" refers to the simultaneous determination of more than one oligonucleotide or polypeptide molecule, or the simultaneous analysis of more than one oligonucleotide or oligopeptide, in a single mass spectrometric or other mass measurement, i.e., a single mass spectrum or other method of reading sequence.

As used herein, amplifying refers to means for increasing the amount of a biopolymer, especially nucleic acids. Based on the 5' and 3' primers that are chosen, amplification also serves to restrict and define the region of the genome which is subject to analysis. Amplification can be by any means known to those skilled in the art, including use of the polymerase chain reaction (PCR), etc. Amplification, e.g., PCR must be done quantitatively when the frequency of polymorphism is required to be determined.

As used herein, "polymorphism" refers to the coexistence of more than one form of a gene or portion thereof. A portion of a gene of which there are at least two different forms, i.e., two different nucleotide sequences, is referred to as a "polymorphic region of a gene." A polymorphic region can be a single nucleotide, the identity of which differs in different alleles. A polymorphic region can also be several nucleotides in length. Thus, a polymorphism, e.g., genetic variation, refers to a variation in the sequence of a gene within a population, such as allelic variations and other variations that arise or are observed. A polymorphism refers to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested amongst members of a population. A single nucleotide polymorphism (SNP) refers to a polymorphism that arises as the result of a single base change, such as an insertion, deletion or change (substitution) in a base.

A polymorphic marker or site is the locus at which divergence occurs. Such site can be as small as one base pair (an SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

As used herein, "polymorphic gene" refers to a gene having at least one polymorphic region.

As used herein, "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has at least two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, "predominant allele" refers to an allele that is represented in the greatest frequency for a given population. The allele or alleles that are present in lesser frequency are referred to as allelic variants. As used herein, changes in a nucleic acid sequence known as mutations can result in proteins with altered or in some cases even lost biochemical activities; this in turn can cause genetic disease. Mutations include nucleotide deletions, insertions or alterations/substitutions (i.e. point mutations). Point mutations can be either "missense," resulting in a change in the amino acid sequence of a protein or "nonsense" coding for a stop codon and thereby leading to a truncated protein.

As used herein, a sequence variation contains one or more nucleotides or amino acids that are different in a target nucleic acid or protein sequence when compared to a reference nucleic acid or protein sequence. The sequence variation can include, but is not limited to, a mutation, a polymorphism, or sequence differences between a target sequence and a reference sequence that belong to different organisms. A sequence variation does in general, although not always, contain a subset of the complete set of nucleotide, amino acid, or other biopolymer monomeric unit differences between the target sequence and the reference sequence.

As used herein, "genotype" refers to the identity of the alleles present in an individual or sample. The term "genotyping" a sample or individual refers to determining a specific allele or specific nucleotide(s) carried by an individual at particular region(s).

As used herein, additional or missing peaks or signals are peaks or signals corresponding to fragments of a target sequence that are either present or absent, respectively, relative to fragments obtained by actual or simulated cleavage of a reference sequence, under the same cleavage reaction conditions. Besides missing or additional signals, differences between target fragments and reference fragments can be manifested as other differences including, but not limited to, differences in peak intensities (height, area, signal-to-noise or combinations thereof) of the signals.

As used herein, different fragments are fragments of a target sequence that are different relative to fragments obtained by actual or simulated cleavage of a reference sequence, under the same cleavage reaction conditions. Different fragments can be fragments that are missing in the target fragment pattern relative to a reference fragment pattern, or are additionally present in the target fragmentation pattern relative to the reference fragmentation pattern. Besides missing or additional fragments, different fragments can also be differences between the target fragmentation pattern and the reference fragmentation pattern that are qualitative including, but not limited to, differences that lead to differences in peak intensities (height, area, signal-to-noise or combinations thereof) of the signals corresponding to the different fragments.

As used herein, the term "compomer" refers to the composition of a sequence fragment in terms of its monomeric component units. For nucleic acids, compomer refers to the base composition of the fragment with the monomeric units being bases; the number of each type of base can be denoted by $B_n$ (i.e.: $A_a C_c G_g T_t$, with $A_O C_O G_O T_O$ representing an "empty" compomer or a compomer containing no bases). A natural compomer is a compomer for which all component monomeric units (e.g., bases for nucleic acids and amino acids for proteins) are greater than or equal to zero. For purposes of comparing sequences to determine sequence variations, however, in the methods provided herein, "unnatural" compomers containing negative numbers of monomeric units can be generated by the algorithm. For polypeptides, a compomer refers to the amino acid composition of a polypeptide fragment, with the number of each type of amino acid similarly denoted. A compomer corresponds to a sequence if the number and type of bases in the sequence can be added to obtain the composition of the compomer. For example, the compomer $A_2 G_3$ corresponds to the sequence AGGAG. In general, there is a unique compomer corresponding to a sequence, but more than one sequence can correspond to the same compomer. For example, the sequences AGGAG, AAGGG, GGAGA, etc. all correspond to the same compomer $A_2 G_3$, but for each of these sequences, the corresponding compomer is unique, i.e., $A_2 G_3$.

As used herein, witness compomers or compomer witnesses refer to all possible compomers whose masses differ by a value that is less than or equal to a sufficiently small mass difference from the actual mass of each different fragment generated in the target cleavage reaction relative to the same reference cleavage reaction. A sufficiently small mass difference can be determined empirically, if needed, and is generally the resolution of the mass measurement. For example, for mass spectrometry measurements, the value of the sufficiently small mass difference is a function of parameters including, but not limited to, the mass of the different fragment (as measured by its signal) corresponding to a witness compomer, peak separation between fragments whose masses differ by a single nucleotide in type or length, and the absolute resolution of the mass spectrometer. Cleavage reactions specific for one or more of the four nucleic acid bases (A, G, C, T or U for RNA, or modifications thereof) or of the twenty amino acids or modifications thereof, can be used to generate data sets containing the possible witness compomers for each different fragment such that the masses of the possible witness compomers near or equal the actual measured mass of each different fragment by a value that is less than or equal to a sufficiently small mass difference.

As used herein, two or more sequence variations of a target sequence relative to a reference sequence are said to interact with each other if the differences between the fragmentation pattern of the target sequence and the reference sequence for a specific cleavage reaction are not a simple sum of the differences representing each sequence variation in the target sequence. For sequence variations in the target sequence that do not interact with each other, the separation (distance) between sequence variations along the target sequence is sufficient for each sequence variation to generate a distinct different fragment (of the target sequence relative to the reference sequence) in a specific cleavage reaction, the differences in the fragmentation pattern of the target sequence relative to the reference sequence represents the sum of all sequence variations in the target sequence relative to the reference sequence.

As used herein, a sufficiently small mass difference is the maximum mass difference between the measured mass of an identified different fragment and the mass of a compomer, such that the compomer can be considered as a witness compomer for the identified different fragment. A sufficiently small mass difference can be determined empirically, if needed, and is generally the resolution of the mass measurement. For example, for mass spectrometry measurements, the value of the sufficiently small mass difference is a function of parameters including, but not limited to, the mass of the different fragment (as measured by its signal) corresponding to a witness compomer, the peak separation between fragments whose masses differ by a single nucleotide in type or length, and the absolute resolution of the mass spectrometer.

As used herein, a substring or subsequence s[i,j] denotes a cleavage fragment of the string s, which denotes the full length nucleic acid or protein sequence. As used herein, i and j are integers that denote the start and end positions of the substring. For example, for a nucleic acid substring, i and j can denote the base positions in the nucleic acid sequence where the substring begins and ends, respectively. As used herein, c[i,j] refers to a compomer corresponding to s[i,j].

As used herein, sequence variation order k refers to the sequence variation candidates of the target sequence constructed by the techniques provided herein, where the sequence variation candidates contain at most k mutations, polymorphisms, or other sequence variations, including, but not limited to, sequence variations between organisms, insertions, deletions and substitutions, in the target sequence relative to a reference sequence. The value of k is dependent on a number of parameters including, but not limited to, the expected type and number of sequence variations between a reference sequence and the target sequence, e.g., whether the sequence variation is a single base or multiple bases, whether sequence variations are present at one location or at more than one location on the target sequence relative to the reference sequence, or whether the sequence variations interact or do not interact with each in the target sequence. For example, for the detection of SNPs, the value of k is usually, although not necessarily, 1 or 2. As another example, for the detection of mutations and in resequencing, the value of k is usually, although not necessarily, 3 or higher.

As used herein, given a specific cleavage reaction of a base, amino acid, or other feature X recognized by the cleavage reagent in a string s, then the boundary b[i,j] of the substring s[i,j] or the corresponding compomer c[i,j] refers to a set of markers indicating whether cleavage of string s does not take place immediately outside the substring s[i,j]. Possible markers are L, indicating whether "s is not cleaved directly before i", and R, indicating whether "s is not cleaved directly after j". Thus, b[i,j] is a subset of the set {L,R} that contains L if and only if X is present at position i−1 of the string s, and contains R if and only if X is present at position j+1 of the string s. #b denotes the number of elements in the set b, which can be 0, 1, or 2, depending on whether the substring s[i,j] is specifically cleaved at both immediately flanking positions (i.e., at positions i−1 and j+1), at one immediately flanking position (i.e., at either position i−1 or j+1) or at no immediately flanking position (i.e., at neither position i−1 nor j+1).

As used herein, a compomer boundary or boundary b is a subset of the set {L,R} as defined above for b[i,j]. Possible values for b are the empty set { }, i.e., the number of elements in b (#b) is 0; {L}, {R}, i.e., #b is 1; and {L,R}, i.e., #b is 2.

As used herein, bounded compomers refers to the set of all compomers c that correspond to the set of subsequences of a reference sequence, with a boundary that indicates whether or not cleavage sites are present at the two ends of each subsequence. The set of bounded compomers can be compared against possible compomer witnesses to construct all possible sequence variations of a target sequence relative to a reference sequence. For example, (c,b) refers to a 'bounded compomer' that contains a compomer c and a boundary b.

As used herein, C refers to the set of all bounded compomers within the string s; i.e., for all possible substrings s[i,j], find the bounded compomers (c[i,j],b[i,j]) and these will belong to the set C. C can be represented as C:={(c[i,j], b[i,j]): 1≤i≤j≤length of s}.

As used herein, ord[i,j] refers to the number of times substring s[i,j] will be cleaved in a particular cleavage reaction.

As used herein, given compomers c,c' corresponding to fragments f,f', d(c,c') is a function that determines the minimum number of sequence variations, polymorphisms or mutations (insertions, deletions, substitutions) that are needed to convert c to c', taken over all potential fragments f,f' corresponding to compomers c,c', where c is a compomer of a fragment s of the reference biomolecule and c' is the compomer of a fragment s' of the target biomolecule resulting from a sequence variation of the s fragment. As used herein, d(c,c') is equivalent to d(c',c).

For a bounded compomer (c,b) constructed from the set C, The function D(c',c,b) measures the minimum number of sequence variations relative to a reference sequence that is needed to generate the compomer witness c'. D(c',c,b) can be represented as D(c',c,b):=d(c',c)+#b. As used herein, D(c',c,b) is equivalent to D(c,c',b).

As used herein, $C_k$ is a subset of C such that compomers for substrings containing more than k number of sequence variations of the cut string will be excluded from the set C. Thus, if there is a sequence variation containing at most k insertions, deletions, and substitutions, and if c' is a compomer corresponding to a peak witness of this sequence variation, then there exists a bounded compomer (c,b) in $C_k$ such that D(c', c,b)≤k. $C_k$ can be represented as $C_k$:={(c[i,j], b[i,j]): 1≤i≤j≤length of s, and ord[i,j]+#b[i,j]≤k} The algorithm provided herein is based on this reduced set of compomers corresponding to possible sequence variations. As used herein, $L_\Delta$ or L_Δ denotes a list of peaks or signals corresponding to fragments that are different in a target cleavage reaction relative to the same reference cleavage reaction. The differences include, but are not limited to, signals that are present or absent in the target fragment signals relative to the reference fragment signals, and signals that differ in intensity between the target fragment signals and the reference fragment signals.

As used herein, sequence variation candidate refers to a potential sequence of the target sequence containing one or more sequence variations. The probability of a sequence variation candidate being the actual sequence of the target biomolecule containing one or more sequence variations is measured by a score.

As used herein, a reduced set of sequence variation candidates refers to a subset of all possible sequence variations in the target sequence that generate a given set of fragments upon specific cleavage of the target sequence. A reduced set of sequence variation candidates can be obtained by creating, from the set of all possible sequence variations of a target sequence that can generate a particular fragmentation pattern (as detected by measuring the masses of the fragments) in a particular specific cleavage reaction, a subset containing only those sequence variations that generate fragments of the target sequence that are different from the fragments generated by actual or simulated cleavage of a reference sequence in the same specific cleavage reaction.

As used herein, fragments that are consistent with a particular sequence variation in a target molecule refer to those different fragments that are obtained by cleavage of a target molecule in more than one reaction using more than one cleavage reagent whose characteristics, including, but not limited to, mass, intensity or signal-to-noise ratio, when analyzed according to the methods provided herein, indicate the presence of the same sequence variation in the target molecule.

As used herein, scoring or a score refers to a calculation of the probability that a particular sequence variation candidate is actually present in the target nucleic acid or protein sequence. The value of a score is used to determine the sequence variation candidate that corresponds to the actual target sequence. Usually, in a set of samples of target sequences, the highest score represents the most likely sequence variation in the target molecule, but other rules for selection can also be used, such as detecting a positive score, when a single target sequence is present.

As used herein, simulation (or simulating) refers to the calculation of a fragmentation pattern based on the sequence of a nucleic acid or protein and the predicted cleavage sites in the nucleic acid or protein sequence for a particular specific cleavage reagent. The fragmentation pattern can be simulated as a table of numbers (for example, as a list of peaks corresponding to the mass signals of fragments of a reference biomolecule), as a mass spectrum, as a pattern of bands on a gel, or as a representation of any technique that measures mass distribution. Simulations can be performed in most instances by a computer program.

As used herein, simulating cleavage refers to an in silico process in which a target molecule or a reference molecule is virtually cleaved.

As used herein, in silico refers to research and experiments performed using a computer. In silico methods include, but are not limited to, molecular modelling studies, biomolecular docking experiments, and virtual representations of molecular structures and/or processes, such as molecular interactions.

As used herein, a subject includes, but is not limited to, animals, plants, bacteria, viruses, parasites and any other organism or entity that has nucleic acid. Among subjects are mammals, including humans. A patient refers to a subject afflicted with a disease or disorder.

As used herein, a phenotype refers to a set of parameters that includes any distinguishable trait of an organism. A phenotype can be physical traits and can be, in instances in which the subject is an animal, a mental trait, such as emotional traits.

As used herein, "assignment" refers to a determination that the position of a nucleic acid or protein fragment indicates a particular molecular weight and a particular terminal nucleotide or amino acid.

As used herein, "a" refers to one or more.

As used herein, "plurality" refers to two or more polynucleotides or polypeptides, each of which has a different sequence. Such a difference can be due to a naturally occurring variation among the sequences, for example, to an allelic variation in a nucleotide or an encoded amino acid, or can be due to the introduction of particular modifications into various sequences, for example, the differential incorporation of mass modified nucleotides into each nucleic acid or protein in a plurality.

As used herein, an array refers to a pattern produced by three or more items, such as three or more loci on a solid support.

As used herein, "unambiguous" refers to the unique assignment of peaks or signals corresponding to a particular sequence variation, such as a mutation, in a target molecule and, in the event that a number of molecules or mutations are multiplexed, that the peaks representing a particular sequence variation can be uniquely assigned to each mutation or each molecule.

As used herein, a data processing routine refers to a process, that can be embodied in software, that determines the biological significance of acquired data (i.e., the ultimate results of the assay). For example, the data processing routine can make a genotype determination based upon the data collected. In the systems and methods herein, the data processing routine also controls the instrument and/or the data collection routine based upon the results determined. The data processing routine and the data collection routines are integrated and provide feedback to operate the data acquisition by the instrument, and hence provide the assay-based judging methods provided herein.

As used herein, a plurality of genes includes at least two, five, 10, 25, 50, 100, 250, 500, 1000, 2,500, 5,000, 10,000, 100,000, 1,000,000 or more genes. A plurality of genes can include complete or partial genomes of an organism or even a plurality thereof. Selecting the organism type determines the genome from among which the gene regulatory regions are selected. Exemplary organisms for gene screening include animals, such as mammals, including human and rodent, such as mouse, insects, yeast, bacteria, parasites, and plants.

As used herein, "specifically hybridizes" refers to hybridization of a probe or primer only to a target sequence preferentially to a non-target sequence. Those of skill in the art are familiar with parameters that affect hybridization; such as temperature, probe or primer length and composition, buffer composition and salt concentration and can readily adjust these parameters to achieve specific hybridization of a nucleic acid to a target sequence.

As used herein, "sample" refers to a composition containing a material to be detected. In one embodiment, the sample is a "biological sample." The term "biological sample" refers to any material obtained from a living source, for example, an animal such as a human or other mammal, a plant, a bacterium, a fungus, a protist or a virus or a sample from such source that has been processed, such as by purification, amplification or other modification. The biological sample can be in any form, including a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, urine, cerebral spinal fluid and synovial fluid and organs. Preferably solid materials are mixed with a fluid. In particular, herein, the sample refers to a mixture of matrix used for mass spectrometric analyses and biological material such as nucleic acids. Derived from means that the sample can be processed, such as by purification or isolation and/or amplification of nucleic acid molecules.

As used herein, a composition refers to any mixture. It can be a solution, a suspension, liquid, powder, a paste, aqueous, non-aqueous or any combination thereof.

As used herein, a combination refers to any association between two or among more items.

As used herein, the term "1¼-cutter" refers to a restriction enzyme that recognizes and cleaves a 2 base stretch in the nucleic acid, in which the identity of one base position is fixed and the identity of the other base position is any three of the four naturally occurring bases.

As used herein, the term "1½-cutter" refers to a restriction enzyme that recognizes and cleaves a 2 base stretch in the nucleic acid, in which the identity of one base position is fixed and the identity of the other base position is any two out of the four naturally occurring bases.

As used herein, the term "2 cutter" refers to a restriction enzyme that recognizes and cleaves a specific nucleic acid site that is 2 bases long.

As used herein, the term "amplicon" refers to a region of DNA that can be replicated.

As used herein, the term "complete cleavage" or "total cleavage" refers to a cleavage reaction in which all the cleavage sites recognized by a particular cleavage reagent are cut to completion.

As used herein, the term "false positives" refers to mass signals that are from background noise and not generated by specific actual or simulated cleavage of a nucleic acid or protein.

As used herein, the term "false negatives" refers to actual mass signals that are missing from an actual fragmentation spectrum but can be detected in the corresponding simulated spectrum.

As used herein, the term "partial cleavage" refers to a reaction in which only a fraction of the cleavage sites of a particular cleavage reagent are actually cut by the cleavage reagent.

As used herein, cleave means any manner in which a nucleic acid or protein molecule is cut into smaller pieces. The cleavage recognition sites can be one, two or more bases long. The cleavage means include physical cleavage, enzymatic cleavage, chemical cleavage and any other way smaller pieces of a nucleic acid are produced.

As used herein, cleavage conditions or cleavage reaction conditions refers to the set of one or more cleavage reagents that are used to perform actual or simulated cleavage reactions, and other parameters of the reactions including, but not limited to, time, temperature, pH, or choice of buffer.

As used herein, uncleaved cleavage sites means cleavage sites that are known recognition sites for a cleavage reagent but that are not cut by the cleavage reagent under the conditions of the reaction, e.g., time, temperature, or modifications of the bases at the cleavage recognition sites to prevent cleavage by the reagent.

As used herein, complementary cleavage reactions refers to cleavage reactions that are carried out or simulated on the same target or reference nucleic acid or protein using different cleavage reagents or by altering the cleavage specificity of the same cleavage reagent such that alternate cleavage patterns of the same target or reference nucleic acid or protein are generated.

As used herein, a combination refers to any association between two or among more items or elements.

As used herein, a composition refers to any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, a kit is combination in which components are packaged optionally with instructions for use and/or reagents and apparatus for use with the combination.

As used herein, a system refers to the combination of elements with software and any other elements for controlling and directing methods provided herein.

As used herein, software refers to computer readable program instructions that, when executed by a computer, performs computer operations. Typically, software is provided on a program product containing program instructions recorded on a computer readable medium, such as but not limited to, magnetic media including floppy disks, hard disks, and magnetic tape; and optical media including CD-ROM discs, DVD discs, magneto-optical discs, and other such media on which the program instructions can be recorded.

B. METHODS OF OBTAINING ALLELE-SPECIFIC TARGET NUCLEIC ACIDS

Provided herein are methods for sequence variation analysis, comprising:
 a) modifying a mixture of nucleic acids to obtain a target nucleic acid sequence corresponding to a single or specific allele;
 b) fragmenting the target nucleic acid sequence, or a nucleic acid product transcribed from the target nucleic acid sequence of step a), at a plurality of specific and predictable sites;
 c) fragmenting or simulating fragmentation of a reference target nucleic acid into fragments at the same plurality of specific and predictable sites of step b); and
 d) genotyping the nucleic acid sequence corresponding to a single or specific allele at one or more loci. The sequence variation analysis can be selected from genotyping, haplotyping, HLA-typing or re-sequencing.

For these methods provided herein that employ the base-specific fragmentation methods that use mass spectrometry analysis set forth herein (e.g., MassCLEAVE™ assay) of sequence variation analysis (e.g., genotyping and/or haplotyping), any method of obtaining an allele-specific target nucleic acid, including the NEER-ASPCR method provided herein, is suitable so long as the method predominantly generates a specific allele. An allele is considered specifically obtained when it is present in the amplification mixture at a ratio of at least about 75:25 (e.g., ≥75%) relative to the undesired (e.g., unwanted) allele. Accordingly, in particular embodiments, the allele-specificity has a specificity of an amount selected from greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% (e.g., 99:1), 99.1%, 99.2%, 99.3%, 99.4%, 99.5%, 99.6%, 99.7%, 99.8%, 99.9% (e.g., 999:1) or higher of the desired allele relative to the undesired allele.

As used herein, the phrase "modifying a mixture of nucleic acids to obtain a target nucleic acid sequence corresponding to a single or specific allele" refers to any known method for obtaining a specific allele from a nucleic acid mixture, such as a genomic DNA sample, RNA or cDNA. In one embodiment herein, the modifying a mixture of nucleic acids is conducted by amplifying a target nucleic acid to obtain a specific allele. Exemplary methods include well-known amplification methods, such as Allele-Specific PCR, amplification by dilution, and the like. Other methods for obtaining a specific allele include the allele-selective amplification methods set forth herein in Sections B.2-B.5. Another method of obtaining a single or specific allele is the M1-PCR method that uses single-molecule dilution of genomic DNA for the separation of two homologous genomic DNAs for subsequent sequence variation analysis (see, e.g., Ding and Cantor, *Proc. Natl. Acad. Sci. USA* 100(13):7449-7453 (2003), incorporated herein by reference in its entirety). In particular embodiments, the leakage reduced NEER-ASPCR methods provided herein (described in Section B.1.a) are used to amplify and obtain the desired allele-specific target nucleic acid for subsequent genotyping.

For example, in one embodiment when the base-specific fragmentation method set forth in steps b)-d) above are used for genotyping and/or haplotyping, the NEER-ASPCR method set forth herein in Section B.1.a, is used to modify the mixture of nucleic acids to obtain the desired allele-specific template nucleic acid.

In another embodiment when the base-specific fragmentation method set forth in steps b)-d) above are used for genotyping and/or haplotyping, the well-known ARMS method set forth in EP 332,435 that adds a deliberate mismatch at the penultimate base of the allele-specific amplification primer is used to modify the mixture of nucleic acids to obtain the desired allele-specific template nucleic acid.

In yet another embodiment when the base-specific fragmentation method set forth in steps b)-d) above are used for genotyping and/or haplotyping, the combination of NEER-ASPCR and the well-known ARMS method set forth in EP 332,435 is used to modify the mixture of nucleic acids to obtain an allele-specific template nucleic acid.

In another embodiment when the base-specific fragmentation method set forth in steps b)-d) above are used for genotyping and/or haplotyping, a competitor oligonucleotide that is only required to be non-extendable (NE-ASPCR) is used to modify the mixture of nucleic acids to obtain an allele-specific template nucleic acid.

In yet another embodiment when the base-specific fragmentation method set forth in steps b)-d) above are used for genotyping and/or haplotyping, the combination of NE-ASPCR and the well-known ARMS method set forth in EP 332,435 is used to modify the mixture of nucleic acids to obtain an allele-specific template nucleic acid.

Typically, after an allele-specific template nucleic acid has been obtained in step a), the template nucleic acid is transcribed with particular nucleotides to facilitate the fragmentation of the transcribed template at specific and predictable sites (e.g., base-specific fragmentation). See, for example, Section C. herein titled "Methods of Generating Nucleic Acid Fragments" and Example 1.B. and 1.C. The allele-specific fragments are then analyzed for sequence variations compared to a reference sequence to facilitate genotyping and/or haplotyping using the methods and algorithms set forth in Section E. hereinafter.

B.1. Amplification of Target

B.1.a) Non-Extendable Exonuclease Resistant Allele-Specific PCR (NEER-AS-PCR)

Provided herein are methods for allele specific amplification that substantially reduces allele leakage, referred to herein as Non-extendable Exonuclease Resistant Allele-Specific PCR (NEER-ASPCR)(see FIG. 1). In the NEER-AS-PCR amplification methods, three oligonucleotides are designed as follows: the first oligonucleotide is designed to anneal at the selected allele discriminating polymorphism (e.g., a SNP) and amplify the desired allele (allele-specific amplification primer; also referred to herein as the forward primer); the second oligonucleotide is designed to compete with the first amplification primer for the non-desired allele (NEER competitor oligo), such that essentially only the desired allele is amplified without any leakage of the non-desired allele; and the third oligonucleotide is a reverse primer to the allele-specific forward amplification primer, which typically contains a DNA or RNA promoter region (e.g., a T7 promoter) attached to the 5' end for rendering the amplified target sequence amenable to DNA or RNA transcription. The last base at the 3'end of the allele-specific amplification primer should be complementary to the desired allele. Accordingly, the Non-extendable Exonuclease Resistant Allele-Specific PCR (NEER-ASPCR) method comprises contacting a target sequence with a forward allele-specific amplification primer, a NEER competitor oligonucleotide, and a reverse primer.

Also provided herein are methods of obtaining a nucleic acid genotype or haplotype, comprising:

amplifying a target nucleic acid in the presence of a competitor oligonucleotide that is non-extendable and is exonuclease resistant (an NEER competitor oligo); and genotyping the target nucleic acid. When this particular NEER-ASPCR method is used for modifying a mixture of nucleic acids to obtain an allele-specific template nucleic acid (e.g., to amplify a specific allele), any of the known methods for genotyping can be employed including but not limited to a primer oligo base extension assays, such as the homogeneous MassEXTEND™ reaction, Sequenom, San Diego, Calif.) and base-specific fragmentation methods (e.g., hMassCLEAVE™ assay) set forth herein. Accordingly, in one embodiment, when the NEER-ASPCR method is used to obtain the allele-specific template nucleic acid, the base-specific fragmentation method that uses mass spectrometry analysis set forth herein (and in U.S. application Ser. No. 60/429,895, which is incorporated herein by reference in its entirety) is employed to genotype and/or haplotype the allele-specific target nucleic acids. In another embodiment, when the NEER-ASPCR method is used, the primer mass extension methodology (MassEXTEND™ reaction, also referred to as PROBE in U.S. Pat. Nos. 6,428,955 and 6,258,538; which are incorporated herein by reference in its entirety) is employed to genotype and/or haplotype the allele-specific target nucleic acids.

In the NEER-ASPCR methods provided herein, the amplification step is conducted in the presence of a competitor oligonucleotide that is non-extendable. As used herein, a "competitor oligonucleotide that is non-extendable" refers to an oligonucleotide designed to hybridize to the non-desired allele, such that upon binding primer extension of that allele does not occur. The competitive primers employed herein can comprise any sequence so long as they are rendered non-extendable by any means known in the art. Numerous methods for rendering an oligonucleotide primer resistant to extension (i.e., non-extendable) in an amplification reaction are well known in the art, and include the placement of modified nucleotides within the primer sequence. In a particular embodiment, the competitor oligonucleotide is non-extendable by a polymerase that is used to extend and amplify the desired allele. In this embodiment, the competitor oligonucleotide can have a modified nucleotide at its 3'-end. Exemplary modified nucleotides contemplated herein to provide non-extendable function include, but are not limited to, an inverted base, a dideoxynucleotide, a ribonucleotide, a 3' Phosphate ($PO_4$), a carbon chain spacer (e.g., C-3 (propyl), C-5, C-7, C-9 or C-12 spacers; available from Trilink Biotechnologies, San Diego, Calif.; and see Schmidt et al., *NAR*, 24(4):573-581 (1996)) or a peptide nucleic acid (PNA).

At this stage, the competitor oligo only has the non-extendable feature and is referred to herein as an NE-competitor oligonucleotide that can be used in NE-ASPCR methods, such as those described in the preceding section where the base-specific fragmentation methods in combination with mass spectrometry analysis set forth herein are used for genotyping and/or haplotyping.

In other embodiments (such as for the long range PCR methods provided herein, and the like), the non-extendable competitor oligonucleotide primers employed herein can comprise any sequence so long as the competitor oligonucleotide is further rendered exonuclease resistant by any means known in the art. Thus, in the NEER-ASPCR methods provided herein, the amplification step is conducted in the presence of a competitor oligonucleotide that is non-extendable and exonuclease resistant. The term "exonuclease resistant" in the context of oligonucleotides refers to an oligonucleotide that cannot be degraded by the proofreading enzymatic activity of DNA polymerases. Suitable methods for rendering the competing primers exonuclease resistant are well-known in the art and include modifying the 3' nucleotide, such as by using an inverted base, a dideoxynucleotide (ddNTP) with a phosphorothioate or methylphosphonate bound, a multiple carbon chain spacer, such as a C3 (3 carbon propyl) spacer, a C9 spacer, a C12 spacer, and the like; which are well-known in the art and can be obtained from Trilink Biotechnologies (San Diego, Calif.), and the like. Typically, dideoxynucleotides are non-extendable but not exonuclease resistant, unless linked to the previous nucleotide via a cleavage resistant linkage, such as a phosphorothioate link (Stein et al., NAR, 16(8):3209-3221, 1988, incorporated herein by reference in its entirety) or a methylphosphonate link (Reynolds et al., NAR, 24(22):4584-4591, 1996; and Furdon et al., NAR, 17(22):9193-9204, 1989, each of which are incorporated herein by reference in their entirety). Thus, the modified 3'-end nucleotide of a NEER competitor oligonucleotide can be bound to the previous nucleotide via a phosphorothioate or methylphosphonate link.

In other embodiments, the allele discrimination can be improved by adding a deliberate mismatch at the penultimate base of the allele-specific amplification primer, as set forth in the ARMS technique (Cellmark Diagnostics, European Patent No. 0332435 (ZENECA). In other embodiments, the NEER competitor oligo is non-extendable and preferentially exonuclease resistant in order to perform long range amplifications using exonuclease-activity containing polymerases.

For the amplification reaction, the NEER competitor can be added to the amplification reaction in an amount ranging from about 1-fold up to about 25-fold or more excess of NEER competitor to the concentration of AS-PCR amplification primers. In a particular embodiment, the use of 10-fold to 20-fold fold excess of NEER competitor oligonucleotide to the concentration of AS-PCR primers is suitable for SNP detection. Also contemplated herein are embodiments where the NEER competitor is added to the amplification reaction in an excess amount over the concentration of AS-PCR amplification primer selected from: 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold or 75-fold or more. The NEER-ASPCR methods provided herein result in an allele-specificity in an amount selected from greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% (e.g., 99:1), 99.1%, 99.2%, 99.3%, 99.4%, 99.5%, 99.6%, 99.7%, 99.8%, 99.9% (e.g., 999:1) or higher of the desired allele.

In the NEER-ASPCR methods provided herein, the amplification step is conducted in the presence of a second oligonucleotide that typically comprises a promoter sequence (e.g., T7 promoter), where the second oligo corresponds to the reverse primer of the forward AS-PCR amplification primer. Exemplary promoters contemplated for use herein are well known in the art and include the T7 promoter, SP6 promoter, and the T3 promoter. In one embodiment, the promoter sequence is a polymerase promoter sequence, wherein the polymerase is either a DNA or RNA polymerase. In another embodiment, the amplification is performed in the presence of a thermostable DNA polymerase, or a mixture of thermostable DNA polymerases, having exonuclease activity. In a particular embodiment of the NEER-ASPCR methods provided herein, the amplification is performed in the presence of Taq DNA polymerase and an enzyme having exonuclease function.

The use of DNA polymerases having exonuclease activity or the use of a DNA polymerase in combination with an enzyme having exonuclease function permits long-range PCR amplification reactions to occur.

Long Range

It is known that a constraint exists on the maximum size of fragments that can be amplified using DNA polymerase in standard PCR amplification reactions. For genomic DNA, the maximum size is about 3-5 kb, whereas for phage lambda DNA PCR amplifications of up to 15 kb have been achieved. The basis for this constraint on the maximum size of a fragment that can be amplified is the rate of errors of misincorporation of Taq DNA polymerase, which have been shown to be $2\times10^{-4}$ to $2\times10^{-5}$ mutations per nucleotide per cycle. Incorporation of a mismatched base causes strand extension to stall and the Taq DNA polymerase to dissociate from the template strand. The longer the PCR product, the more likely misincorporation is to occur.

To effectively amplify products over about 5-10 kb using PCR, the methods provided herein use particular combinations of thermostable DNA polymerases having different activities. As used herein, the phrase "in the presence of a thermostable DNA polymerase, or a mixture of thermostable DNA polymerases, having exonuclease activity" generally refers to a blend containing a DNA Polymerase (e.g., Taq) in combination with another thermostable enzyme possessing proofreading activity (e.g., 3' to 5' exonuclease activity), wherein the blend allows for successful amplification of longer PCR products (Barnes, *Proc. Natl. Acad. Sci USA* 91:2216-2220 (1994), incorporated herein by reference in its entirety). Exemplary enzymes suitable for use herein that possess the exonuclease proofreading activity include Pfu, Vent, Deep Vent (see, e.g., Barnes, *Proc. Natl. Acad. Sci. USA* 91:2216-2220 (1994), incorporated herein by reference in its entirety); and Pwo and Tgo (available from Roche Molecular Biochemicals). Also contemplated herein are several other combinations of proofreading enzymes and non-proofreading DNA polymerase enzymes (other than Taq) that can be used to achieve optimal overall processivity and fidelity. Exemplary non-proofreading DNA polymerase enzymes contemplated for use herein include Taq DNA polymerase, Klentaq1, Amplitaq, Klentaq5 (DeltaTaq, available from United States Biochemical), Stoffel Fragment. Particular combinations of DNA polymerases having exonuclease$^-$/exonuclease$^+$ activity contemplated for use herein include Taq/Pfu, Taq/Deep Vent, Taq/Vent, Taq/Pwo, Taq/Tgo, Klentaq1/Pfu, Klentaq1/Deep Vent, Klentaq1/Vent, Klentaq1/Pwo, Klentaq1/Tgo, and so on. Also contemplated herein is the use of any combinations of 1, 2, 3 or more exonuclease$^-$ DNA polymerases with 1, 2, 3 or more exonuclease$^+$ DNA polymerases.

Using a blend of DNA polymerases that contain exonuclease activity to perform long-range allele-specific PCR is typically risky. In the presence of one of those proofreading enzymes, the last base of the allele-specific primer is often cleaved when annealed to the unwanted allele. Following cleavage of the essential allele-discriminatory base, the primer loses its specificity and the unwanted allele can be amplified. To overcome this effect, the NEER competitor oligonucleotide (non-extendable and exonuclease resistant oligonucleotide) having a nuclease resistant allele-discriminatory base (NEER competitor) is used in the particular allele-specific amplification methods provided herein. The NEER competitor oligo is used in excess and has a higher affinity for annealing to the unwanted allele compared to the allele-specific PCR primers. As a result of the NEER competitor oligo outcompeting the Allele-Specific PCR primer for the undesired allele, the AS-PCR primer is then forced to prime extension from the desired allele only. Accordingly, the use of NEER competitor in performing long-range AS-PCR, advantageously provides added specificity when using proofreading containing enzyme blends for long-range PCR amplification.

The long-range AS-PCR amplification methods provided herein take advantage of the use of proofreading polymerases to accurately amplify nucleic acid regions of 3,000, 4,000, 5,000, 10,000, 15,000, 20,000, 25,000, 30,000, 35,000, 40,000, 45,000, 50,000 base pairs or more. For example, in a particular embodiment for achieving long-range amplification, a combination of Taq polymerase and Pfu1 enzyme is used in the amplification reaction. This combination of enzymes contains a proofreading function that ultimately results in the high-fidelity amplification of a relatively large region of nucleic acid, such as genomic DNA in sizes up to about 5 kb or more, up to 10 kb or more, up to 15 kb or more, 20 kb or more, 25 kb or more, 30 kb or more, 35 kb or more, 40 kb or more, 45 kb or more, 50 kb or more.

Although any of the well-known methods for genotyping or haplotyping a sample are contemplated for use herein with the NEER-ASPCR methods provided herein, in a particular embodiment, the genotyping step is conducted using base-specific fragmentation methodology in combination with mass spectrometry analysis (e.g., MassCLEAVE™ assay) set forth herein and in related U.S. application Ser. No. 60/429, 895, which is incorporated herein by reference in its entirety. Accordingly, in one embodiment, the specific and predictable fragmentation is base-specific fragmentation and the genotyping step can further comprise mass spectrometric analysis.

B.2. Other Allele Selective Amplification Methods

Other allele-specific methods of amplification are well-known in the art and include, among others, those set forth hereinbelow. Exemplary methods of obtaining allele-specific targets include but are not limited to the ARMS method disclosed in European Patent No. 0332435.

Another method for obtaining allele specific PCR products entails using modified primers, such that the basis for achieving allele specific amplification is the formation of a duplex or secondary structure. In this method, the formation of a duplex or secondary structure involves base pairing between (i) nucleotides at or near the 3' end of a strand (said nucleotides being at least partially templated by a primer for the complementary strand) and (ii) nucleotides of the same strand that lie further interior from the 3' end and include (crucially) a polymorphic site (or sites). The results of this method are that: (i) the secondary structure is formed to a different extent in the two alleles (ideally the secondary structure is formed in a completely allele-specific manner), and (ii) the secondary structure at least partially inhibits primer binding and/or primer extension, and consequently inhibits amplification of the strand with the secondary structure at the 3' end (see, e.g., U.S. Pat. No. 6,475,736B1). The point of the primer modification, then, is to produce a template for polymerization on the complementary strand leading to a sequence that forms a secondary structure that inhibits further primer binding/extension from that end. The modification in the primer can be introduced either at the 5' end or internally, but not at the 3' end of the primer. An example of this method applied to haplotyping the ApoE gene is provided in FIGS. 14-17 of U.S. Pat. No. 6,475,736 and illustrate some of the types of secondary structure that can be produced to inhibit primer binding/extension.

One implementation of this particular method entails introducing a 5' extension in a primer. After a complementary strand is extended across that primer, and then separated by a cycle of denaturation, the complementary strand forms a hairpin loop structure in one allele but not the other. Specifically, the free 3' end of the complementary strand anneals to an upstream segment of the same strand that includes the polymorphic site, such that the polymorphic site participates in the stem of the loop. If the polymorphic nucleotide is complementary to the nucleotide near the 3' end of the strand a tight stem is formed. If not, then a lower affinity interaction exists and, at appropriately selected conditions, the stem is not formed. Since the formation of the stem makes the 3' end of the strand no longer available for binding free primer, the amplification of the strand in which a perfect stem is formed is inhibited. The length of the 5' extension on the primer can be varied, depending on the desired size of the loop, or on whether it is desirable to form alternative structures or enzyme recognition sites.

Some of the alternative structures that are useful include: (i) recognition sites for various DNA modifying enzymes such as restriction endonucleases, (ii) a cruciform DNA structure, that can be very stable, or can be recognized by enzymes such as bacteriophage resolvases (e.g., T4E7, T7E1), or (iii) recognition sites for DNA binding proteins (such as from thermophilic organisms) such as zinc finger proteins, catalytically inactive endonucleases, or transcription factors. The purpose of inducing such structures in an allele-specific manner is to effect allele-specific binding to, or modification of, DNA. For example, a duplex can be formed only (or preferentially) by a strand from one allele that contains the recognition sequence for a thermostable restriction enzyme such as Taq I. Allele-specific strand cleavage can be achieved by inclusion of (thermostable) Taq I during the PCR, resulting in complete inactivation of each cleaved template molecule and thereby leading to allele selective amplification. In this embodiment, one requirement is that there are no Taq I sites elsewhere in the PCR amplicon; another requirement is that one of the two alleles contains a Taq I recognition sequence. The first requirement can limit the length of amplicons that can be allele specifically modified, for example, when frequently cutting restriction enzymes are used. The second requirement limits the use of this method to instances in which polymorphisms occur in restriction endonuclease recognition sites. These requirements can be addressed in part by including a 5' primer extension, along with an internal primer loop, to form a recognition sequence formed by the internal loop that is the site for a rare cutting restriction endonuclease, where the recognition site (i) is an interrupted palindrome, or (ii) cleaves at some distance from its recognition sequence; this construction can facilitate cleavage of the polymorphic nucleotide when (i) the other end of the interrupted palindrome, or (ii) the cleavage site for the restriction enzyme, occurs at the polymorphic nucleotide, and is therefore sensitive to whether there is a duplex or a (partially or completely) single-stranded region at the polymorphic site. Methods of using extrinsic nucleotides in primers to create a cleavage site in a polymorphic nucleotide are known in the art, as illustrated in U.S. Pat. No. 6,475,736. Exemplary enzymes for PCR implementation of these methods include enzymes from thermophiles, such as Bsl I (CCNNNNN/NNGG) and Mwo I (GCNNNNN/NNGC). Alternative methods entail placing the stem-forming nucleotides internally, rather than at the end of the primer.

The experiments described above are directed to stem formation during PCR, which requires that the stem be stable at an annealing temperature of about 50° C. or greater. Isothermal amplification methods, such as 3SR and others, can also be used to achieve allele-specific amplification. For isothermal amplification methods the loop forming sequences are designed differently, to achieve maximum allele discrimination in secondary structure formation at 37° C., 42° C. or other temperatures suited to amplification. This can be achieved by shortening the length of duplex regions. Shorter duplex lengths can be tested empirically for isothermal amplification methods. This particular method does not address the intrinsic limitations of all PCR-based methods, but does provide superior performance compared to other procedures in the literature, where excellent allele specificity can be achieved at fragment lengths of up to 4 kb.

B.2.a) Double and Single Strand-Based Allele Enrichment Methods

The goal of allele-specific selection methods is to physically fractionate a nucleic acid mixture (the starting material) to obtain a population of molecules enriched for a single or specific allele of the nucleic acid mixture to be analyzed. The details of the procedure depend on the polymorphic nucleotide(s) that provide the basis for allele enrichment and the immediate flanking sequence upstream and/or downstream of the polymorphic site. As explained below, different types of sequence polymorphisms lend themselves to different types of allele enrichment methods.

Once a polymorphic site is selected for allele enrichment, in one embodiment the enrichment steps can be carried out as follows: (i) prepare DNA fragments for allele enrichment; (ii) add to the DNA fragments a molecule that binds DNA in a sequence specific manner (hereafter referred to as the 'DNA binding molecule') such that one allele of the target DNA segment is bound and the other not; (iii) allow complexes to form between DNA fragments and the allele-specific DNA binding molecule under conditions optimized for allele selective binding; (iv) add a second reagent, such as an antibody, that binds to the allele-specific DNA binding molecule (which in turn is bound to DNA fragments, including fragments comprising the selected allele); (v) remove the complex containing (selected allele+DNA binding protein+second reagent bound to DNA binding protein) from the starting DNA sample by either physical, affinity (including immunological), chromatographic or other means; (vi) releasing the bound DNA from the complex and (vii) genotyping it to determine the haplotype of the selected allele. These steps are described in greater detail below, except for step (ii), addition of an allele-specific DNA binding molecule, which is described at greater length in the following sections, each of which describes one class of allele-specific DNA binding molecules in detail.

(i) Preparation of DNA fragments for allele enrichment. The condition of the DNA can be controlled in a variety of ways: DNA concentration, size distribution, state of the DNA ends (blunt, 3' overhang, 5' overhang, specific sequence at the end, etc.), degree of elongation, etc. The DNA also can be suspended in a buffer that maximizes sequence specific DNA binding. Exemplary DNA concentrations for these procedures are in the range from 100 nanograms to 10 micrograms of genomic DNA in a volume of 10 to 1000 microliters.

Typically lower amounts of DNA and lower volumes are used, in order to control costs and to minimize the amount of blood or tissue that must be obtained from a subject to obtain sufficient DNA for a successful haplotyping procedure. As described above, the size of the DNA fragments is controlled to produce a majority of desired fragments which span the DNA segment to be haplotyped. The length of such a segment can vary from 500 nucleotides to 1 kb, 3 kb, 5 kb, 10 kb, 20 kb, 50 kb, 100 kb or more. Fragments of the desired size can be produced by random or specific DNA cleavage procedures, as described above.

The exploitation of allele-specific sequences at the ends of restriction cleaved DNA molecules for haplotyping is described below. An optimal buffer and binding conditions provide for maximum discrimination between the binding of the allele-specific DNA binding molecule to the selected allele vs. the non-selected allele. Although the binding of the DNA binding molecule to many other irrelevant DNA fragments in the genomic DNA is unavoidable, such binding should not interfere with the enrichment of the selected allele.

(ii) Described below are several types of allele-specific DNA binding molecules, including proteins, peptides, oligonucleotides, and small molecules as well as combinations of these molecules. These molecules can be designed or selected to bind double-stranded (ds) or single-stranded (ss) DNA in a sequence specific manner.

(iii) Complexes are formed between DNA and the allele-specific DNA binding molecule under conditions optimized for binding specificity—e.g., conditions of ionic strength, pH, temperature and time that promote formation of specific complexes between the binding molecules and the DNA. Optimization of allele selective binding conditions is in general empirical and, in addition to optimization of salt, pH and temperature can include addition of cofactors. Cofactors include molecules known to affect DNA hybridization properties, such as glycerol, spermidine or tetramethyl ammonium chloride (TMAC), as well as molecules that exclude water such as dextran sulphate and polyethylene glycol (PEG). Optimization of temperature can entail use of a temperature gradient, for example ramping temperature from >95° C. down to <40° C.

(iv) After the selected DNA fragment is bound to an allele-specific DNA binding molecule a second reagent, such as an antibody, aptamer, streptavidin or nickel coated bead or other ligand that binds to the allele-specific DNA binding molecule can be added to the reaction mix. Said second reagent forms complexes with the DNA binding molecules (and any DNA fragments they are bound to) that facilitates their removal from the remaining DNA fragments. This step can be omitted if the DNA binding molecule added in step (ii) already contains or is attached to a ligand or a bead or is otherwise modified in a way that facilitates separation after formation of allele-specific complexes in step (iii). For example, if the DNA binding molecule is a protein it can be modified by appending a polyhistidine tag or an epitope for antibody binding such as the hemagglutinin (HA) epitope of influenza virus. Then, before, during or after step (iii), nickel coated beads can be added to the DNA sample, or alternatively the sample can be delivered to a nickel column for chromatography, using methods known in the art (e.g., QIAexpress Ni-NTA Protein Purification System, Qiagen, Inc., Valencia, Calif.). First free DNA is washed through the column, then the DNA bound to the poly-his containing DNA binding protein is eluted with 100-200 mM imidazole using methods known in the art. In this way DNA fractions enriched for both alleles (bound and unbound) are collected from one procedure. An equivalent procedure for an epitope tagged DNA binding molecule can include addition of antibody coated beads to form {bead-protein-DNA} complexes, which can then be removed by a variety of physical methods (see below). Alternatively, the protein-DNA complexes can be applied to an antibody column (using an antibody that binds to the epitope engineered into the allele-specific DNA binding molecule). A consideration in designing and optimizing a specific allele enrichment procedure is that the enrichment conditions are sufficiently mild that they do not cause dissociation of the {DNA binding molecule+selected allele} complexes to an extent that there is too little DNA remaining at the end of the procedure for robust DNA amplification and genotyping.

(v) Separation of complexes containing the {DNA binding molecule+selected allele}, (plus or minus an optional third moiety bound to the DNA binding protein) from the remainder of the DNA sample can be accomplished by physical, affinity (including immunological) or other means. Methods for removing complexes include application of a magnetic field to remove magnetic beads attached to the selected allele via the DNA binding molecule or other moiety; centrifugation (e.g., using a dense bead coated with a ligand like an antibody, nickel, streptavidin or other ligand known in the art, that binds to the DNA binding molecule), or filtration (for example using a filter to arrest beads coated with ligand to which the DNA binding molecule and the attached DNA fragments are bound, while allowing free DNA molecules to pass through), or by affinity methods, such as immunological methods (for example an antibody column that binds the DNA binding molecule which is bound to the selected DNA, or which binds to a ligand which in turn is bound to the DNA binding molecule), or by affinity chromatography (e.g., chromatography over a nickel column if the DNA binding molecule is a protein that has been modified to include a polyhistidine tag, or if the DNA binding molecule is bound to a second molecule that contains such a tag). The separation of the allele-specific DNA binding molecule and its bound DNA from the remaining DNA can be accomplished by any of the above or related methods known in the art, many of which are available in kit form from companies such as Qiagen, Novagen, Invitrogen, Stratagene, ProMega, Clontech, Amersham/Pharmacia Biotech, New England Biolabs and others known to those skilled in the art.

(vi) Release the bound DNA from the partially purified complexes containing the selected allele. This step can be accomplished by chemical or thermal denaturing conditions (addition of sodium hydroxide; boiling) or by milder changes in buffer conditions (salt, cofactors) that reduce the affinity of the DNA binding molecule for the selected allele.

(vii) Genotyping the enriched DNA to determine the haplotype of the selected allele can be accomplished using the base-specific fragmentation mass spectrometry genotyping methods described herein (e.g., MassCLEAVE™ assay) or by other genotyping methods known in the art, including chemical cleavage methods (Nucleave, Variagenics, Cambridge, Mass.), primer extension based methods (Orchid, Sequenom, others), cleavase based methods (Third Wave, Madison, Wis.), bead based methods (Luminex, Illumina) miniaturized electrophoresis methods (Kiva Genetics), pyrosequencing (Pyrosequencing), using TaqMan (Applied Biosystems) or by DNA sequencing. The key requirement of any genotyping method is that it be sufficiently sensitive to detect the amount of DNA remaining after allele enrichment. If there is a small quantity of DNA after allele enrichment (less than 1 nanogram) then it can be necessary to increase the number of PCR cycles, or to perform a two step amplification procedure in order to boost the sensitivity of the genotyping procedure. For example the enriched allele can be subjected to 40 cycles of PCR amplification with a first set of primers, and the product of that PCR can then be subjected to a second round of PCR with two new primers internal to the first set of primers.

No DNA amplification procedure is required in any step of the enrichment procedure until the genotyping step at the end, so allele enrichment methods are not constrained by the limitations of amplification procedures such as PCR. As a result, the length of fragments that can be analyzed is, in principal, quite large. In contrast, there is no chance of artifactual DNA strand interchange with those particular allele enrichment methods. Apart from these advantages over amplification methods, the strand selection methods described below also are attractive in that the costs of optimizing and carrying out a long range PCR amplification are avoided. Furthermore, the allele enrichment procedures described herein are for the most part generic: the same basic steps can be followed for any DNA fragment.

B.2.b) Double-Stranded vs. Single-Stranded Allele Selection Methods

Allele selection can be accomplished using single- or double-stranded DNA. Single-stranded DNA is produced by denaturing double-stranded DNA. Denaturation can be effected, for example by heating or by treatment with alkali, such as after a sizing procedure has been applied to double-stranded DNA to achieve an optimal size distribution of DNA fragments. Denaturation methods using single- and double-stranded DNA have advantages and disadvantages. One advantage of single-stranded methods is that the specificity of Watson-Crick base pairing can be exploited for the affinity capture of one allele. Disadvantages of single-strand methods include: (i) the propensity of single-stranded DNA molecules to anneal to themselves (forming complex secondary structures) or to other, only partially complementary single-stranded molecules. For example the ubiquitous human DNA repeat element Alu (which is up to ≈280 nucleotides long) can cause two non-complementary strands to anneal; (ii) Single-stranded DNA is more susceptible to breakage than double-stranded DNA. Strand breaks destroy the physical contiguity that is essential for haplotyping.

Double-stranded DNA has several advantages over single-stranded DNA as the starting point for the haplotyping methods provided herein. First, it is less susceptible to breakage. Second, it is less likely to bind non-specifically to itself or other DNA molecules (whether single-stranded or double-stranded). Third, there are a variety of high affinity, sequence specific interactions between double-stranded DNA and proteins (e.g., restriction enzymes, transcription factors, natural and artificial zinc finger proteins), as well as high affinity interactions between double-stranded DNA and single-stranded DNA or modified oligonucleotides (e.g., via Hoogsteen or reverse Hoogsteen base pairing) and between double-stranded DNA and small molecules (e.g., polyamides) that can provide the basis for allele enrichment. Another type of structure that can be exploited for allele enrichment is D-loops, formed by strand invasion of a duplex DNA molecule by an oligonucleotide or a DNA-like molecule such as peptide nucleic acid (PNA). D loop formation can be facilitated by addition of *E. Coli* RecA protein, using methods known in the art. Fourth, restriction enzyme cleaved double-stranded DNA can have termini that can provide the basis for allele-specific treatments, including affinity selection (e.g., ligation to an adapter strand), strand degradation (e.g., allele selective degradation of one allele but not the other), circularization and other procedures described below.

B.3. Protein-Based Allele Enrichment Methods

In protein-based allele enrichment methods a DNA binding protein with differential affinity for the two allelic DNA segments to be separated is added to a mixture of genomic DNA or cDNA fragments (which have been denatured in the case of single-strand methods). Since most sequence specific binding proteins recognize double-stranded DNA, dsDNA is typically a starting material for protein-based allele enrichment methods. Next, complexes are formed between the binding protein and DNA segments containing the sequence motif recognized by the binding protein. The DNA segments to be haplotyped must differ in respect to the presence or absence of the protein binding site. As described above, this requirement can be met in several ways, such as by using restriction endonuclease(s) to produce DNA fragments that contain only one binding site (selected allele), or none (other allele), for the binding protein. Subsequently the protein—DNA complexes are purified from the DNA that is not protein bound. This purification can be accomplished by adding a second reagent that (i) binds to the binding protein, and (ii) can be physically separated from the mixture. The second reagent can be a bead, a magnetic particle, a surface or any other structure that facilitates the physical separation step. It can be modified by coupling to a protein binding reagent. Specific reagents for binding to proteins include antibodies, nickel-polyhistidine affinity, avidin-biotin affinity and similar schemes known to those skilled in the art. The physical separation of the complexes containing binding protein bound to DNA can be effected by gravity, centrifugation, a magnetic field, filtration, chromatography, electrophoresis or other means. The final step is to genotype the purified material, which yields the haplotype.

B.3.a) Protein-Based Double Stranded Allele Selection Methods

The major categories of naturally occurring sequence specific DNA binding proteins include zinc finger proteins and helix-turn-helix transcription factors. In addition, proteins that normally act on DNA as a substrate can be made to act as DNA binding proteins either by (i) alterations of the aqueous environment (e.g., removal of ions, substrates or cofactors essential for the enzymatic function of the protein, such as divalent cations) or (ii) by mutagenesis of the protein to disrupt catalytic, but not binding, function. Classes of enzymes that bind to specific dsDNA sequences include restriction endonucleases and DNA methylases. (For a recent review see: Roberts R. J. and D. Macelis, *Nucleic Acids Res.* 28(1):306-7 (2000). Finally, in vitro evolution methods (DNA shuffling, dirty PCR and related methods) can be used to create and select proteins or peptides with novel DNA binding properties. The starting material for such methods can be the DNA sequence of a known DNA binding protein or proteins, which can be mutagenized globally or in specific segments known to affect DNA binding, or can be otherwise permuted and then tested or selected for DNA binding properties. Alternatively the starting material can be genes that encode enzymes for which DNA is a substrate—e.g., restriction enzymes, DNA or RNA polymerases, DNA or RNA helicases, topoisomerases, gyrases or other enzymes. Such experiments might be useful for producing sequence specific ssDNA binding proteins, as well as sequence specific dsDNA binding proteins. For recent descriptions of in vitro evolution methods see: Minshull J. and W. P. Stemmer, *Curr Opin Chem Biol.* 3(3):284-90 (1999); Giver, L., and F. H. Arnold, *Curr Opin Chem Biol.* 2(3):335-8 (1998); Bogarad, L. D. and M. W. Deem, *Proc. Natl. Acad. Sci. USA* 96(6):2591-5 (1999); Gorse, D., Rees, A., Kaczorek, M. and R. Lahana, *Drug Discov Today* 4(6):257-264 (1999).

Among the classes of DNA binding proteins enumerated above which can be used to select DNA molecules, are proteins that have some or all of the following properties: (i) any two sequences differing by one nucleotide (or by one nucleotide pair in the case of dsDNA) can be discriminated, not limited by whether or not one version of the sequence is a palindrome, or by any other sequence constraint, (ii) DNA binding proteins can be designed or selected using standard conditions, so that the design or selection of proteins for many different sequence pairs is not onerous. (This requirement arises from the concern that, in order to be able to readily select any given DNA molecule for haplotyping it is desirable to have a large collection of DNA binding proteins, each capable of discriminating a different pair of sequences.) (iii) The affinity of the protein for the selected DNA sequence is sufficient to withstand the physical and/or chemical stresses introduced in the allele enrichment procedure. (iv) The DNA binding molecules are stable enough to remain in native conformation during the allele enrichment procedure, and can be stored for long periods of time. (v) The length of sequence bound by the allele-specific DNA binding protein is typically at least six nucleotides (or nucleotide pairs), generally at least 8 nucleotides, and most typically 9 nucleotides or longer. The longer the recognition sequence, the fewer molecules in the genomic DNA fragment mixture will be bound, and therefore the less 'background' DNA there accompany the enriched allele. In addition to the five foregoing criteria, it can be desirable to make a fusion between the DNA binding protein and a second protein so as to facilitate enrichment of the DNA binding protein. For example, appending an epitope containing protein allow selection by antibody based methods. Appending six or more histidine residues allow selection by zinc affinity methods.

B.3.b) Zinc Finger Proteins

Zinc finger proteins are a class of DNA binding proteins. It is well-established that zinc finger proteins can bind to virtually any DNA sequence motif, and are not limited to palindromic sequences, as are type II restriction endonucleases and helix-turn-helix transcription factors (see, for example: Choo, Y. and A. Klug, *Proc. Natl. Acad. Sci. USA* 91:11163-11167 (1994); Jamieson, A. C., Wang, H. and S.-H. Kim, *Proc. Natl. Acad. Sci. USA* 93:12834-12839 (1996); Segal, D. J., Dreier, B., Beerli, R. R. and C. F. Barbas, *Proc. Natl. Acad. Sci. USA* 96:2758-2763 (1999); Segal, D. J. and C. F. Barbas *Curr. Opin. Chem. Biol.* 4:34-39 (2000)). These papers and other work in the field demonstrate that it is possible to generate zinc finger proteins that bind to virtually any DNA sequence from 3 nucleotides up to 18 nucleotides. Further, these studies show that in vitro generated zinc finger proteins are capable of binding specific DNA sequences with low nanomolar or even subnanomolar affinity, and are capable of distinguishing sequences that differ by only one base pair with 10 to 100-fold or even greater differences in affinity. It also has been demonstrated that zinc finger proteins can be modified by fusion with other protein domains that provide detectable labels or attachment domains. For example zinc finger proteins can be fused with jellyfish green fibrillary protein (GFP) for labelling purposes, or fused to polyhistidine at the amino or carboxyl terminus, or fused with an antibody binding domain such as glutathione transferase (GST) or influenza virus hemagglutinin (HA) (for which there are commercially available antisera) for attachment and selection purposes.

Methods for making zinc finger proteins of desired sequence specificity are well known in the art and have recently been adapted to large scale experiments. See, in addition to the above references: Beerli R. R., Dreier B. and C. F. Barbas, *Proc. Natl. Acad. Sci. USA* 97:1495-1500 (2000); Beerli R. R., Segal D. J., Dreier B. and C. F. Barbas, *Proc. Natl. Acad. Sci. USA* 95:14628-14633 (1998). Methods for using phage display to select zinc finger proteins with desired specificity from large libraries also have been described: Rebar E. J. and C. O. Pabo, *Science* 263(5147): 671-673 (1994); Rebar E. J., Greisman H. A. and C. O. Pabo, *Methods Enzymol.* 267:129-149 (1996). The phage display method offers one way to bind selected alleles to a large complex that can be efficiently removed from a mixture of DNA fragments. Preventing nonspecific DNA binding to intact phage requires careful optimization of blocking conditions.

For the haplotyping methods described in this application the length of the DNA sequence recognized by a zinc finger protein can range from 3 nucleotides to 18 or more nucleotides. Sequences less than 6-nucleotides are generally not useful for haplotyping because, unless they contain the dinucleotide CpG, they occur too frequently in DNA to allow haplotyping over distances of several kb or longer—that is, for DNA fragments greater than, say, 3 kb, both alleles frequently have one or more copies of any sequence motif that is shorter than six nucleotides, because the average interval between three, four and five nucleotide repeats (assuming random order sequence and equal occurrence of each of the four nucleotides, neither of which actually obtains) is $4^3=64$, $4^4=256$ and $4^5=1024$. If both alleles have a copy of a target sequence then clearly that sequence cannot be used to selectively enrich one allele. Zinc finger proteins can be generated that recognize 6, 9, 12 or 18 nucleotides. Longer sequences provide greater specificity, since such longer sequences are statistically more rare in a genome. The length of the sequence bound is only one of several considerations in selecting a zinc finger protein. The specificity of binding and the affinity of binding is considered. Typically a zinc finger protein has a specificity of at least 10-fold, and 100-fold or greater, with respect to all sequences that differ from a selected sequence by one or more nucleotides. This level of specificity provides the allele selectivity required for successful allele enrichment. Optimal zinc finger proteins must also have a high affinity for the selected sequence. Typically the dissociation constant of the zinc finger protein for the target DNA sequence is less than 50 nanomolar, generally less than 10 nanomolar, and typically less than 2 nanomolar. Multiple zinc finger proteins that meet all the enumerated criteria have been produced, demonstrating the ability of the skilled artisan to accomplish the necessary modifications to naturally occurring zinc finger proteins. Methods for improving the specificity and affinity of binding include random or site directed mutagenesis, selection of phage bearing mutant zinc finger proteins with desired specificity from large libraries of phage, and in vitro evolution methods.

Because each zinc finger recognizes three nucleotides, one way to make zinc finger proteins that recognize sequences of six nucleotides or longer is to assemble two or more zinc fingers with known binding properties. The use of zinc fingers as modular building blocks has been demonstrated by Barbas and colleagues (see: *Proc. Natl. Acad. Sci. USA* 95:14628-14633 (1998)) for nucleotide sequences of the form $(GNN)^x$ where G is guanine, N is any of the four nucleotides, and x indicates the number of times the GNN motif is repeated.

A large number of zinc finger proteins exist in nature, and a still larger number have been created in vitro (e.g., see work cited above). Any of these known zinc finger proteins can constitute a useful starting point for the construction of a useful set of allele-specific DNA binding proteins. The protein Zif268 is the most extensively characterized zinc finger protein, and has the additional advantage in that there is relatively little target site overlap between adjacent zinc fingers, making it well suited to the modular construction of zinc finger proteins with desired DNA sequence binding specificity. See, for example: Segal, D. J., et al., *Proc. Natl. Acad. Sci. USA* 96:2758-2763 (1999). Zif268 is an exemplary backbone for production of mutant zinc finger proteins.

B.3.c) Restriction Endonucleases

Another class of sequence specific DNA binding proteins useful for allele enrichment is restriction endonucleases. There are over 400 commercially available restriction endonucleases, and hundreds more that have been discovered and characterized with respect to their binding specificity. (Roberts R. J. and D. Macelis, *Nucleic Acids Res.* 28(1):306-7 (2000). Collectively these enzymes recognize a substantial fraction of all 4, 5 and 6 nucleotide sequences (of which there are 256, 1024 and 4096, respectively). For certain polymorphic nucleotides, the exquisite sequence specificity of these enzymes can be used to selectively bind one allelic DNA fragment that contains the cognate recognition site, while not binding to the DNA fragment corresponding to the other allele, which lacks the cognate site. Restriction endonucleases do not have the flexibility that zinc finger proteins do in being able to selectively bind virtually any sequence up to 18 nucleotides in length, but they do have the attraction of being highly specific, readily available, and for the most part inexpensive to produce. The identification of polymorphic sites that lie within restriction enzyme binding sequences becomes much simpler as the sequence of the human genome is completed, and the generation of restriction maps becomes primarily a computational, rather than an experimental, activity.

In order for restriction endonucleases to be useful as DNA binding proteins their DNA cleaving function must first be neutralized or inactivated; otherwise DNA is cleaved and released. Inactivation can be accomplished in two ways. First, one can add restriction endonucleases to DNA, allow them to bind under conditions that do not permit cleavage, and then remove the DNA-protein complex. The simplest way to prevent restriction enzyme cleavage is to withhold divalent cations from the buffer. Second, one can alter restriction endonucleases so that they still bind DNA but can not cleave it. This can be accomplished by altering the sequence of the gene encoding the restriction endonuclease, using methods known in the art, or it can be accomplished by post-translational modification of the restriction endonuclease, using chemically reactive small molecules.

The first approach—withholding essential cofactors, such as magnesium or manganese has the advantage that no modification of restriction enzymes or the genes that encode them is necessary. Instead, conditions are determined that are permissive for binding but nonpermissive for cleavage. It can not be possible to identify such conditions for all restriction enzymes; some enzymes appear to require divalent cations for specific, high affinity recognition of cognate DNA. For such enzymes it can be possible to produce mutant forms that do not require divalent cations for high affinity, specific binding to cognate DNA. For example, mutants of the restriction enzyme Mun I (which binds the sequence CAATTG) have been produced that recognize and bind (but do not restrict) cognate DNA with high specificity and affinity in the absence of magnesium ion. In contrast, wild type Mun I does not exhibit sequence specific DNA binding in the absence of magnesium ion. The amino acid changes in the mutant Mun I enzymes (D83A, E98A) have been proposed to simulate the effect of magnesium ion in conferring specificity. See, for example: Lagunavicius, A. and V. Siksnys, *Biochemistry* 36:11086-11092 (1997). Structural modification of restriction enzymes to alter their cleaving properties but not their binding properties in the presence of magnesium ion has also been demonstrated.

For example, in studies of the restriction enzyme Eco R I (which binds the sequence GAATTC) it has been demonstrated that DNA sequence recognition and cleaving activity can be dissociated. Studies have shown that mutant Eco RI enzymes with various amino acid substitutions at residues Met137 and Ile197 bind cognate DNA (i.e., 5'-GAATTC-3') with high specificity but cleave with reduced or unmeasurably low activity. See: Ivanenko, T., Heitman, J. and A. Kiss, *Biol. Chem.* 379:459-465 (1998). Other work has led to the identification of mutant Eco RI proteins that have substantially increased affinity for the cognate binding site, while lacking cleavage activity. For example, the Eco RI mutant Gln111 binds GAATTC with =1,000 fold higher affinity than wild type enzyme, but has ≈10,000 lower rate constant for cleavage. (See: King, K., Benkovic, S. J. and P. Modrich, *J. Biol. Chem.* 264:11807-15 (1989). Eco RI Gln111 has been used to image Eco RI sites in linearized 3.2-6.8 kb plasmids using atomic force microscopy, a method that exploits the high binding affinity and negligible cleavage activity of the mutant protein. The Eco RI Gln111 protein is an exemplary reagent for the methods provided herein, as a reagent for the selective enrichment of alleles that contain a GAATTC sequence (and consequent depletion of alleles that lack such a sequence). Exemplary conditions for selective binding of Eco RI Gln111 to DNA fragments with cognate sequence can include ≈50-100 mM sodium chloride, 10-20 mM magnesium ion (e.g., $MgCl_2$) and pH 7.5 in tris or phosphate buffer. Typically there is molar equivalence of Eco RI Gln111 and cognate DNA binding sites in the sample (e.g., genomic DNA); generally there is a 5, 10, 20 or 50-fold molar excess of enzyme over DNA. Exemplary methods for enrichment of the Eco RI bound allele from the non-bound allele include the synthesis of a fusion protein between Eco RI Gln111 and a protein domain that includes an antibody binding site for a commercially available enzyme. Influenza hemagglutinin, beta galactosidase or glutathione S transferase and polyhistidine domains are available as commercial kits for protein purification.

There are several schemes for producing, from genomic DNA, two homologous (allelic) fragments of a gene that differ in respect to the presence or absence of a sequence such as an Eco RI site. Scheme 1: if the complete sequence of the region being haplotyped is known then the location and identity of all restriction sites, including the subset of restriction sites that include polymorphic nucleotides in their recognition sequence, can be determined trivially by computational analysis using commercially available software. Those restriction sites that overlap polymorphic nucleotides in the DNA segment of interest can be assessed for suitability as allele enrichment sites. The optimal characteristics of an allele enrichment site include: (i) The site occurs once, or not at all (depending on the allele) in a DNA segment to be haplotyped. This is crucial since the basis of the allele enrichment is the attachment of a protein to the binding site in the allele to be enriched, and its absence in the other allele present in the genomic DNA sample being haplotyped. (ii) There is a pair of nonpolymorphic restriction sites, different from the site being used for allele enrichment, that flank the polymorphic site and span a DNA segment deemed useful for haplotype analysis.

The steps for allele enrichment then comprise: restrict genomic DNA with the selected enzyme(s) that flank the polymorphic site so as to produce a DNA segment useful for haplotype analysis (as well as many other genomic DNA fragments); add the DNA binding protein (i.e., the cleavage-inactive restriction enzyme) in a buffer that promotes specific binding to the cognate site (and, if necessary, prevents the restriction enzyme from cleaving its cognate site); selectively remove the restriction enzyme-complex from the genomic DNA by any of the physical or affinity based methods described above—antibody, nickel—histidine, etc. Subsequently, suspend the enriched allele in aqueous buffer and genotype two or more polymorphic sites to determine a haplotype. Scheme 2 is similar but does not require a specific restriction step. Instead, one randomly fragments genomic DNA into segments that, on average, are approximately the length of the segment to be haplotyped. Then add the DNA binding protein and proceed with the enrichment as above. The disadvantage of this scheme is that there can be DNA fragments that include non-polymorphic copies of the cognate sequence for the DNA binding protein. The presence of such fragments limits the degree of allele enrichment because they co-purify with the targeted allele, and produce background signal in the subsequent analysis steps. This problem can be addressed by reducing the average size of the fragments in the random fragmentation procedure.

Because of the requirement that the enriched allele fragment have zero or one copies of the sequence to be used for attachment of the restriction, optimal restriction enzymes for these haplotyping methods recognize sequences of 5 nucleotides or greater. Typically they recognize sequences of 6 nucleotides or greater; typically the cognate sites of such enzymes contain one or more dinucleotides or other sequence motifs that are proportionately underrepresented in genomic DNA of the organism that is being haplotyped. Generally for haplotyping methods applied to mammalian genomic DNA, they contain one or more 5'-CpG-3' sequences, because CpG dinucleotides are substantially depleted in mammalian genomes. Restriction enzymes that include CpG dinucleotides include Taq I, Msp I, Hha I and others known in the art.

B.3.d) Additional Restriction Endonuclease Based Methods

A limitation of the restriction enzyme based allele capture method is that the length of DNA fragment that can be haplotyped depends on the local restriction map. In some cases it can be difficult to find a polymorphic restriction site for which a cleavage-inactive restriction enzyme is available and for which the nearest 5' and 3' flanking sequences are at an optimal distance for haplotyping; often the flanking restriction enzyme cleavage sites are closer to the polymorphic site than desired, limiting the length of DNA segment that can be haplotyped. For example, it can be optimal from a genetic point of view to haplotype a 15 kb segment of DNA, but there can be no polymorphic restriction sites that are flanked by sites that allow isolation of the desired 15 kb segment. One approach to this problem is to haplotype several small DNA fragments that collectively span the 15 kb segment of interest. A composite haplotype can then be assembled by analysis of the overlaps between the small fragments.

A more general, and more useful, method for circumventing the limitations occasionally imposed by difficult restriction maps is to incorporate aspects of the RecA assisted restriction endonuclease (RARE) method in the haplotyping procedure. (For a description of the RARE procedure see: Ferrin, L. J. and R. D. Camerini-Otero, *Science* 254:1494-1497 (1991); Koob, M. et al., *Nucleic Acids Res.* 20:5831-5836 (1992). When the RARE techniques are used in the protein mediated allele enrichment method it is possible to haplotype DNA segments of virtually any length, regardless of the local restriction site map.

First, the DNA is sized, either by random fragmentation to produce fragments in the right size range (e.g., approximately 15 kb average size), or one can use any restriction endonuclease or pair of restriction endonucleases to cleave genomic DNA (based on the known restriction map) so as to produce fragments spanning the segment to be haplotyped. In the RARE haplotyping procedure, one then uses an oligonucleotide to form a D loop with the segment of DNA that contains the polymorphic restriction site (the site that ultimately is used to capture the DNA segment to be haplotyped). (The other copy of the allele present in the analyte sample lacks the restriction enzyme sequence as a consequence of the polymorphism.) Formation of the D loop can be enhanced by addition of *E. Coli* RecA protein, which assembles around the single-stranded DNA to form a nucleoprotein filament which then slides along double-stranded DNA fragments until it reaches a complementary strand. RecA protein, in a complex with a gamma-S analog of ATP and a 30-60 nucleotide long oligodeoxynucleotide complementary or identical to the sequence-targeted site in which the protected restriction site is embedded, then mediates strand invasion by the oligodeoxynucleotide, forming the D loop.

Once this loop is formed the next step is to methylate all copies of the polymorphic restriction site using a DNA methylase. Substantially all copies of the restriction site present in the genomic DNA mixture are methylated. (One nucleotide, usually C, is methylated.) The one polymorphic restriction site which participates in the D loop is not methylated because the D loop is not recognized by the DNA methylase. Next the D loop is disassembled and the methylase inactivated or removed. This leaves the targeted restriction site available for restriction enzyme binding (on the one allele that contains the restriction site). Finally, the restriction-inactive but high affinity binding protein (e.g., Eco RI Gln111) is added to the mixture of genomic DNA fragments. The only fragment that should have an available Eco RI site is the fragment to be haplotyped. Any of several methods can be used to selectively remove that fragment: the cleavage-inactive restriction enzyme can be fused to a protein that serves as a handle to facilitate easy removal by nickel-histidine, antibody-antigen or other protein-protein interaction, as described in detail elsewhere herein. Alternatively, an antibody against the restriction enzyme can be prepared and used to capture the restriction enzyme-allele fragment complex to a bead or column to which the antibody is bound, or other methods known in the art can be employed.

The advantage of the RARE assisted haplotyping method is that the local restriction map, and in particular the occurrence of other Eco RI sites (in this example) nearby, is no longer a limitation. Further, the methylation of all sites save the polymorphic site eliminates the preference for restriction enzymes that recognize 6 or more nucleotides. With the RARE haplotyping technique any enzyme, including one that recognizes a four nucleotide sequence, is effective for allele enrichment. This is a particularly useful aspect of the methods provided herein, because four nucleotide sequences recognized by restriction enzymes more often encompass polymorphic sites than 5 or 6 nucleotide sequences, and there are more DNA methylases for 4 nucleotide sequences than for 6 nucleotide sequences recognized by restriction enzymes. Restriction sites for RARE assisted haplotyping include those for which DNA methylases are commercially available, including, without limitation, Alu I, Bam HI, Hae III, Hpa II, Taq I, Msp I, Hha I, Mbo I and Eco RI methylases.

The use of peptides for allele enrichment is described below in the discussion of small molecules that can be used for allele enrichment.

B.4. Nucleic Acid-Based Allele Selection Methods

In another embodiment, nucleic acids and nucleic acid analogs that bind specifically to double-stranded DNA can be targeted to polymorphic sites and used as the basis for physical separation of alleles. Ligands attached to the targeting oligonucleotides, such as, without limitation, biotin, fluorescein, polyhistidine or magnetic beads, can provide the basis for subsequent enrichment of bound alleles. Sequence specific methods for the capture of double-stranded DNA, useful for the haplotyping methods provided herein, include: (i) Triple helical interactions between single-stranded DNA (e.g., oligonucleotides) and double-stranded DNA via Hoogsteen or reverse Hoogsteen base pairing; (ii) D-loop formation, again between a single-stranded DNA and a double-stranded DNA; (iii) D-loop formation between peptide nucleic acid (PNA) and a double-stranded DNA; and (iv) in vitro nucleic acid evolution methods (referred to as SELEX) can be used to derive natural or modified nucleic acids (aptamers) that bind double-stranded DNA in a sequence specific manner via any combination of Watson-Crick or Hoogsteen base pairing, hydrogen bonds, van der Waals forces or other interaction.

The D loop is formed by the displacement of one strand of the double helix by the invading single-strand. RecA protein, as indicated above, facilitates D Loop formation, albeit with only limited stringency for the extent of homology between the invading and invaded sequences nucleotide analogs. Such interactions are useful for allele enrichment when a polymorphic site lies in a sequence context that conforms to the requirements for Hoogsteen or reverse Hoogsteen base pairing. The sequence requirements generally include a homopyrimidine/homopurine sequence in the double-stranded DNA, however the discovery of nucleotide analogs that base pair with pyrimidines in triplex structures has increased the repertoire of sequences which can participate in triple stranded complexes.

B.4.a) Nucleic Acid-Based Double Stranded Allele Selection Methods

In another aspect, nucleic acids that bind specifically to double-stranded DNA can be targeted to polymorphic sites and used as the basis for physical separation of alleles. The best known types of specific interactions involve triple helical interactions formed via Hoogsteen or reverse Hoogsteen base pairing. These interactions are useful for haplotyping when a polymorphic site lies within a sequence context that conforms to the requirements for Hoogsteen or reverse Hoogsteen base pairing. These requirements typically include a homopyrimidine/homopurine sequence, however the discovery of nucleic acid modifications that permit novel base pairings is resulting in an expanded repertoire of sequences. Nonetheless, a more general scheme for selective binding to polymorphic DNA sequences can be used.

In another aspect, the formation of D loops by strand invasion of dsDNA can be the basis for an allele-specific interaction, and secondarily for an allele enrichment scheme. Peptide nucleic acid (PNA) is an exemplary material for strand invasion. Due to its high affinity DNA binding PNA has been shown capable of high efficiency strand invasion of duplex DNA. (Peffer N J, Hanvey J C, Bisi J E, et al., *Proc. Natl. Acad. Sci. USA* 90(22):10648-52 (1993); Kurakin A, Larsen H J, Nielsen P E., *Chem Biol.* 5(2):81-9 (1998). The basis of a PNA strand invasion affinity selection is similar to protein-based methods, except the sequence-specific DNA-PNA complexes formed by strand invasion are the basis of an enrichment procedure that exploits an affinity tag attached to the PNA. The affinity tags can be a binding site for an antibody such as fluorescein or rhodamine, or polyhistidine (to be selected by nickel affinity chromatography), or biotin, (to be selected using avidin- or streptavidin-coated beads or surface) or other affinity selection schemes known to those skilled in the art.

In another embodiment, in vitro nucleic acid evolution methods (referred to as aptamers or SELEX) can be used to derive natural or modified nucleic acids that bind double-stranded DNA in a sequence specific manner. Methods for high throughput derivation of nucleic acids capable of binding virtually any target molecule have been described. (Drolet D W, Jenison R D, Smith et al. A high throughput platform for systematic evolution of ligands by exponential enrichment (SELEX). *Comb Chem High Throughput Screen* 2(5):271-8 (October 1999)).

B.4.b) Other Double-Stranded Allele Selection Methods

In another aspect, non-protein, non-nucleic acid molecules can be the basis for affinity selection of double-stranded DNA. (Mapp A K, Ansari A Z, Ptashne M, et al., *Proc. Natl. Acad. Sci. USA* 97(8):3930-5 (2000); Dervan P B, Burli R W., *Curr Opin Chem Biol.* 3(6):688-93 (1999); White S, Szewczyk J W, Turner J M, et al., *Nature* 391(6666):468-71 (1999).

B.5. Allele-Specific Capture of Single-Stranded DNA or RNA

In this example, modified oligonucleotides or modified nucleotide triphosphates are used as affinity reagents to partially purify a complementary DNA species (the allele to be haplotyped) with which they have formed a duplex. The nucleotide or oligonucleotide modification can include, for example, addition of a compound that binds with high affinity to a known partner such as biotin/avidin or polyhistidine/nickel, or it can include covalent addition of a compound, such as rhodamine or fluorescein, for which high affinity antibodies are available, or it can include addition of a metal that allows physical separation using a magnetic field, or it can involve addition of a reactive chemical group that, upon addition of a specific reagent or physical energy (e.g., uv light) forms a covalent bond with a second compound that in turn is linked to a molecule or structure that permits physical separation.

Exemplary of such modifications is biotin. DNA or RNA once hybridized to biotinylated oligonucleotides or nucleotides can be separated from non-hybridized DNA or RNA using streptavidin on a solid support. Other modifications include but are not limited to: antigens and antibodies, peptides, nucleic acids, and proteins that when attached to oligonucleotides or nucleotides bind to some other molecule on a solid support. For the purposes of this disclosure, biotin is an exemplary modification of the oligonucleotides or nucleotides and streptavidin is attached to the solid support.

Oligonucleotides used in the descriptions below can comprise either normal nucleotides and/or linkages or modified nucleotides and/or linkages. The only requirement is that the oligonucleotides retain the ability to hybridize DNA or RNA and that they can be used by the appropriate enzymes if necessary. Examples of modified oligonucleotides can include but are not limited to: peptide nucleic acid molecules, phosphorothioate and methylphosphonate modifications. The term oligonucleotide when used below refers to natural and modified oligonucleotides.

The following are examples for employing allele-specific capture of DNA or RNA for the subsequent determination of multiple sequence variations (e.g., haplotypes), such as by using the base-specific fragmentation methods provided herein:

1. A biotinylated oligonucleotide directed against a site that is heterozygous for a nucleotide variance, is allowed to hybridize to the target DNA or RNA under conditions that result in binding of the oligonucleotide to only one of the two alleles present in the sample. The length, the position of mismatch between the oligonucleotide and the target sequence, and the chemical make-up of the oligonucleotide can all be adjusted to maximize the allele-specific discrimination. Streptavidin on a solid support is used to remove the biotinylated oligonucleotide and any DNA or RNA associated by hybridization to the oligonucleotide. For example, allele 1 is specifically captured by hybridization of an oligonucleotide containing a T at the variance site. The target DNA or RNA from allele 1 is then disassociated from the primer and solid support under denaturing conditions. The isolated RNA or DNA from allele 1 can then be genotyped to determine the haplotype. Alternatively, the RNA or DNA remaining in the sample, allele 2, following capture and removal of allele 1 can be genotyped to determine the its haplotype.

2. The target DNA is incubated with two oligonucleotides, one of which is biotinylated. If RNA is to be used in this example it must first be converted to cDNA. The oligonucleotides are designed to hybridize adjacent to one another at the site of variance. For example, the 3' end of the biotinylated oligonucleotide hybridizes one base 5' of the variant base. The other oligonucleotide hybridizes adjacent to the biotinylated primer with the 5' most oligonucleotide hybridizing to the variant base. If there is a perfect match at the site of variance (allele 1), the two primers are ligated together. If there is a mismatch at the site of variance (allele 2) no ligation occurs. The sample is then allowed to bind to the streptavidin on the solid support under conditions which are permissive for the hybridization of the ligated oligonucleotides but non-permissive for the hybridization of the shorter non-ligated oligonucleotides. The captured oligonucleotides and hybridized target DNA are removed from the sample, and the target DNA is eluted from the solid support and genotyped to determine haplotype. Alternatively, the allele 2 can be genotyped to determine haplotype after removal of allele 1 from the sample.

The size of the oligonucleotides can be varied in order to increase the likelihood that hybridization and ligation only occur when the correct allele is present. The ligation can be done under conditions that only allow the hybridization of a shorter oligonucleotide if it is hybridized next to the perfectly matched oligonucleotide and can make use of the stacking energy for stabilization. Also, either the biotinylated oligonucleotide or the other oligonucleotide can contain the mismatch. The biotin can also be put on the 5' or 3' end of the oligonucleotide as long as it is not at the site of ligation.

3. An oligonucleotide is hybridized to the target DNA in which the 3' end of the oligonucleotide is just 5' of the variant base. If RNA is to be used in this example it is first converted to cDNA. The sample is then incubated in the presence of four dideoxy nucleotides with a polymerase capable of extending the primer by incorporating dideoxy nucleotides where one of the dideoxy nucleotides contains a biotin. The biotinylated dideoxy nucleotide is selected to correspond to one of the variant bases such that it is incorporated only if the correct base is at the site of variance. For example, the base chosen is biotin ddTTP that is incorporated only when the primer anneals to allele 1. The primer with the incorporated biotinylated dideoxy nucleotide hybridized to allele 1 is separated from the rest of the DNA in the sample using streptavidin on a solid support. The isolated allele 1 can then be eluted from the solid support and genotyped to determine haplotype. As above, allele 2 which is left in the sample after capture and removal of allele 1, can also be genotyped to determine haplotype.

The dideoxy and biotinylated nucleotide do not have to be the same nucleotide. The primer can be extended in the presence of one biotinylated nucleotide, one dideoxy nucleotide and two normal nucleotides. For example, a biotinylated dTTP and a normal dGTP are added in with another normal nucleotide (not dTTP or dGTP) and a dideoxy nucleotide (not ddTTP or ddGTP). The dideoxy nucleotide are chosen so that the extension reaction are terminated before the occurrence of another site for the incorporation of the biotinylated dTTP. Extension from the primer on allele 1 results in the incorporation of a biotinylated dTTP. Extension from the primer on allele 2 results in the incorporation of a normal dGTP. Streptavidin on a solid support can be used to separate allele 1 from allele 2 for genotyping to determine haplotype.

C. METHODS OF GENERATING NUCLEIC ACID FRAGMENTS AT SPECIFIC AND PREDICTABLE SITES

Methods for detecting known mutations, SNPs, or other kinds of sequence variations (e.g., insertions, deletions, errors in sequence determination) or for discovering new mutations SNPs or sequence variations by specific cleavage are provided. In these methods, fragments that are cleaved at a specific position in a target biomolecule sequence based on (i) the sequence specificity of the cleaving reagent (e.g., for nucleic acids, the base specificity such as single bases A, G, C, T or U, or the recognition of modified single bases or nucleotides, or the recognition of short, between about two to about twenty base, non-degenerate as well as degenerate oligonucleotide sequences); or (ii) the structure of the target biomolecule; or (iii) physical processes, such as ionization by collision-induced dissociation during mass spectrometry; or (iv) a combination thereof, are generated from the target biomolecule. The analysis of fragments rather than the full length biomolecule shifts the mass of the ions to be determined into a lower mass range, which is generally more amenable to mass spectrometric detection. For example, the shift to smaller masses increases mass resolution, mass accuracy and, in particular, the sensitivity for detection. The actual molecular weights of the fragments of the target biomolecule as determined by mass spectrometry provide sequence information (e.g., the presence and/or identity of a mutation). The methods provided herein can be used to detect a plurality of sequence variations in a target biomolecule.

The fragment molecular weight pattern, i.e., mass signals of fragments that are generated from the target biomolecule is compared to the actual or simulated pattern of fragments generated under the same cleavage conditions for a reference sequence. The reference sequence usually corresponds to the target sequence, with the exception that the sequence variations (mutations, polymorphisms) to be identified in the target sequence, are not present in the reference sequence. For example, if the biomolecule is a nucleic acid, the reference nucleic acid sequence can be derived from a wild-type allele, whereas the target nucleic acid sequence can be derived from a mutant allele. As another example, the reference nucleic acid sequence can be a sequence from the human genome, whereas the target nucleic acid sequence can be a sequence from an infectious organism, such as a pathogen. The differences in mass signals between the target sequence and the reference sequence are then analyzed to determine the sequence variations that are most likely to be present in the target biomolecule sequence. The difference in mass signals between the target sequence and the reference sequence can be absolute (i.e., a mass signal that is present in the fragmentation spectrum of one sequence but not the other), or it can be relative, such as, but not limited to, differences in peak intensities (height, area, signal-to-noise or combinations thereof) of the signals.

The methods provided herein can be used to screen nucleic acid sequences of up to and greater than 2000 bases for the presence of sequence variations relative to a reference sequence. Further, the sequence variations are detected with greater accuracy due to the reduced occurrence of base-calling errors, which proves especially useful for the detection of "true" SNPs, such as SNPs in the coding region of a gene that results in an amino acid change, which usually have allele frequencies of less than 5% (see, e.g., L. Kruglyak et al., *Nat. Genet.*, 27:234 (2001)).

In the methods provided herein, the differences in mass signals between the fragments that are obtained by specific cleavage of the target nucleic acid sequence and those obtained by actual or simulated specific cleavage of the reference nucleic acid sequence under the same conditions are identified ("additional" or "missing" mass signals in the target nucleic acid fragment spectrum), and the masses of the fragments corresponding to these differences are determined. The set of differences can include, in addition to "missing" or "additional" signals in the target fragmentation pattern, signals of differing intensities or signal to noise ratios between the target and reference sequences. Once the masses of the fragments corresponding to differences between the target sequence and the reference sequence are determined ("different" fragments), one or more nucleic acid base compositions (compomers) are identified whose masses differ from the actual measured mass of each different fragment by a value that is less than or equal to a sufficiently small mass difference. These compomers are called witness compomers. The value of this sufficiently small mass difference is determined by parameters such as, but not limited to, the mass of the different fragment, the peak separation between fragments whose masses differ by a single nucleotide in type or length, and the absolute resolution of the mass spectrometer. Cleavage reactions specific for one or more of the four nucleic acid bases (A, G, C, T or U for RNA, or modifications thereof) can be used to generate data sets comprising the possible witness compomers for each specifically cleaved fragment that nears or is equal to the measured mass of each different fragment by a value that is less than or equal to the sufficiently small mass difference.

The generated witness compomers for each different fragment can then be used to determine the presence of SNPs or other sequence variations (e.g., insertions, deletions, substitutions) in the target nucleic acid sequence.

The possible witness compomers corresponding to the different fragments can be manually analyzed to obtain sequence variations corresponding to the compomers. In another aspect, mathematical algorithms are provided to reconstruct the target sequence variations from possible witness compomers of the different fragments. In a first step, all possible compomers whose masses differ by a value that is less than or equal to a sufficiently small mass difference from the actual mass of each different fragment generated in either the target nucleic acid or the reference nucleic acid cleavage reaction relative to the other under the same cleavage conditions, are identified. These compomers are the 'compomer witnesses'. The algorithm then determines all sequence variations that lead to the identified compomer witnesses. The algorithm constructs those sequence variations of the target sequence relative to a reference sequence that contains at most k mutations, polymorphisms, or other sequence variations, including, but not limited to, sequence variations between organisms, insertions, deletions and substitutions.

The value of k, the sequence variation order, is dependent on a number of parameters including, but not limited to, the expected type and number of sequence variations between a reference sequence and the target sequence, e.g., whether the sequence variation is a single base or multiple bases, or whether sequence variations are present at one location or at more than one location on the target sequence relative to the reference sequence. For example, for the detection of SNPs, the value of k is usually, although not necessarily, 1 or 2. For the detection of mutations and in resequencing, the value of k is usually, although not necessarily, 3 or higher. The sequences representing possible sequence variations contained in the target sequence relative to the reference sequence are called sequence variation candidates. The possible sequence variations that are detected in the target sequence are usually the sum of all sequence variations for which specific cleavage generates a witness compomer corresponding to each sequence variation.

A second algorithm is used to generate a simulated spectrum for each computed output sequence variation candidate. The simulated spectrum for each sequence variation candidate is scored, using a third (scoring) algorithm, against the actual spectrum for the target nucleic acid sequence. The value of the scores (the higher the score, the better the match, with the highest score usually being the sequence variation that is most likely to be present) can then be used to determine the sequence variation candidate that corresponds to the actual target nucleic acid sequence. The output of sequence variation candidates includes all sequence variations of the target sequence relative to the reference sequence that generates a different fragment in a specific cleavage reaction. For sequence variations in the target sequence that do not interact with each other, i.e., the separation (distance) between sequence variations along the target sequence is sufficient for each sequence variation to generate a distinct different fragment (of the target sequence relative to the reference sequence) in a specific cleavage reaction, the differences in the fragmentation pattern of the target sequence relative to the reference sequence represents the sum of all sequence variations in the target sequence relative to the reference sequence.

When a plurality of target sequences are analyzed against the same reference sequence, the algorithm can combine the scores of those target sequences that correspond to the same sequence variation candidate. Thus, an overall score for the sequence variation candidate representing the actual sequence variation can be determined. This embodiment is particularly useful, for example, in SNP discovery.

The sequence variation candidate output can be further used in an iterative process to detect additional sequence variations in the target sequence. For example, in the iterative process of detecting more than one sequence variation in a target sequence, the sequence variation with the highest score is accepted as an actual sequence variation, and the signal or peak corresponding to this sequence variation is added to the reference fragment spectrum to generate an updated reference fragment spectrum. All remaining sequence variation candidates are then scored against this updated reference fragment spectrum to output the sequence variation candidate with the next highest score. This second sequence variation candidate can also represent a second actual sequence variation in the target sequence. Therefore, the peak corresponding to the second sequence variation can be added to the reference fragment spectrum to generate a second updated reference spectrum against which a third sequence variation can be detected according to its score. This process of iteration can be repeated until no more sequence variation candidates representing actual sequence variations in the target sequence are identified.

In one embodiment, provided herein is a method for determining allelic frequency in a sample by cleaving a mixture of target nucleic acid molecules in the sample containing a mixture of wild-type and mutant alleles into fragments using one or more specific cleavage reagents; cleaving or simulating cleavage of a nucleic acid molecule containing a wild-type allele into fragments using the same one or more cleavage reagents; determining the masses of the fragments; identifying differences in fragments between the target nucleic acid molecule and the wild-type nucleic acid molecule that are representative of sequence variations in the mixture of target nucleic acid molecules relative to the wild-type nucleic acid molecule; determining the different fragments that are compomer witnesses; determining the set of bounded compomers of sequence variation order k corresponding to each compomer witness; determining the allelic variants that are candidate alleles for each bounded compomer; scoring the candidate alleles; and determining the allelic frequency of the mutant alleles in the sample.

In other embodiments, the methods provided herein can be used for detecting sequence variations in a target nucleic acid in a mixture of nucleic acids in a biological sample. Biological samples include but are not limited to DNA from a pool of individuals, or a homogeneous tumor sample derived from a single tissue or cell type, or a heterogeneous tumor sample containing more than one tissue type or cell type, or a cell line derived from a primary tumor. Also contemplated are methods, such as haplotyping methods, in which two mutations in the same gene are detected.

In other embodiments, a plurality of target nucleic acids can be multiplexed in a single reaction measurement by fragmenting each target nucleic acid and one or more reference nucleic acids in the same cleavage reactions using one or more cleavage reagent. These methods are particularly useful when differences in fragmentation patterns between one or more target nucleic acids relative to one or more reference nucleic acids using one or more specific cleavage reagents are simultaneously analyzed.

In one embodiment, the fragments generated according to the methods provided herein are analyzed for the presence of sequence variations relative to a reference sequence, and the analyzed fragment sequences are ordered to provide the sequence of the larger target nucleic acid. The fragments can be generated by partial or total cleavage, using a single specific cleavage reaction or complementary specific cleavage reactions such that alternative fragments of the same target biomolecule sequence are obtained. The cleavage means can be enzymatic, chemical, physical or a combination thereof, as long as the site of cleavage can be identified.

The target nucleic acids can be selected from among single-stranded DNA, double-stranded DNA, cDNA, single-stranded RNA, double-stranded RNA, DNA/RNA hybrid, PNA (peptide nucleic acid) and a DNA/RNA mosaic nucleic acid. The target nucleic acids can be directly isolated from a biological sample, or can be derived by amplification or cloning of nucleic acid sequences from a biological sample. The amplification can be achieved by polymerase chain reaction (PCR), reverse transcription followed by the polymerase chain reaction (RT-PCR), strand displacement amplification (SDA), rolling circle amplification and transcription based processes.

Nucleic Acid Fragmentation

Fragmentation of nucleic acids is known in the art and can be achieved in many ways. For example, polynucleotides composed of DNA, RNA, analogs of DNA and RNA or combinations thereof, can be fragmented physically, chemically, or enzymatically, as long as the fragmentation is obtained by cleavage at a specific site in the target nucleic acid. Fragments can be cleaved at a specific position in a target nucleic acid sequence based on (i) the base specificity of the cleaving reagent (e.g., A, G, C, T or U, or the recognition of modified bases or nucleotides); or (ii) the structure of the target nucleic acid; or (iii) a combination thereof, are generated from the target nucleic acid. Fragments can vary in size, and suitable fragments are typically less than about 2000 nucleic acids. Suitable fragments can fall within several ranges of sizes including but not limited to: less than about 1000 bases, between about 100 to about 500 bases, or from about 25 to about 200 bases, between about 15 to about 100 bases, between about 10 to about 75 bases, between about 5 to about 50 bases, between about 3 to about 30 bases, between about 2 to about 20 bases. In some aspects, fragments of about one nucleic acid are desirable.

Polynucleotides can be fragmented by chemical reactions including for example, hydrolysis reactions including base and acid hydrolysis. Alkaline conditions can be used to fragment polynucleotides comprising RNA because RNA is unstable under alkaline conditions. See, e.g., Nordhoff et al. *Ion stability of nucleic acids in infrared matrix-assisted laser desorption/ionization mass spectrometry, Nucl. Acids Res.,* 21(15):3347-57 (1993). DNA can be hydrolyzed in the presence of acids, typically strong acids such as 6M HCl. The temperature can be elevated above room temperature to facilitate the hydrolysis. Depending on the conditions and length of reaction time, the polynucleotides can be fragmented into various sizes including single base fragments. Hydrolysis can, under rigorous conditions, break both of the phosphate ester bonds and also the N-glycosidic bond between the deoxyribose and the purines and pyrimidine bases.

An exemplary acid/base hydrolysis protocol for producing polynucleotide fragments is described in Sargent et al., *Methods Enzymol.,* 152:432 (1988). Briefly, 1 g of DNA is dissolved in 50 mL of 0.1 N NaOH. 1.5 mL concentrated HCl is added, and the solution is mixed quickly. DNA precipitates immediately, and should not be stirred for more than a few seconds to prevent formation of a large aggregate. The sample is incubated at room temperature for 20 minutes to partially depurinate the DNA. Subsequently, 2 mL of 10 N NaOH(OH- concentration to 0.1 N) is added, and the sample is stirred until DNA redissolves completely. The sample is then incubated at 65° C. for 30 minutes to hydrolyze the DNA. Typical sizes range from about 250-1000 nucleotides but can vary lower or higher depending on the conditions of hydrolysis. Another process whereby nucleic acid molecules are chemically cleaved in a base-specific manner is provided by A. M. Maxam and W. Gilbert, *Proc. Natl. Acad. Sci. USA* 74:560-64 (1977), and incorporated by reference herein. Individual reactions were devised to cleave preferentially at guanine, at adenine, at cytosine and thymine, and at cytosine alone.

Polynucleotides can also be cleaved via alkylation, particularly phosphorothioate-modified polynucleotides. K. A. Browne, *Metal ion-catalyzed nucleic Acid alkylation and fragmentation, J. Am. Chem. Soc.* 124(27):7950-62 (2002). Alkylation at the phosphorothioate modification renders the polynucleotide susceptible to cleavage at the modification site. I. G. Gut and S. Beck describe methods of alkylating DNA for detection in mass spectrometry. I. G. Gut and S. Beck, *A procedure for selective DNA alkylation and detection by mass spectrometry. Nucleic Acids Res.* 23(8):1367-73 (1995). Another approach uses the acid lability of P3'-N5'-phosphoroamidate-containing DNA (Shchepinov et al., "Matrix-induced fragmentation of P3'-N5'-phosphoroamidate-containing DNA: high-throughput MALDI-TOF analysis of genomic sequence polymorphisms," *Nucleic Acids Res.* 25:3864-3872 (2001). Either dCTP or dTTP are replaced by their analog P-N modified nucleoside triphosphates and are introduced into the target sequence by primer extension reaction subsequent to PCR. Subsequent acidic reaction conditions produce base-specific cleavage fragments. In order to minimize depurination of adenine and guanine residues under the acidic cleavage conditions required, 7-deaza analogs of dA and dG can be used.

Single nucleotide mismatches in DNA heteroduplexes can be cleaved by the use of osmium tetroxide and piperidine, providing an alternative strategy to detect single base substitutions, generically named the "Mismatch Chemical Cleavage" (MCC) (Gogos et al., *Nucl. Acids Res* 18:6807-6817 (1990)).

Polynucleotide fragmentation can also be achieved by irradiating the polynucleotides. Typically, radiation such as gamma or x-ray radiation is sufficient to fragment the polynucleotides. The size of the fragments can be adjusted by adjusting the intensity and duration of exposure to the radiation. Ultraviolet radiation can also be used. The intensity and duration of exposure can also be adjusted to minimize undesirable effects of radiation on the polynucleotides. Boiling polynucleotides can also produce fragments. Typically a solution of polynucleotides is boiled for a couple hours under constant agitation. Fragments of about 500 bp can be achieved. The size of the fragments can vary with the duration of boiling.

Polynucleotide fragments can result from enzymatic cleavage of single or multi-stranded polynucleotides. Multi-stranded polynucleotides include polynucleotide complexes comprising more than one strand of polynucleotides, including for example, double and triple stranded polynucleotides. Depending on the enzyme used, the polynucleotides are cut nonspecifically or at specific nucleotides sequences. Any enzyme capable of cleaving a polynucleotide can be used including but not limited to endonucleases, exonucleases, ribozymes, and DNAzymes. Enzymes useful for fragmenting polynucleotides are known in the art and are commercially available. See, for example, Sambrook, J., Russell, D. W., *Molecular Cloning: A Laboratory Manual*, the third edition, Cold Spring Harbor Laboratory Press, Cold Spring Harbor, N.Y., 2001, which is incorporated herein by reference. Enzymes can also be used to degrade large polynucleotides into smaller fragments.

Endonucleases are an exemplary class of enzymes useful for fragmenting polynucleotides. Endonucleases have the capability to cleave the bonds within a polynucleotide strand. Endonucleases can be specific for either double-stranded or single-stranded polynucleotides. Cleavage can occur randomly within the polynucleotide or can cleave at specific sequences. Endonucleases which randomly cleave double-strand polynucleotides often make interactions with the backbone of the polynucleotide. Specific fragmentation of polynucleotides can be accomplished using one or more enzymes in sequential reactions or contemporaneously. Homogenous or heterogenous polynucleotides can be cleaved. Cleavage can be achieved by treatment with nuclease enzymes provided from a variety of sources including the Cleavase™ enzyme, Taq DNA polymerase, *E. coli* DNA polymerase I and eukaryotic structure-specific endonucleases, murine FEN-1 endonucleases (Harrington and Liener, (1994) Genes and Develop. 8:1344) and calf thymus 5' to 3' exonuclease (Murante, R. S., et al., *J. Biol. Chem.* 269:1191 (1994)). In addition, enzymes having 3' nuclease activity such as members of the family of DNA repair endonucleases (e.g., the Rrp1 enzyme from *Drosophila melanogaster*, the yeast RAD1/RAD10 complex and *E. coli* Exo III), can also be used for enzymatic cleavage.

Restriction endonucleases are a subclass of endonucleases which recognize specific sequences within double-strand polynucleotides and typically cleave both strands either within or close to the recognition sequence. One commonly used enzyme in DNA analysis is HaeIII, which cuts DNA at the sequence 5'-GGCC-3'. Other exemplary restriction endonucleases include Acc I, Afl III, Alu I, Alw44 I, Apa I, Asn I, Ava I, Ava II, BamH I, Ban II, Bcl I, Bgl I. Bgl II, Bin I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I. The cleavage sites for these enzymes are known in the art.

Restriction enzymes are divided into types 1, II, and Ill. Type I and type II enzymes carry modification and ATP-dependent cleavage in the same protein. Type III enzymes cut DNA at a recognition site and then dissociate from the DNA. Type I enzymes cleave at random sites within the DNA. Any class of restriction endonucleases can be used to fragment polynucleotides. Depending on the enzyme used, the cut in the polynucleotide can result in one strand overhanging the other also known as "sticky" ends. BamHI generates cohesive 5' overhanging ends. KpnI generates cohesive 3' overhanging ends. Alternatively, the cut can result in "blunt" ends that do not have an overhanging end. DraI cleavage generates blunt ends. Cleavage recognition sites can be masked, for example by methylation, if needed. Many of the known restriction endonucleases have 4 to 6 base-pair recognition sequences (Eckstein and Lilley (eds.), *Nucleic Acids and Molecular Biology*, vol. 2, Springer-Verlag, Heidelberg (1988)).

A small number of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, *Trends Genet.* 3:167 (1987)). Recently, endonucleases encoded by group I introns have been discovered that might have greater than 12 base-pair specificity (Perlman and Butow, *Science* 246:1106 (1989)).

Restriction endonucleases can be used to generate a variety of polynucleotide fragment sizes. For example, CviJ1 is a restriction endonuclease that recognizes between a two and three base DNA sequence. Complete digestion with CviJ1 can result in DNA fragments averaging from 16 to 64 nucleotides in length. Partial digestion with CviJ1 can therefore fragment DNA in a "quasi" random fashion similar to shearing or sonication. CviJI normally cleaves RGCY sites between the G and C leaving readily cloneable blunt ends, wherein R is any purine and Y is any pyrimidine. In the presence of 1 mM ATP and 20% dimethyl sulfoxide the specificity of cleavage is relaxed and CviJI also cleaves RGCN and YGCY sites. Under these "star" conditions, CviJI cleavage generates quasi-random digests. Digested or sheared DNA can be size selected at this point.

Methods for using restriction endonucleases to fragment polynucleotides are widely known in the art. In one exemplary protocol a reaction mixture of 20-50 μl is prepared containing: DNA 1-3 μg; restriction enzyme buffer 1×; and a restriction endonuclease 2 units for 1 μg of DNA. Suitable buffers also are known in the art and include suitable ionic strength, cofactors, and optionally, pH buffers to provide optimal conditions for enzymatic activity. Specific enzymes can require specific buffers which are generally available from commercial suppliers of the enzyme. An exemplary buffer is potassium glutamate buffer (KGB). Hannish, J. and M. McClelland. (1988). *Activity of DNA modification and restriction enzymes in KGB, a potassium glutamate buffer. Gene Anal. Tech.* 5:105; McClelland, M. et al., *A single buffer for all restriction endonucleases, Nucleic Acid Res.* 16:364 (1988). The reaction mixture is incubated at 37° C. for 1 hour or for any time period needed to produce fragments of a desired size or range of sizes. The reaction can be stopped by heating the mixture at 65° C. or 80° C. as needed. Alternatively, the reaction can be stopped by chelating divalent cations such as $Mg^{2+}$ with for example, EDTA.

More than one enzyme can be used to fragment the polynucleotide. Multiple enzymes can be used in sequential reactions or in the same reaction provided the enzymes are active under similar conditions such as ionic strength, temperature, or pH. Typically, multiple enzymes are used with a standard buffer such as KGB. The polynucleotides can be partially or completely digested. Partially digested means only a subset of the restriction sites are cleaved. Complete digestion means all of the restriction sites are cleaved.

Endonucleases can be specific for certain types of polynucleotides. For example, endonuclease can be specific for DNA or RNA. Ribonuclease H is an endoribonuclease that specifically degrades the RNA strand in an RNA-DNA hybrid. Ribonuclease A is an endoribonuclease that specifically attacks single-stranded RNA at C and U residues. Ribonuclease A catalyzes cleavage of the phosphodiester bond between the 5'-ribose of a nucleotide and the phosphate group attached to the 3'-ribose of an adjacent pyrimidine nucleotide. The resulting 2',3'-cyclic phosphate can be hydrolyzed to the corresponding 3'-nucleoside phosphate. RNase T1 digests RNA at only G ribonucleotides and RNase $U_2$ digests RNA at only A ribonucleotides. The use of mono-specific RNases such as RNase $T_1$ (G specific) and RNase $U_2$ (A specific) has become routine (Donis-Keller et al., *Nucleic Acids Res.* 4:2527-2537 (1977); Gupta and Randerath, *Nucleic Acids Res.* 4:1957-1978 (1977); Kuchino and Nishimura, *Methods Enzymol.* 180:154-163 (1989); and Hahner et al., *Nucl. Acids Res.* 25(10):1957-1964 (1997)). Another enzyme, chicken liver ribonuclease (RNase CL3) has been reported to cleave preferentially at cytidine, but the enzyme's proclivity for this base has been reported to be affected by the reaction conditions (Boguski et al., *J. Biol. Chem.* 255:2160-2163 (1980)). Recent reports also claim cytidine specificity for another ribonuclease, cusativin, isolated from dry seeds of *Cucumis sativus* L (Rojo et al., *Planta* 194:328-338 (1994)). Alternatively, the identification of pyrimidine residues by use of RNase PhyM (A and U specific) (Donis-Keller, H. *Nucleic Acids Res.* 8:3133-3142 (1980)) and RNase A (C and U specific) (Simoncsits et al., *Nature* 269:833-836 (1977); Gupta and Randerath, *Nucleic Acids Res.* 4:1957-1978 (1977)) has been demonstrated. In order to reduce ambiguities in sequence determination, additional limited alkaline hydrolysis can be performed. Since every phosphodiester bond is potentially cleaved under these conditions, information about omitted and/or unspecific cleavages can be obtained this way (Donis-Keller et al., *Nucleic Acids Res.* 4:2527-2537 (1977)). Benzonase™, nuclease P1, and phosphodiesterase I are nonspecific endonucleases that are suitable for generating polynucleotide fragments ranging from 200 base pairs or less. Benzonase™ (Novagen, Madison, Wis.) is a genetically engineered endonuclease which degrades all forms of DNA and RNA (single-stranded, double-stranded, linear and circular) and can be used in a wide range of operating conditions. The enzyme completely digests nucleic acids to 5'-monophosphate terminated oligonucleotides 2-5 bases in length. The nucleotide and amino acid sequences for Benzonase™ are provided in U.S. Pat. No. 5,173,418.

DNA glycosylases specifically remove a certain type of nucleobase from a given DNA fragment, which results in an abasic site. These enzymes can thereby produce abasic sites, which can be recognized either by another cleavage enzyme, cleaving the exposed phosphate backbone specifically at the abasic site and producing a set of nucleobase specific fragments indicative of the sequence, or by chemical means, such as alkaline solutions and or heat. The use of one combination of a DNA glycosylase and its targeted nucleotide are sufficient to generate a base specific signature pattern of any given target region.

Numerous DNA glycosylases are known. For example, a DNA glycosylase can be uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase (see, e.g., U.S. Pat. Nos. 5,536,649; 5,888,795; 5,952,176; 6,099,553; and 6,190,865 B1; International PCT application Nos. WO 97/03210, WO 99/54501; see, also, Eftedal et al. *Nucleic Acids Res.* 21:2095-2101 (1993), Bjelland and Seeberg *Nucleic Acids Res.* 15:2787-2801 (1987), Saparbaev et al. *Nucleic Acids Res.* 23:3750-3755 (1995), Bessho *Nucleic Acids Res.* 27:979-983 (1999)) corresponding to the enzyme's modified nucleotide or nucleotide analog target.

Uracil, for example, can be incorporated into an amplified DNA molecule by amplifying the DNA in the presence of normal DNA precursor nucleotides (e.g., dCTP, dATP, and dGTP) and dUTP. When the amplified product is treated with UDG, uracil residues are cleaved. Subsequent chemical treatment of the products from the UDG reaction results in the cleavage of the phosphate backbone and the generation of nucleobase specific fragments. Moreover, the separation of the complementary strands of the amplified product prior to glycosylase treatment allows complementary patterns of fragmentation to be generated. Thus, the use of dUTP and Uracil DNA glycosylase allows the generation of T-specific fragments for the complementary strands, thus providing information on the T as well as the A positions within a given sequence. A C-specific reaction on both (complementary) strands (i.e., with a C-specific glycosylase) yields information on C as well as G positions within a given sequence if the fragmentation patterns of both amplification strands are analyzed separately. With the glycosylase method and mass spectrometry, a full series of A, C, G and T base-specific fragmentation patterns can be analyzed in the methods provided herein.

Several methods exist where treatment of DNA with specific chemicals modifies existing bases so that they are recognized by specific DNA glycosylases. For example, treatment of DNA with alkylating agents such as methylnitrosourea generates several alkylated bases including N3 methyladenine and N3-methylguanine which are recognized and cleaved by alkyl purine DNA-glycosylase. Treatment of DNA with sodium bisulfite causes deamination of cytosine residues in DNA to form uracil residues in the DNA which can be cleaved by uracil N-glycosylase (also known as uracil DNA-glycosylase). Chemical reagents can also convert guanine to its oxidized form, 8-hydroxyguanine, which can be cleaved by formamidopyrimidine DNA N-glycosylase (FPG protein) (Chung et al., "An endonuclease activity of *Escherichia coli* that specifically removes 8-hydroxyguanine residues from DNA," *Mutation Research* 254:1-12 (1991)). The use of mismatched nucleotide glycosylases have been reported for cleaving polynucleotides at mismatched nucleotide sites for the detection of point mutations (Lu, A-L and Hsu, I-C, *Genomics* 14:249-255 (1992) and Hsu, I-C., et al., *Carcinogenesis* 14:1657-1662 (1994)). The glycosylases used include the *E. coli* Mut Y gene product which releases the mispaired adenines of A/G mismatches efficiently, and releases A/C mismatches albeit less efficiently, and human thymidine DNA glycosylase which cleaves at Gfr mismatches. Fragments are produced by glycosylase treatment and subsequent cleavage of the abasic site.

Fragmentation of nucleic acids for the methods as provided herein can also be accomplished by dinucleotide ("2 cutter") or relaxed dinucleotide ("1 and ½ cutter," e.g.) cleavage specificity. Dinucleotide-specific cleavage reagents are known to those of skill in the art and are incorporated by reference herein (see, e.g., WO 94/21663; Cannistraro et al., *Eur. J. Biochem.* 181:363-370 (1989); Stevens et al., *J. Bacteriol.* 164:57-62 (1985); Marotta et al., *Biochemistry* 12:2901-2904 (1973)). Stringent or relaxed dinucleotide-specific cleavage can also be engineered through the enzymatic and chemical modification of the target nucleic acid. For example, transcripts of the target nucleic acid of interest can be synthesized with a mixture of regular and α-thio-substrates and the phosphorothioate internucleoside linkages can subsequently be modified by alkylation using reagents such as an alkyl halide (e.g., iodoacetamide, iodoethanol) or 2,3-epoxy-1-propanol. The phosphotriester bonds formed by such modification are not expected to be substrates for RNAses. Using this procedure, a mono-specific RNAse, such as RNAse-T1, can be made to cleave any three, two or one out of the four possible GpN bonds depending on which substrates are used in the α-thio form for target preparation. The repertoire of useful dinucleotide-specific cleavage reagents can be further expanded by using additional RNAses, such as RNAse-U2 and RNAse-A. In the case of RNAse A, for example, the cleavage specificity can be restricted to CpN or UpN dinucleotides through enzymatic incorporation of the 2'-modified form of appropriate nucleotides, depending on the desired cleavage specificity. Thus, to make RNAse A specific for CpG nucleotides, a transcript (target molecule) is prepared by incorporating αS-dUTP, αS-ATP, αS-CTP and GTP nucleotides. These selective modification strategies can also be used to prevent cleavage at every base of a homopolymer tract by selectively modifying some of the nucleotides within the homopolymer tract to render the modified nucleotides less resistant or more resistant to cleavage.

DNAses can also be used to generate polynucleotide fragments. Anderson, S., *Shotgun DNA sequencing using cloned DNase I-generated fragments. Nucleic Acids Res.* 9:3015-3027 (1981). DNase I (Deoxyribonuclease I) is an endonuclease that digests double- and single-stranded DNA into poly- and mono-nucleotides. The enzyme is able to act upon single as well as double-stranded DNA and on chromatin.

Deoxyribonuclease type II is used for many applications in nucleic acid research including DNA sequencing and digestion at an acidic pH. Deoxyribonuclease II from porcine spleen has a molecular weight of 38,000 daltons. The enzyme is a glycoprotein endonuclease with dimeric structure. Optimum pH range is 4.5-5.0 at ionic strength 0.15 M. Deoxyribonuclease II hydrolyzes deoxyribonucleotide linkages in native and denatured DNA yielding products with 3'-phosphates. It also acts on p-nitrophenylphosphodiesters at pH 5.6-5.9. Ehrlich, S. D. et al., *Studies on acid deoxyribonuclease. IX. 5'-Hydroxy-terminal and penultimate nucleotides of oligonucleotides obtained from calf thymus deoxyribonucleic acid. Biochemistry* 10(11):2000-9 (1971).

Large single-stranded polynucleotides can be fragmented into small polynucleotides using nucleases that remove various lengths of bases from the end of a polynucleotide. Exemplary nucleases for removing the ends of single-stranded polynucleotides include but are not limited to S1, Bal 31, and mung bean nucleases. For example, mung bean nuclease degrades single-stranded DNA to mono- or polynucleotides with phosphate groups at their 5' termini. Double-stranded nucleic acids can be digested completely if exposed to very large amounts of this enzyme.

Exonucleases are proteins that also cleave nucleotides from the ends of a polynucleotide, for example a DNA molecule. There are 5' exonucleases (cleave the DNA from the 5'-end of the DNA chain) and 3' exonucleases (cleave the DNA from the 3'-end of the chain). Different exonucleases can hydrolyse single-strand or double-strand DNA. For example, Exonuclease III is a 3' to 5' exonuclease, releasing 5'-mononucleotides from the 3'-ends of DNA strands; it is a DNA 3'-phosphatase, hydrolyzing 3'-terminal phosphomonoesters; and it is an AP endonuclease, cleaving phosphodiester bonds at apurinic or apyrimidinic sites to produce 5'-termini that are base-free deoxyribose 5'-phosphate residues. In addition, the enzyme has an RNase H activity; it preferentially degrades the RNA strand in a DNA-RNA hybrid duplex, presumably exonucleolytically. In mammalian cells, the major DNA 3'-exonuclease is DNase III (also called TREX-1). Thus, fragments can be formed by using exonucleases to degrade the ends of polynucleotides.

Catalytic DNA and RNA are known in the art and can be used to cleave polynucleotides to produce polynucleotide fragments. Santoro, S. W. and Joyce, G. F., *A general purpose RNA-cleaving DNA enzyme, Proc. Natl. Acad. Sci. USA* 94:4262-4266 (1997). DNA as a single-stranded molecule can fold into three dimensional structures similar to RNA, and the 2'-hydroxy group is dispensable for catalytic action. As ribozymes, DNAzymes can also be made, by selection, to depend on a cofactor. This has been demonstrated for a histidine-dependent DNAzyme for RNA hydrolysis. U.S. Pat. Nos. 6,326,174 and 6,194,180 disclose deoxyribonucleic acid enzymes—catalytic or enzymatic DNA molecules—capable of cleaving nucleic acid sequences or molecules, particularly RNA. U.S. Pat. Nos. 6,265,167; 6,096,715; 5,646,020 disclose ribozyme compositions and methods and are incorporated herein by reference.

A DNA nickase, or DNase, can be used to recognize and cleave one strand of a DNA duplex. Numerous nickases are known. Among these, for example, are nickase NY2A nickase and NYS1 nickase (Megabase) with the following cleavage sites:

```
NY2A:      5'...R AG...3'
           3'...Y TC...5' where R = A or G and Y = C or T

NYS1:      5'... CC[A/G/T]...3'
           3'... GG[T/C/A]...5'.
```

Subsequent chemical treatment of the products from the nickase reaction results in the cleavage of the phosphate backbone and the generation of fragments.

The Fen-1 fragmentation method involves the enzymes Fen-1 enzyme, which is a site-specific nuclease known as a "flap" endonuclease (U.S. Pat. Nos. 5,843,669, 5,874,283, and 6,090,606). This enzyme recognizes and cleaves DNA "flaps" created by the overlap of two oligonucleotides hybridized to a target DNA strand. This cleavage is highly specific and can recognize single base pair mutations, permitting detection of a single homologue from an individual heterozygous at one SNP of interest and then genotyping that homologue at other SNPs occurring within the fragment. Fen-1 enzymes can be Fen-1 like nucleases e.g., human, murine, and *Xenopus* XPG enzymes and yeast RAD2 nucleases or Fen-1 endonucleases from, for example, *M. jannaschii, P. furiosus*, and *P. woesei*.

Another technique, which can be used as a diagnostic tool, such as for detecting the presence of *M. tuberculosis*, can be used to cleave DNA chimeras. Tripartite DNA-RNA-DNA probes are hybridized to target nucleic acids, such as *M. tuberculosis-specific* sequences. Upon the addition of RNAse H, the RNA portion of the chimeric probe is degraded, releasing the DNA portions (Yule, *Bio/Technology* 12:1335 (1994)).

Fragments can also be formed using any combination of fragmentation methods as well as any combination of enzymes. Methods for producing specific fragments can be combined with methods for producing random fragments. Additionally, one or more enzymes that cleave a polynucleotide at a specific site can be used in combination with one or more enzymes that specifically cleave the polynucleotide at a different site. In another example, enzymes that cleave specific kinds of polynucleotides can be used in combination, for example, an RNase in combination with a DNase. In still another example, an enzyme that cleaves polynucleotides randomly can be used in combination with an enzyme that cleaves polynucleotides specifically. Used in combination means performing one or more methods after another or contemporaneously on a polynucleotide.

Ionization Fragmentation Cleavage of Nucleic Acids

Ionization fragmentation of nucleic acids is accomplished during mass spectrometric analysis either by using higher voltages in the ionization zone of the mass spectrometer (MS) to fragment by tandem MS using collision-induced dissociation in the ion trap. (see, e.g., Bieman, *Methods in Enzymology*, 193:455-479 (1990)). The base sequence is deduced from the molecular weight differences observed in the resulting MS fragmentation pattern of the nucleic acid using the published masses associated with individual amino acid residues or nucleotide residues in the MS.

D. MASS ACQUISITION

Detecting the mass of the fragments generated at specific and predictable sites herein (e.g., by base-specific fragmentation) can be accomplished using any suitable mass detection format known to those of skill in the art, such as for example, mass spectrometry. Such formats include, but are not limited to, Matrix-Assisted Laser Desorption/Ionization, Time-of-Flight (MALDI-TOF), Electrospray ionization (ESi), IR-MALDI (see, e.g., published International PCT application No. 99/57318 and U.S. Pat. No. 5,118,937), Orthogonal-TOF (O-TOF), Axial-TOF (A-TOF), Ion Cyclotron Resonance (ICR), Fourier Transform, Linear/Reflectron (RETOF), Quadrupole mass spectrometry, Quadrupole ion trap mass spectrometry, and combinations thereof. See also, Aebersold and Mann, Mar. 13, 2003, *Nature* 422:198-207 (e.g., at FIG. 2); and Yates (1998) *J. of Mass Spec.* 33:1-19, for a review of exemplary methods for mass spectrometry suitable for use in the methods provided herein, which articles are incorporated herein in its entirety by reference. MALDI, particular UV and IR, and O-TOF are among exemplary formats for mass spectrometry.

For example, O-TOF instruments possess a number of attributes inherent to their design which make them ideally suited for coupling liquid separation techniques to Atmospheric Pressure Ionization (API). The first attribute is the fast acquisition rates achieved by O-TOF. Acquisition rates on the order of 10's of milliseconds are not uncommon. Thus, narrow peaks (<1 second FWHM) associated with separation techniques such as capillary electrophoresis (CE) can be easily profiled. Along with fast scan rates, O-TOF mass spectrometers also has the ability to see a very broad mass range (e.g., 0-6000 Da/spectra). In addition, these instruments possess excellent sensitivity since all the ions entering the analyzer region are accelerated to the detector at high repetition rates (e.g., 5 kHz).

In the methods provided herein, 4 spectra are obtained per fragmented amplified target nucleic acid and sample, wherein each spectra corresponds to 1 of the 4 particular base-specific fragmentation reactions. In other embodiments, 3 spectra are obtained per fragmented amplified target nucleic acid and sample, wherein each spectra corresponds to 1 of 3 selected particular base-specific fragmentation reactions. In other embodiments (as set forth in Examples 1.B and 1.C herein using RNAase A), 2 spectra are obtained per fragmented amplified target nucleic acid and sample, wherein each spectra corresponds to 1 of 2 selected particular base-specific fragmentation reactions.

E. TECHNIQUES FOR POLYMORPHISM, MUTATION AND SEQUENCE VARIATION DISCOVERY

Provided herein are techniques that increase the speed with which mutations, polymorphisms or other sequence variations can be detected in a target sequence, relative to a reference sequence. Previous methods of discovering known or unknown sequence variations in a target sequence relative to a reference sequence involved simulating, for every possible target sequence variation of the reference sequence (including substitutions, insertions, deletions, polymorphisms and species-dependent variations), a specific fragmentation spectrum that is generated by a given cleavage reagent or set of cleavage reagents for that particular target sequence. In such previous methods, each of the simulations generated by all possible sequence variations in the target sequence relative to the reference sequence were then compared against the actual fragmentation spectrum obtained for the target sequence, to determine the actual sequence variation that is present in the target sequence. The problem with such an approach is that the time and resources expended to generate simulations of all possible sequence variation candidates can be prohibitive.

One way to address this problem is to reduce the number of possible sequence variations of a given target sequence whose fragmentation patterns are simulated and compared against the actual fragmentation pattern generated by cleavage of the target sequence. In the methods provided herein, an algorithm is used to output only those sequence variation candidates that are most likely to have generated the actual fragmentation spectrum of the target sequence. A second algorithm then simulates only this subset of sequence variation candidates for comparison against the actual target sequence fragmentation spectrum. Thus, the number of sequence variations for simulation analyses is drastically reduced.

In the methods provided herein, in a first step, the fragments corresponding to differences in signals between a target sequence and a reference sequence that are absolute (presence or absence of a signal in the target spectrum relative to a reference spectrum) or quantitative (differences in signal intensities or signal to noise ratios) differences obtained by actual cleavage of the target sequence relative to actual or simulated cleavage of the reference sequence under the same conditions are identified, and the masses of these "different" target nucleic acid fragments are determined. Once the masses of the different fragments are determined, one or more nucleic acid base compositions (compomers) are identified whose masses differ from the actual measured mass of each different fragment by a value that is less than or equal to a sufficiently small mass difference. These compomers are called witness compomers. The value of the sufficiently small mass difference is determined by parameters such as the peak separation between fragments whose masses differ by a single nucleotide equivalent in type or length, and the absolute resolution of the mass spectrometer. Cleavage reactions specific for one or more of the four nucleic acid bases (A, G, C, T or U for RNA, or modifications thereof, or amino acids or modifications thereof for proteins) can be used to generate data sets comprising the possible witness compomers for each specifically cleaved fragment that nears or equals the measured mass of each different fragment by a value that is less than or equal to a sufficiently small mass difference.

The techniques provided herein can reconstruct the target sequence variations from possible witness compomers corresponding to differences between the fragments of the target nucleic acid relative to the reference nucleic acid.

Algorithm 1: FindSequenceVariationCandidates

This is the basic technique that is used to analyze the results from one or more specific cleavage reactions of a target nucleic acid sequence. The first step identifies all possible compomers whose masses differ by a value that is less than or equal to a sufficiently small mass difference from the actual mass of each different fragment generated in the target nucleic acid cleavage reaction relative to the same reference nucleic acid cleavage reaction. These compomers are the 'compomer witnesses'. For example, suppose a different fragment peak is detected at 2501.3 Da. The only natural compomer having a mass within, e.g., a +/−2 Da interval of the peak mass is $A_1C_4G_2T_1$ at 2502.6 Da. In the case of cleavage reactions that do not remove the recognized base (herein, T) at the cleavage site, (for example, UDG removes the cleaved base, but RNAse A does not) the recognition base is subtracted, resulting in the compomer $A_1C_4G_2$. Every compomer detected in this fashion is called a compomer witness.

The basic technique then determines all compomers that can be transformed into each compomer witness c' with at most k mutations, polymorphisms, or other sequence variations including, but not limited to, sequence variations between organisms. The value of k, the sequence variation order, is predefined by the user and is dependent on a number of parameters including, but not limited to, the expected type and number of sequence variations between a reference sequence and the target sequence, e.g., whether the sequence variation is a single base or multiple bases, whether sequence variations are present at one location or at more than one location on the target sequence relative to the reference sequence, or whether the sequence variations interact or do not interact with each in the target sequence. For example, for the detection of SNPs, the value of k is usually, although not necessarily, 1 or 2. As another example, for the detection of mutations and in resequencing, the value of k is usually, although not necessarily, 3 or higher.

A set of bounded compomers are constructed, which refers to the set of all compomers c that correspond to the set of subsequences of a reference sequence, with a boundary b that indicates whether or not cleavage sites are present at the two ends of each subsequence. The set of bounded compomers can be compared against possible compomer witnesses to construct all possible sequence variations of a target sequence relative to a reference sequence. Using the constructed pairs of compomer witnesses and bounded compomers, the algorithm then constructs all sequence variation candidates that lead to the obtained differences in the fragmentation pattern of a target sequence relative to a reference sequence under the same cleavage conditions.

The determination of sequence variation candidates significantly reduces the sample set of sequence variations that are analyzed to determine the actual sequence variations in the target sequence, relative to the previous approach of simulating the fragmentation pattern of every possible sequence that is a variation of a reference sequence, and comparing the simulated patterns with the actual fragmentation pattern of the target nucleic acid sequence.

Two functions d+, d− are defined as:

$d_+(c) := \sum_{b \text{ in } \{A,C,G,T\}} c(b)$ for those b with $c(b)>0$
$d_-(c) := \sum_{b \text{ in } \{A,C,G,T\}} c(b)$ for those b with $c(b)<0$ and a function d(c) is defined as $d(c) := \max\{d_+(c), d_-(c)\}$ and $d(c,c') := d(c-c')$. This is a metric function that provides a lower bound for the number of insertions, deletions, substitutions and other sequence variations that are needed to mutate one fragment, e.g., a reference fragment into another, e.g., a target fragment. If f,f' are fragments and c,c' are the corresponding compomers, then we need at least d(c,c') sequence variations to transform f into f'.

A substring (fragment) of the string s (full length sequence) is denoted s[i,j], where i,j are the start and end positions of the substring satisfying 1≤i≤j≤length of s.

A compomer boundary or boundary is a subset of the set {L,R}. Possible values for b are { } (the empty set), {L}, {R}, {L,R}. For a boundary b, #b denotes the number of elements in b, that is, 0, 1, or 2. A bounded compomer (c,b) contains a compomer c and a boundary b. Bounded compomers refers to the set of all compomers c that correspond to the set of subsequences of a reference sequence, with a boundary that indicates whether or not cleavage sites are present at the two ends of each subsequence. The set of bounded compomers can be compared against possible compomer witnesses to construct all possible sequence variations of a target sequence relative to a reference sequence. The distance between a compomer c' and a bounded compomer (c,b) is defined as:

$$D(c',c,b) := d(c',c) + \#b$$

The function D(c',c,b) measures the minimum number of sequence variations relative to a reference sequence that is needed to generate the compomer witness c'.

Given a specific cleavage reaction of a base, amino acid, or other feature X recognized by the cleavage reagent in a string s, then the boundary b[i,j] of the substring s[i,j] or the corresponding compomer c[i,j] refers to a set of markers indicating whether cleavage of string s does not take place immediately outside the substring s[i,j]. Possible markers are L, indicating whether "s is not cleaved directly before i", and R, indicating whether "s is not cleaved directly after j". Thus, b[i,j] is a subset of the set {L,R} that contains L if and only if X is present at position i−1 of the string s, and contains R if and only if X is present at position j+1 of the string s. #b denotes the number of elements in the set b, which can be 0, 1, or 2, depending on whether the substring s[i,j] is specifically cleaved at both immediately flanking positions (ie., at positions i−1 and j+1), at one immediately flanking position (ie., at either position i−1 or j+1) or at no immediately flanking position (ie., at neither position i−1 nor j+1). b[i,j] is a subset of the set {L,R} and denotes the boundary of s[i,j] as defined by the following:

b[i,j]={L,R} if s is neither cleaved directly before i nor after j
b[i,j]:={R} if s is cleaved directly before i, but not after j
b[i,j]:={L} if s is cleaved directly after j, but not before i
b[i,j]={ } if s is cleaved directly before i and after j b[i,j] denotes the number of elements of the set b[i,].

The set of all bounded compomers of s is defined as: $C:=\{(c[i,j],b[i,j]): 1 \leq i \leq j \leq$ length of $s\}$, where the compomer corresponding to the substring s[i,j] of s is denoted c[i,j].

If there is a sequence variation of a target sequence containing at most k mutations, polymorphisms, or other sequence variations, including, but not limited to, sequence variations between organisms, insertions, deletions and substitutions (usually, for a nucleic acid, k represents the number of single base variations in a sequence variation), and if c' is a compomer witness of this sequence variation, then there exists a bounded compomer (c,b) in C such that $D(c',c,b) \leq k$. In other words, of every sequence variation of a target sequence containing at most k mutations, polymorphisms, or other sequence variations, including, but not limited to, sequence variations between organisms, insertions, deletions and substitutions (usually, for a nucleic acid, k represents the number of single base variations in a sequence variation) that leads to a different fragment corresponding to a signal that is different in the target sequence relative to the reference sequence and that corresponds to a compomer witness c', there is a bounded compomer (c,b) in C with the property $D(c',c,b) \leq k$. Thus, the number of fragments under consideration can be reduced to just those which contain at most k cleavage points:

$C_k:=\{(c[i,j], b[i,j]): 1 \leq i \leq j \leq$ length of s, and $ord[i,j]+\#b[i,j] \leq k\}$, where ord[i,j] is the number of times the fragment s[i,j] will be cleaved.

Algorithm 1: FindSequenceVariationCandidates

INPUT: Reference sequence s (or more than one reference sequence), description of cleavage reaction, whether modified nucleotides or amino acids are incorporated into all or part of the sequence, list of peaks corresponding to different fragments (either missing signals or additional signals or qualitative differences in the target sequence relative to the reference sequence(s)), maximal sequence variation order k.

OUTPUT: List of sequence variations that contain at most k insertions, deletions, and substitutions, and that have a different peak as a witness.

Given the reference sequence s and the specific cleavage reaction, compute all bounded compomers (c[i,j],b[i,j]) in $C_k$, and store them together with the indices i,j. This is usually independent of the samples containing target sequences being analyzed, and is usually done once.

For every different peak, find all compomers with mass close to the peak mass by a sufficiently small mass difference, and store them as compomer witnesses.

For every compomer witness c', find all bounded compomers (c,b) in $C_k$ such that $D(c',c,b) \leq k$.

For every such bounded compomer (c,b) with indices i,j compute all sequence variations of s to a new reference sequence s' using at most k insertions, deletions, and substitutions such that:

if L in b, then we insert/substitute to a cleaved base or amino acid directly before position i;

if R in b, then we insert/substitute to a cleaved base or amino acid directly after position j;

Use at most k−#b insertions, deletions, and insertions that transform the fragment f=s[i,j] with corresponding compomer c into some fragment f' of s' with corresponding compomer c'.

Output every such sequence variation.

Figure 2:
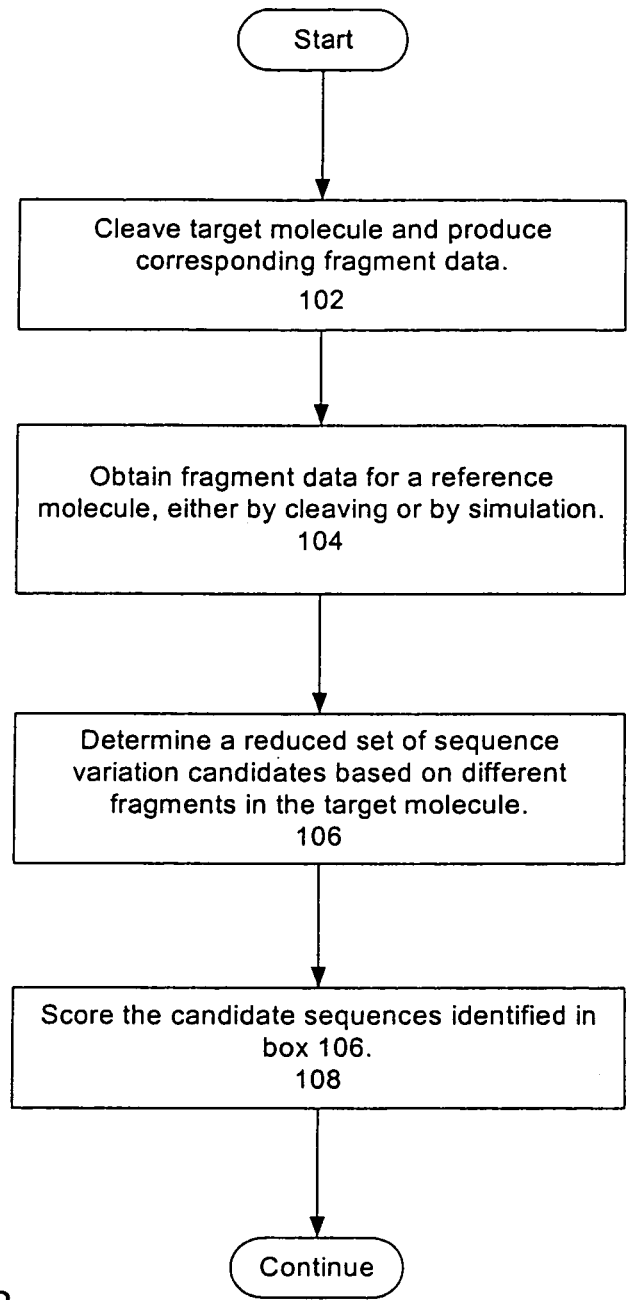
FIG. 2 is a flow diagram that illustrates operations performed with a computer system that is engaged in data analysis to determine those sequence variation candidates that satisfy the criteria described herein.

FIG. 2 is a flow diagram that illustrates operations performed with a computer system that is engaged in data analysis to determine those sequence variation candidates that satisfy the criteria described above. In the first operation, indicated by box 102, the target molecule is cleaved into fragments using one or more cleavage reagents, using techniques that are well-known to those of skill in the art and described herein. In the next operation, represented by box 104, the reference molecule is actually or virtually (by simulation) cleaved into fragments using the same one or more cleavage reagents. From the fragments produced by the cleavage reactions, data, such as mass spectra for the target and reference sequences, are produced. The produced data can be used to extract a list of peaks of the sequence data corresponding to fragments that represent differences between the target sequence and the reference sequence.

The next operation is to determine a reduced set of sequence variation candidates based on the identified different fragments. This operation is depicted by box 106. The sequence variation candidates are then scored (box 108), and the sequence variation candidates corresponding to the actual sequence variations in the target sequence are identified based on the value of the score. Usually, in a set of samples of target sequences, the highest score represents the most likely sequence variation in the target molecule, but other rules for selection can also be used; such as detecting a positive score, when a single target sequence is present.

In an exemplary embodiment described herein, the data produced from cleavage reactions comprises the output of conventional laboratory equipment for the analysis of molecular information. Such output is readily available in a variety of digital data formats, such as plain text or according to word processing formats or according to proprietary computer data representations.

Figure 3:
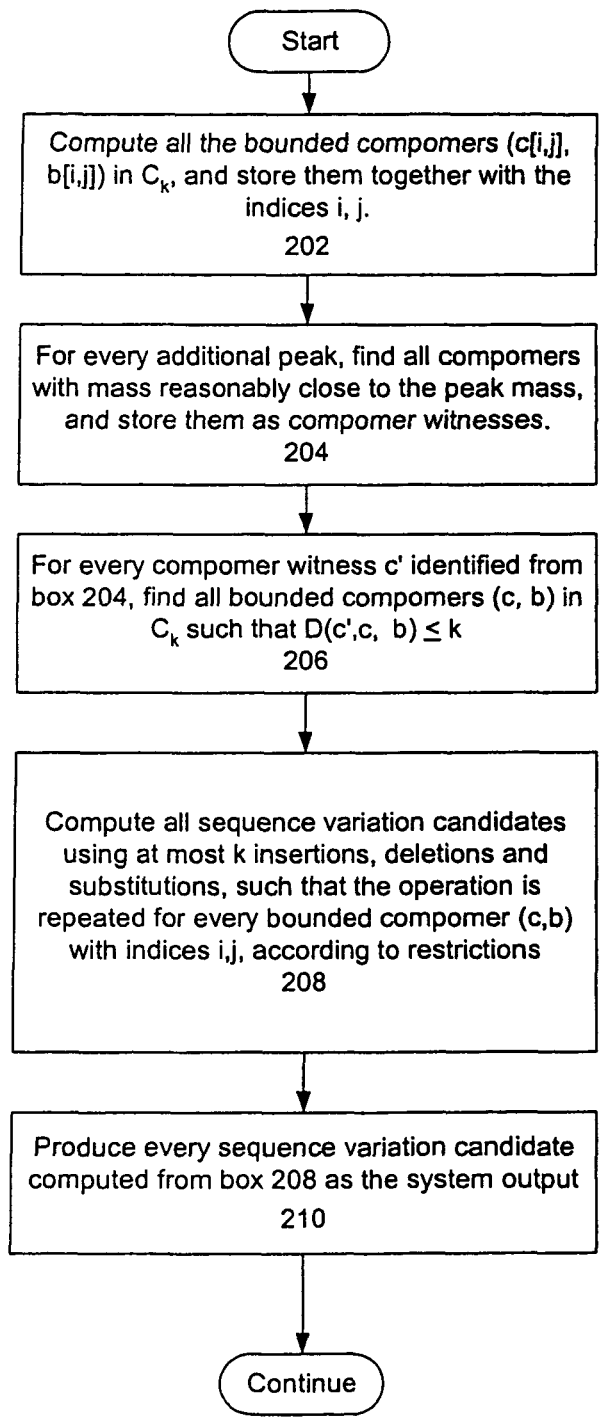
FIG. 3 is a flow diagram that illustrates the operations executed by a computer system to determine the reduced set of sequence variation candidates.

As described above, the process of determining a reduced set of sequence variation candidates based on the identified different fragments can be performed with a programmed computer. FIG. 3 is a flow diagram that illustrates the operations executed by a computer system to determine the reduced set of sequence variation candidates.

In the first operation, represented by box 202, the reaction data described above is processed to compute all bounded compomers (c[i,j],b[i,j]) in $C_k$, and stored together with the indices i,j, in accordance with the reference sequence s and the specific cleavage reaction data described above. The next operation, indicated by box 204, is to find, for every different peak, all compomers with mass that differs from the peak mass by a sufficiently small mass difference that is reasonably close to the peak mass. The value of the sufficiently small mass difference is determined by parameters that include, but are not limited to, the peak separation between fragments whose masses differ by a single nucleotide in type or length, and the absolute resolution of the mass spectrometer. These compomers are stored as compomer witnesses. After the compomer witnesses are identified, the next operation is to find, for every compomer witness c' identified from box 204, all bounded compomers (c,b) in $C_k$ such that $D(c',c,b) \leq k$. The bounded compomer operation is represented by box 206. Box 208 represents the operation that involves the computation of all sequence variation candidates of s to a new reference sequence s' using at most k insertions, deletions, and substitutions such that:

if L in b, then we insert/substitute to a cleaved base or amino acid directly before position i;

if R in b, then we insert/substitute to a cleaved base or amino acid directly after position j;

Use at most k-#b insertions, deletions, and insertions that transform the fragment f=s[i,j] with corresponding compomer c into some fragment f' of s' with corresponding compomer c'.

The last operation, indicated by box 210, is to produce every such sequence variation candidate computed from box 208 as the system output.

Here, d(c,c') is the function as defined herein that determines the minimum number of sequence variations, polymorphisms or mutations (insertions, deletions, substitutions) that are needed to convert c to c', where c is a compomer of a fragment of the reference molecule and c' is the compomer of the target molecule resulting from mutation of the c fragment.

A substring (fragment) of the string s (full length sequence) is denoted s[i,j]i, where i,j are the start and end positions of the substring.

Given a specific cleavage reaction of a base, amino acid, or other feature X recognized by the cleavage reagent in a string s, then the boundary b[i,j] of the substring s[i,j] or the corresponding compomer c[i,j] refers to a set of markers indicating whether cleavage of string s does not take place immediately outside the substring s[i,j]. Possible markers are L, indicating whether "s is not cleaved directly before i", and R, indicating whether "s is not cleaved directly after j". Thus, b[i,j] is a subset of the set $\{L,R\}$ that contains L if and only if X is present at position i−1 of the string s, and contains R if and only if X is present at position j+1 of the string s. #b denotes the number of elements in the set b, which can be 0, 1, or 2, depending on whether the substring s[i,j] is specifically cleaved at both immediately flanking positions (i.e., at positions i−1 and j+1), at one immediately flanking position (i.e., at either position i−1 or j+1) or at no immediately flanking position (i.e., at neither position i−1 nor j+1). b[i,j] is a subset of the set $\{L,R\}$ and denotes the boundary of s[i,j] as defined by the following:

b[i,j]:=$\{L,R\}$ if s is neither cleaved directly before i nor after j b[i,j]:=$\{R\}$ if s is cleaved directly before i, but not after j b[i,j]:=$\{L\}$ if s is cleaved directly after j, but not before i b[i,j]:=$\{\}$ if s is cleaved directly before i and after j b[i,j] denotes the number of elements of the set b[i,j].

ord[i,j] refers to the number of times s[i,j] will be cleaved in a particular cleavage reaction; i.e., the number of cut strings present in s[i,j].

D(c',c,b):=d(c,c')+#b refers to the distance between compomer c' and bounded compomer (c,b)'; i.e., the total minimum number of changes needed to create the fragment with compomer c' from the fragment with compomer c, including sequence variations of the boundaries of substring s[i,j] into cut strings, if necessary.

C=$\{$(c[i,j],b[i,j]): $1 \leq i \leq j \leq$ length of s$\}$ refers to the set of all bounded compomers within the string s; i.e., for all possible substrings s[i,j], find the bounded compomer (c[i,j],b[i,j]) and these will belong to the set C.

$C_k$=$\{$(c[i,j], b[i,j]): $1 \leq i \leq j \leq$ length of s, and ord[i,j]+#b[i,j]$\leq$k$\}$ is the same as C above, except that compomers for substrings containing more than k number of sequence variations of the cut string will be excluded from the set, i.e., $C_k$ is a subset of C. It can be shown that if there is a sequence variation containing at most k insertions, deletions, and substitutions, and if c' is a compomer corresponding to a peak witness of this sequence variation, then there exists (c,b) in $C_k$ such that D(c',c,b)$\leq$k. The algorithm is based on this reduced set of possible sequence variations corresponding to compomer witnesses.

Every sequence variation constructed in this fashion leads to the creation of at least one different peak out of the list of input different peaks. Further, every sequence variation that contains at most k insertions, deletions, and insertions that was not constructed by the algorithm is either the superset of the union of one or more sequence variations that were constructed, or does not lead to the creation of any different peaks out of the list of different peaks that served as input for the algorithm.

Algorithm 1 can be repeated for more than one specific cleavage reagent generating more than one target fragmentation pattern relative to a reference fragmentation pattern, and more than one list of compomer witnesses. In one embodiment, the final output contains the set of sequence variation candidates that is the union of the sets of sequence variation candidates for each cleavage reaction.

Algorithm 2

A second algorithm is used to generate a simulated spectrum for each computed output sequence variation candidate. The simulated spectrum for each sequence variation candidate is scored, using a third (scoring) algorithm, described below, against the actual target spectrum, applying the reference spectrum for the reference sequence. The value of the scores (the higher the score, the better the match, with the highest score usually being the sequence variation that is most likely to be present) can then be used to determine the sequence variation candidate that is actually present in the target nucleic acid sequence.

Provided below is an exemplary algorithm where the sequence variations to be detected are SNPs. Algorithms for detecting other types of sequence variations, including homozygous or heterozygous allelic variations, can be implemented in a similar fashion.

a) For each cleavage reaction, a simulated spectrum is generated for a given sequence variation candidate from Algorithm 1.

b) The simulated spectrum is scored against the actual target spectrum.

c) The scores from all cleavage reactions, typically complementary cleavage reactions, for the given target sequence are added. The use of more than one specific cleavage reaction improves the accuracy with which a particular sequence variation can be identified.

d) After all scores have been calculated for all sequence variations, sequence variations are sorted according to their score.

Algorithm 2: FindSNPs

INPUT: Reference sequence s, one or more cleavage reaction, for every cleavage reaction a simulated or actual reference fragmentation spectrum, for every cleavage reaction a list of peaks found in the corresponding sample spectrum, maximal sequence variation order k.

OUTPUT: List of all SNP candidates corresponding to sequence variations containing at most k insertions, deletions, and substitutions, and that have a different peak as a witness; and for every such SNP candidate, a score.

For every cleavage reaction, extract the list of different peaks by comparing the sample spectrum with the simulated reference spectrum.

For every cleavage reaction, use FINDSEQUENCEVARIATIONCAN-
DIDATES (Algorithm 1) with input s, the current cleavage
reaction, the corresponding list of different peaks, and k.
Combine the lists of sequence variation candidates returned
by FINDSEQUENCEVARIATIONCANDIDATES into a single list,
removing duplicates.
For every sequence variation candidate:
Apply the sequence variation candidate, resulting in a
sequence s'.
For every cleavage reaction, simulate the reference spectrum
of s' under the given cleavage reaction.
Use SCORESNP (Algorithm 3) with the peak lists correspond-
ing to the spectra of s,s' as well as the peak list for the
measured sample spectrum as input, to calculate scores
(heterozygous and homozygous) of this sequence variation
(or SNP) candidate for the cleavage reaction.
Add up the scores of all cleavage reactions, keeping separate
scores for heterozygous and homozygous variations.
Store a SNP candidate containing the sequence variation
candidate plus its scores; the overall score of the SNP
candidate is the maximum of its heterozygous and
homozygous scores.
Sort the SNP candidates with respect to their scores.
Output the SNP candidates together with their scores.
An exemplary implementation of a scoring algorithm,
SCORESNP, is as follows:

Algorithm 3: SCORESNP

INPUT: Peak lists corresponding to reference sequence s
(denoted L), modified reference sequence s' (denoted L'),
and sample spectrum (denoted $L_s$).
OUTPUT: Heterozygous score, homozygous score.
Set both scores to 0.
Compute a list of intensity changes (denoted $L_A$) that
includes those peaks in the lists corresponding to s,s' that
show differences:
If a peak is present in L but not in L', add this peak to $L_A$ and
mark it as wild-type.
If a peak is present in L' but not in L, add this peak to $L_A$ and
mark it as mutant-type.
If a peak has different expected intensities in L and L', add
this peak to $L_A$, together with the expected intensity
change from L to L'.
For every peak in $L_A$ marked as mutant-type that also is
found in $L_s$, add +1 to both scores.
For every peak in $L_A$ marked as mutant-type that is not
found in $L_s$, add −1 to both scores.
For every peak in $L_A$ marked as wild-type that is not found
in $L_s$, add +1 to the homozygous score.
For every peak in $L_A$ marked as wild-type that also is found
in $L_s$, add −1 to the homozygous score.
Output both scores.
Other implementations of the scoring function are appar-
ent. For example, one implementation employs peaks that are
not differentiated as either mutant or wild-type. Another
implementation can, in addition or as a separate feature, con-
sider intensities in L, $L_A$, and $L_s$. Other exemplary parameters
include using peaks designated as "wild-type" to modify the
heterozygous score, or incorporating a weighting function
that is based on the confidence level in the actual (measured)
target sequence fragmentation spectrum. Another implemen-
tation can use a logarithmic likelihood approach to calculate
the scores.
In one embodiment, instead of using the scores of potential
SNPs output by Algorithm 2 directly, scores from more than
one target sequence expected to contain or actually contain-
ing the same SNP can be joined. When more than one target
sequence is analyzed simultaneously against the same refer-
ence sequence, instead of reporting the SNP score for each
target sequence independently, the scores of all identical
scored sequence variations for the different target sequences
can be joined to calculate a joined score for the SNP. The
joined score can be calculated by applying a function to the
set of scores, which function can include, but is not limited to,
the maximum of scores, the sum of scores, or a combination
thereof.

After all SNP or other sequence variation candidates with
their scores have been calculated, a threshold score can be
determined to report only those SNPs or sequence variations
that have a score that is equal to or higher than the threshold
score (and, therefore, a reasonable chance of being real, i.e.,
of corresponding to the actual sequence variation in the target
sequence). Generally, the sequence variation with the highest
score corresponds to an actual sequence variation in the target
sequence. Sequence variations that are accepted as being real
can then be used to modify the initial reference peak list L.
The modified peak list can then be used to re-evaluate (score)
all other potential sequence variations or SNPs using the
SCORESNP algorithm, or even search for new witnesses in
the case of homozygous SNPs. This leads to an iterative
process of SNP or other sequence variation detection. For
example, in the iterative process of detecting more than one
sequence variation in a target sequence, the sequence varia-
tion with the highest score is accepted as an actual sequence
variation, and the signal or peak corresponding to this
sequence variation is added to the reference fragment spec-
trum to generate an updated reference fragment spectrum. All
remaining sequence variation candidates are then scored
against this updated reference fragment spectrum to output
the sequence variation candidate with the next highest score.
This second sequence variation candidate can also represent a
second actual sequence variation in the target sequence.
Therefore, the peak corresponding to the second sequence
variation can be added to the reference fragment spectrum to
generate a second updated reference spectrum against which
a third sequence variation can be detected according to its
score. This process of iteration can be repeated until no more
sequence variation candidates representing actual sequence
variations in the target sequence are identified. The presented
approach can be applied to any type and number of cleavage
reactions that are complete, including 2-, 1½-, or 1¼-base
cutters. In another embodiment, this approach can be applied
to partial cleavage experiments.

This approach is not limited to SNP and mutation detection
but can be applied to detect any type of sequence variation,
including polymorphisms, mutations and sequencing errors.

Since the presented algorithms are capable of dealing with
homogeneous samples, it will be apparent to one of skill in the
art that their use can be extended to the analysis of sample
mixtures. Such "sample mixtures" usually contain the
sequence variation or mutation or polymorphism containing
target nucleic acid at very low frequency, with a high excess
of wildtype sequence. For example, in tumors, the tumor-
causing mutation is usually present in less than 5-10% of the
nucleic acid present in the tumor sample, which is a hetero-
geneous mixture of more than one tissue type or cell type.
Similarly, in a population of individuals, most polymor-
phisms with functional consequences that are determinative
of, e.g., a disease state or predisposition to disease, occur at
low allele frequencies of less than 5%. The methods provided
herein can detect high frequency sequence variations or can
be adapted to detect low frequency mutations, sequence variations, alleles or polymorphisms that are present in the range of less than about 5-10%.

F. APPLICATIONS

1. Detection of Polymorphisms

An object herein is to provide improved methods for identifying the genomic basis of disease and markers thereof. The sequence variation candidates identified by the methods provided herein include sequences containing sequence variations that are polymorphisms. Polymorphisms include naturally occurring, somatic sequence variations and those arising from mutation. Polymorphisms include but are not limited to: sequence microvariants where one or more nucleotides in a localized region vary from individual to individual, insertions and deletions which can vary in size from one nucleotide to millions of bases, and microsatellite or nucleotide repeats which vary by numbers of repeats. Nucleotide repeats include homogeneous repeats such as dinucleotide, trinucleotide, tetranucleotide or larger repeats, where the same sequence is repeated multiple times, and also heteronucleotide repeats where sequence motifs are found to repeat. For a given locus the number of nucleotide repeats can vary depending on the individual.

A polymorphic marker or site is the locus at which divergence occurs. Such site can be as small as one base pair (an SNP). Polymorphic markers include, but are not limited to, restriction fragment length polymorphisms (RFLPs), variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Furthermore, numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transplantation. Accordingly, it is highly desirable to develop rapid, sensitive, and accurate methods for determining the identity of allelic variants of polymorphic regions of genes or genetic lesions. A method or a kit as provided herein can be used to genotype a subject by determining the identity of one or more allelic variants of one or more polymorphic regions in one or more genes or chromosomes of the subject. Genotyping a subject using a method as provided herein can be used for forensic or identity testing purposes and the polymorphic regions can be present in mitochondrial genes or can be short tandem repeats.

Single nucleotide polymorphisms (SNPs) are generally biallelic systems, that is, there are two alleles that an individual can have for any particular marker. This means that the information content per SNP marker is relatively low when compared to microsatellite markers, which can have upwards of 10 alleles. SNPs also tend to be very population-specific; a marker that is polymorphic in one population can not be very polymorphic in another. SNPs, found approximately every kilobase (see Wang et al., *Science* 280:1077-1082 (1998)), offer the potential for generating very high density genetic maps, which permit development of haplotyping systems for genes and/or regions of interest. Also, because of the nature of SNPS, they can be the polymorphisms associated with the disease phenotypes under study. The low mutation rate of SNPs also makes them excellent markers for studying complex genetic traits.

Much of the focus of genomics has been on the identification of SNPs, which are important for a variety of reasons. They allow indirect testing (association of haplotypes) and direct testing (functional variants). They are the most abundant and stable genetic markers. Common diseases are best explained by common genetic alterations, and the natural variation in the human population aids in understanding disease, therapy and environmental interactions.

2. Haplotyping

As set forth herein, the methods provided herein are particularly useful for detecting haplotypes. In any diploid cell, there are two haplotypes at any gene or other chromosomal segment that contain at least one distinguishing variance. In many well-studied genetic systems, haplotypes are more powerfully correlated with phenotypes than single nucleotide variations. Thus, the determination of haplotypes is valuable for understanding the genetic basis of a variety of phenotypes including disease predisposition or susceptibility, response to therapeutic interventions, and other phenotypes of interest in medicine, animal husbandry, and agriculture.

Haplotyping procedures as provided herein permit the selection of a portion of sequence from one of an individual's two homologous chromosomes and to genotype linked SNPs on that portion of sequence. The direct resolution of haplotypes can yield increased information content, improving the diagnosis of any linked disease genes or identifying linkages associated with those diseases.

3. HLA-Typing

The allele-specific haplotyping methods provided herein also are useful for HLA-typing. HLAs (human leukocyte antigens) are a complex of cell-surface proteins involved in the recognition of target cells by cytotoxic T lymphocytes as part of the immune response. The HLA proteins exhibit a high degree of polymorphism. Detection of these polymorphisms (HLA-typing) and matching of similar HLA-types is used prior to organ transplantation to assess compatibility between donors and recipients. Additionally, HLA-typing is used in forensics and paternity testing to assess relatedness of individuals. HLA types also are correlated with genetic disposition to diseases, including but not limited to, diabetes, coeliac disease, and rheumatoid arthritis. The polymorphisms exhibited by HLA genes are primarily single nucleotide polymorphisms (SNPs).

In a particular embodiment, the methods herein are used for HLA-typing. Often individuals are heterozygous at HLA loci. Because each HLA haplotype is comprised of a collection of SNPs at each HLA locus, genotyping in heterozygous individuals can be complex and prone to error. In one embodiment of the methods described herein, an allele-specific template is generated from a heterozygous starting material (e.g., a blood sample from a heterozygous individual) by selecting for amplification of one allele, followed by further genotype determination at linked loci in a high-throughput manner. One of the two PCR primers is designed to anneal at a selected allele at a discriminating SNP for an HLA gene (allele-specific primer). The last base at the 3'end of this primer is complementary to the desired allele. The competitor oligonucleotide (NEER oligonucleotide) is designed to act as an extension inhibitor such that other alleles are not extended in the PCR reaction. The exonuclease resistant feature of the NEER oligonucleotide reduces leakage and thus ambiguities from these other alleles. The PCR products are analyzed by hMC, hME or other methods known in the art for analyzing and determining genotypes.

As an example of using the methods provided herein for HLA-typing, the initial NEER-ASPCR amplification reaction can be designed to amplify the DRB region of a gene, for example, within the DRB1 locus (see, e.g., U.S. Pat. No. 5,578,443). In this exemplary embodiment, the first PCR primer is designed to anneal to the HLA-DRB1 gene such that the last base of the 3' end of the primer anneals to the desired allele at a chosen polymorphic nucleotide, and the NEER competitor is designed such that if another nucleotide is present at this position, that allele is not extended. For example, the NEER oligonucleotide has the same sequence as the first primer except that the 3' end of the primer is non-extendable and exonuclease resistant. A second PCR primer is designed to anneal within the DRB region downstream from the first primer, and contains a promoter sequence therein (e.g., a T7 promoter sequence). The initial PCR reaction generates PCR product from only one desired specified allele. This product is then further genotyped, using for example hME or hMC (described herein), to characterize the sequence of this allele and determine other linked polymorphisms at the DRB1 locus, thus determining the HLA-haplotype at this locus. In a similar manner, primers can be designed to amplify other alleles at the DRB1 locus, or alleles at other HLA loci. High throughput formats for example, with the NEER AS-PCR step and the subsequent genotyping with hME or hMC, allow haplotypes to be determined rapidly for many loci such as the many loci comprising the HLA region.

E. SYSTEM AND SOFTWARE METHOD

Also provided are systems that automate the methods for determining sequence variations in a target nucleic acid or protein or the detection methods provided herein using a computer programmed for identifying the sequence variations based upon the methods provided herein. The methods herein can be implemented, for example, by use of the following computer systems and using the following calculations, systems and methods.

An exemplary automated testing system contains a nucleic acid workstation that includes an analytical instrument, such as a gel electrophoresis apparatus or a mass spectrometer or other instrument for determining the mass of a nucleic acid molecule in a sample, and a computer for fragmentation data analysis capable of communicating with the analytical instrument (see, e.g., copending U.S. application Ser. Nos. 09/285, 481, 09/663,968 and 09/836,629; see, also International PCT application No. WO 00/60361 for exemplary automated systems). In an exemplary embodiment, the computer is a desktop computer system, such as a computer that operates under control of the "Microsoft Windows" operation system of Microsoft Corporation or the "Macintosh" operating system of Apple Computer, Inc., that communicates with the instrument using a known communication standard such as a parallel or serial interface.

For example, systems for analysis of nucleic acid samples are provided. The systems include a processing station that performs a base-specific or other specific cleavage reaction as described herein; a robotic system that transports the resulting cleavage fragments from the processing station to a mass measuring station, where the masses of the products of the reaction are determined; and a data analysis system, such as a computer programmed to identify sequence variations in the target nucleic acid sequence using the fragmentation data, that processes the data from the mass measuring station to identify a nucleotide or plurality thereof in a sample or plurality thereof. The system can also include a control system that determines when processing at each station is complete and, in response, moves the sample to the next test station, and continuously processes samples one after another until the control system receives a stop instruction.

Figure 4:
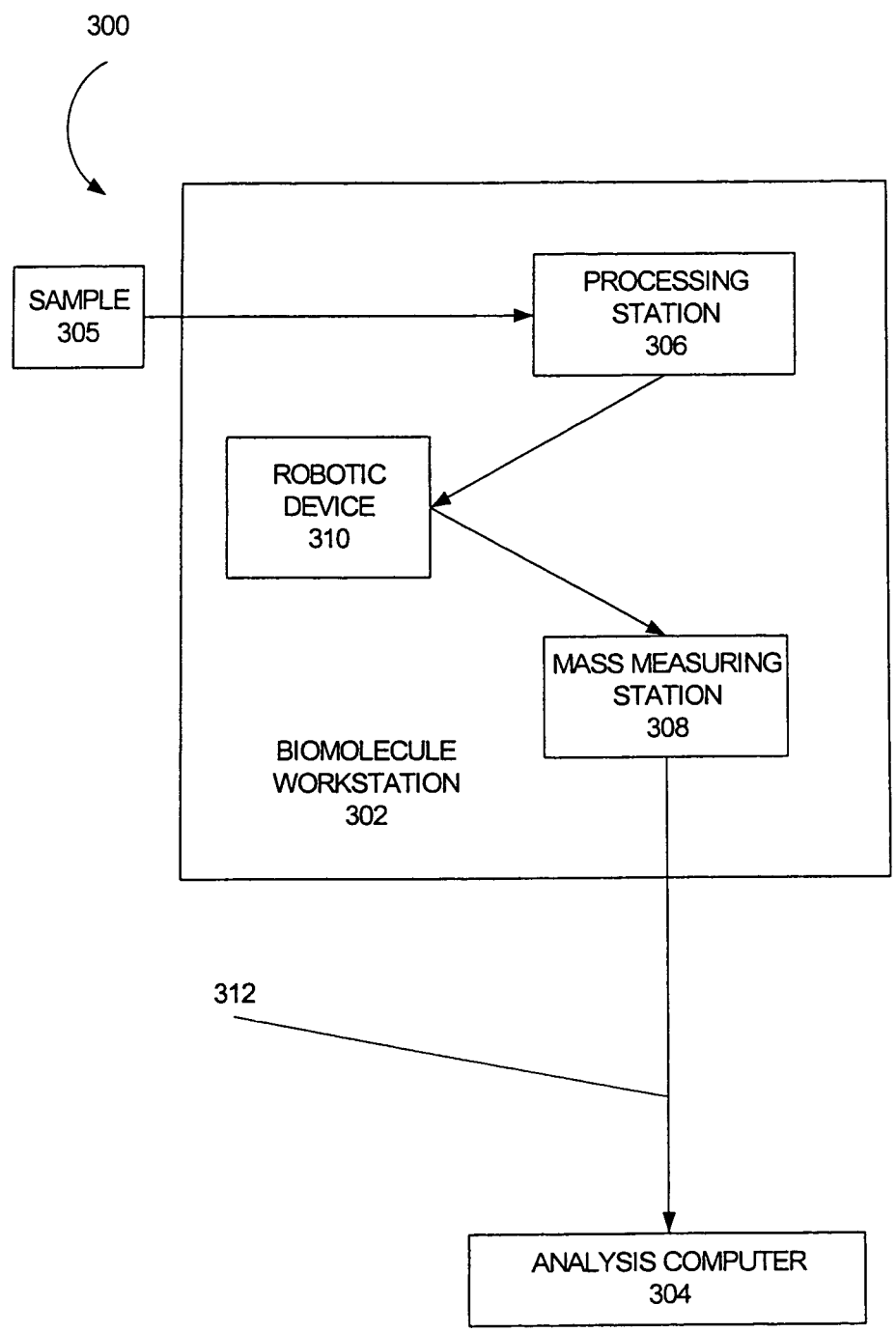
FIG. 4 is a block diagram of a system that performs sample processing and performs the operations illustrated in FIG. 2 and FIG. 3.

FIG. 4 is a block diagram of a system that performs sample processing and performs the operations illustrated in FIG. 2 and FIG. 53. The system 300 includes a biomolecule workstation 302 and an analysis computer 304. At the biomolecule station, one or more molecular samples 305 are received and prepared for analysis at a processing station 306, where the above-described cleavage reactions can take place. The samples are then moved to a mass measuring station 308, such as a mass spectrometer, where further sample processing takes place. The samples are typically moved from the sample processing station 306 to the mass measuring station 308 by a computer-controlled robotic device 310.

The robotic device can include subsystems that ensure movement between processing station 306 and the mass measuring station 308 that will preserve the integrity of the samples 305 and will ensure valid test results. The subsystems can include, for example, a mechanical lifting device or arm that can pick up a sample from the sample processing station 306, move to the mass measuring station 308, and then deposit the processed sample for a mass measurement operation. The robotic device 310 can then remove the measured sample and take appropriate action to move the next processed sample from the processing station 306.

The mass measuring station 308 produces data that identifies and quantifies the molecular components of the sample 305 being measured. Those skilled in the art will be familiar with molecular measurement systems, such as mass spectrometers, that can be used to produce the measurement data. The data is provided from the mass measuring station 308 to the analysis computer 304, either by manual entry of measurement results into the analysis computer or by communication between the mass measuring station and the analysis computer. For example, the mass measuring station 308 and the analysis computer 304 can be interconnected over a network 312 such that the data produced by the mass measuring station can be obtained by the analysis computer. The network 312 can comprise a local area network (LAN), or a wireless communication channel, or any other communications channel that is suitable for computer-to-computer data exchange.

The measurement processing function of the analysis computer 304 and the control function of the biomolecule workstation 302 can be incorporated into a single computer device, if desired. In that configuration, for example, a single general purpose computer can be used to control the robotic device 310 and to perform the data processing of the data analysis computer 304. Similarly, the processing operations of the mass measuring station and the sample processing operations of the sample processing station 306 can be performed under the control of a single computer.

Thus, the processing and analysis functions of the stations and computers 302, 304, 306, 308, 310 can be performed by a variety of computing devices, if the computing devices have a suitable interface to any appropriate subsystems (such as a mechanical arm of the robotic device 310) and have suitable processing power to control the systems and perform the data processing.

The data analysis computer 304 can be part of the analytical instrument or another system component or it can be at a remote location. The computer system can communicate with the instrument, for example, through a wide area network or local area communication network or other suitable communication network. The system with the computer is programmed to automatically carry out steps of the methods herein and the requisite calculations. For embodiments that use predicted fragmentation patterns (of a reference or target sequence) based on the cleavage reagent(s) and modified bases or amino acids employed, a user enters the masses of the predicted fragments. These data can be directly entered by the user from a keyboard or from other computers or computer systems linked by network connection, or on removable storage medium such as a data CD, minidisk (MD), DVD, floppy disk or other suitable storage medium. Next, the user initiates execution software that operates the system in which the fragment differences between the target nucleic acid sequence and the reference nucleic acid sequence, are identified. The sequence variation software performs the steps of Algorithm 1 and, in some embodiments, Algorithms 2 or 3 as described herein.

Figure 5:
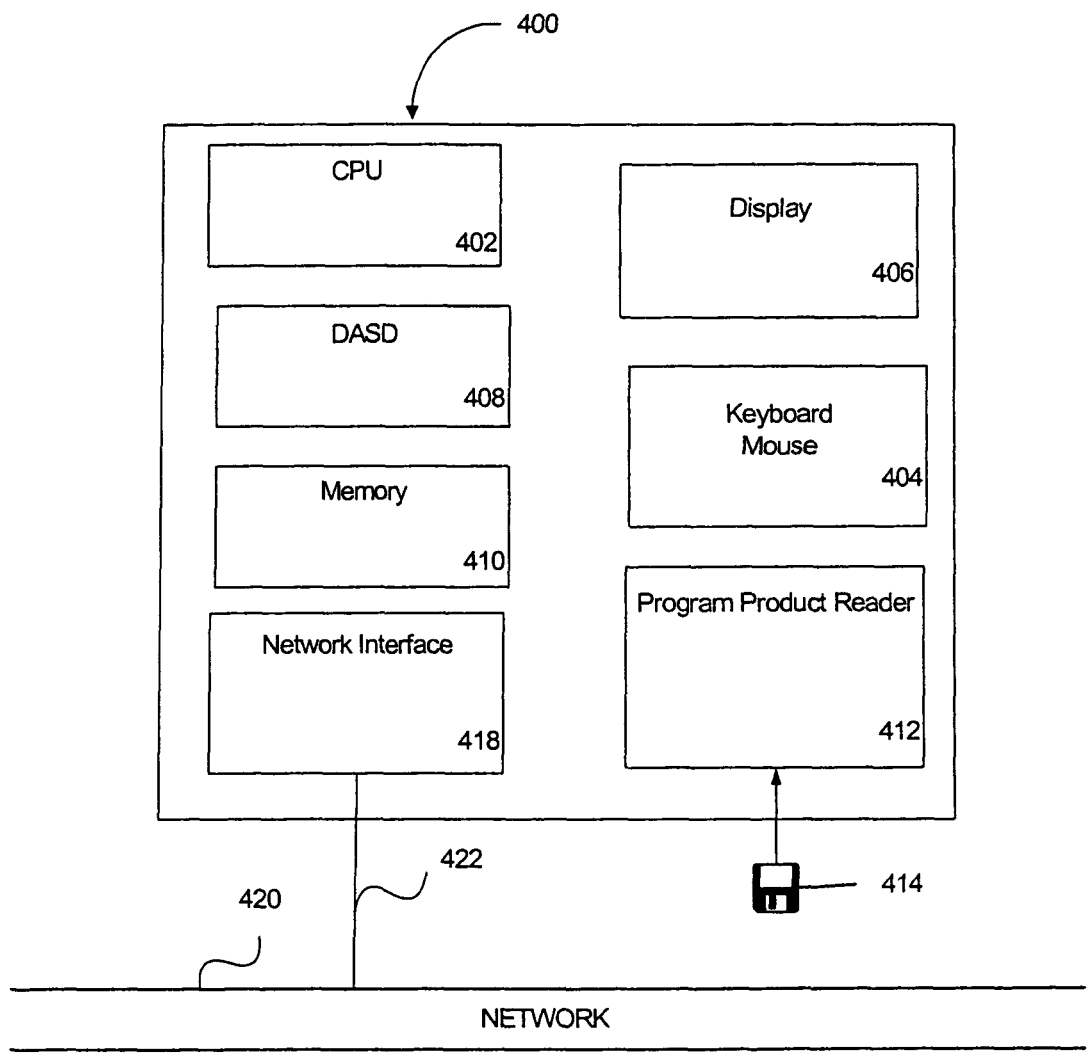
FIG. 5 is a block diagram of a computer in the system 300 of FIG. 4, illustrating the hardware components included in a computer that can provide the functionality of the stations and computers 302, 304, 306, 308.

FIG. 5 is a block diagram of a computer in the system 300 of FIG. 4, illustrating the hardware components included in a computer that can provide the functionality of the stations and computers 302, 304, 306, 308. Those skilled in the art will appreciate that the stations and computers illustrated in FIG. 4 can all have a similar computer construction, or can have alternative constructions consistent with the capabilities and respective functions described herein. The FIG. 5 construction is especially suited for the data analysis computer 304 illustrated in FIG. 4.

FIG. 5 shows an exemplary computer 400 such as might comprise a computer that controls the operation of any of the stations and analysis computers 302, 304, 306, 308. Each computer 400 operates under control of a central processor unit (CPU) 402, such as a "Pentium" microprocessor and associated integrated circuit chips, available from Intel Corporation of Santa Clara, Calif., USA. A computer user can input commands and data from a keyboard and mouse 404, and can view inputs and computer output at a display 406. The display is typically a video monitor or flat panel display. The computer 400 also includes a direct access storage device (DASD) 408, such as a hard disk drive. The computer includes a memory 410 that typically comprises volatile semiconductor random access memory (RAM). Each computer can include a program product reader 412 that accepts a program product storage device 414, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc.

Each computer 400 can communicate with the other FIG. 4 systems over a computer network 420 (such as, for example, the local network 312 or the Internet or an intranet) through a network interface 418 that permits communication over a connection 422 between the network 420 and the computer 400. The network interface 418 typically comprises, for example, a Network Interface Card (NIC) that permits communication over a variety of networks, along with associated network access subsystems, such as a modem.

The CPU 402 operates under control of programming instructions that are temporarily stored in the memory 410 of the computer 400. When the programming instructions are executed, the computer performs its functions. Thus, the programming instructions implement the functionality of the respective workstation or processor. The programming instructions can be received from the DASD 408, through the program product storage device 414, or through the network connection 422. The program product storage drive 412 can receive a program product storage device 414, read programming instructions recorded thereon, and transfer the programming instructions into the memory 410 for execution by the CPU 402. As noted above, the program product storage device can comprise any one of multiple removable media having recorded computer-readable instructions, including magnetic floppy disks and CD-ROM storage discs. Other suitable program product storage devices can include magnetic tape and semiconductor memory chips. In this way, the processing instructions necessary for operation in accordance with the methods and disclosure herein can be embodied on a program product storage device. Alternatively, the program instructions can be received into the operating memory 410 over the network 420. In the network method, the computer 400 receives data including program instructions into the memory 410 through the network interface 418 after network communication has been established over the network connection 422 by well-known methods that will be understood by those skilled in the art without further explanation. The program instructions are then executed by the CPU 402 thereby comprising a computer process.

It should be understood that all of the stations and computers of the system 300 illustrated in FIG. 4 can have a construction similar to that shown in FIG. 5, so that details described with respect to the FIG. 5 computer 400 will be understood to apply to all computers of the system 300. It should be appreciated that any of the communicating stations and computers can have an alternative construction, so long as they can communicate with the other communicating stations and computers illustrated in FIG. 4 and can support the functionality described herein. For example, if a workstation will not receive program instructions from a program product device, then it is not necessary for that workstation to include that capability, and that workstation will not have the elements depicted in FIG. 5 that are associated with that capability.

The following Examples are included for illustrative purposes only and are not intended to limit the scope of the invention. Although hardware and software available from SEQUENOM are referenced herein, those of skill in the art will recognize that the NEER-ASPCR methods (Section B.1.a.) and the algorithms for analyzing base-specific fragmentation (Section E.) provided herein can be used with other combinations of hardware and software packages known to those of skill in the art for mass spectrometry analysis.

For example, one skilled in the art can perform the methods as provided herein, as demonstrated by the knowledge in the art as exemplified in issued patents and published international applications incorporated by reference herein, and that describe methods, systems and devices that can be adapted for use with the NEER-ASPCR methods (Section B. 1.a.) and/or the base-specific fragmentation algorithms (Section E.) provided herein, such as: U.S. Pat. Nos. 5,807,522, 6,110,426, 6,024,925, 6,133,436, 5,900,481, 6,043,031, 5,605,798, 5,691,141, 5,547,835, 5,872,003, 5,851,765, 5,622,824, 6,074,823, 6,022,688, 6,111,251, 5,777,324, 5,928,906, 6,225,450, 6,146,854, 6,207,370, U.S. application Ser. No. 09/663,968, International PCT application No. WO 99/12040, WO 97/42348, WO 98/20020, WO 98/20019, WO 99/57318, WO 00/56446, WO 00/60361, WO 02/25567 and WO 02/086794. These patents and publications exemplify the knowledge and level of skill of one in the art, and describe a variety of mass spectrometric analytical methods, substrates and matrices used in mass spectrometric analyses, and related methods and apparatus, including pin tools and other dispensing systems. It is intended that the methods, products and systems described in these patents and patent applications as well as other such methods that employ instruments for detection of molecules and computer-directed assays, and are particularly suitable for use in high throughput formats, can be adapted for use with the optimized multiplexing methods of genotyping provided herein. Other intended uses include any methods and assays that have an instrument for data acquisition and that employ data-typing analyses.

Example 1

Haplotyping Using NEER-ASPCR: Allele-Specific PCR with a Non-Extendable Exonuclease Resistant Competitor The following haplotyping protocol describes the use of one embodiment of the allele-specific PCR amplification methods provided herein, referred to herein as Non-Extendable Exonuclease Resistant-Allele Specific PCR (NEER-ASPCR). In these methods, the competitor oligonucleotide improves specificity of the AS-PCR amplification by reducing amplification of the non-desired allele (leakage), which can occur, for example, when the discriminatory end base involves a weak mismatch such as CA or GT. This Example demonstrates the usation of NEER competitors with 3' inverted and dideoxy bases and also the use of mismatches in the penultimate base of the forward ASPCR amplification primer.

The AS-PCR reaction was conducted as follows. A sample of genomic DNA was isolated from 10 mL of buffy coat samples using the PUREGENE kit (Gentra Systems). The genomic DNA sample was purchased from the San Bernardino, Calif. blood bank, and was prepared at a concentration of 2.5 ng/µl in 0.25× TE (Tris-HCl buffered EDTA). A PCR reaction mix was assembled with the final concentration of reagents as shown in Table 1. The final concentration of $MgCl_2$ was 1.5 mM. A range of NEER competitor concentrations was tested to optimize the reaction. The reaction was designed to amplify the IKBA gene locus at an internal SNP previously genotyped as heterozygous genomic DNA sample. The forward primer (allele-specific primer) 5'-GGC-CAGCGTCTGACGTTATGAGC-3' (SEQ ID NO:1) was designed to anneal at the selected allele discriminating SNP (G at the position complementary to base 23 of the IKBA gene in SEQ ID NO:2). The last base at the 3'end of this primer corresponds to the desired allele (C). The reverse primer 5'-CAGTAATACGACTCACTATAAGG-GAGAAGGCTTTCACAAAAGCAACAA AATGAGGGC-3' (SEQ ID NO: 3; which corresponds to a T7 tag-an 8 bp spacer-primer) was designed to anneal to the opposite strand so that 201 bp of the IKBA locus was amplified and a T7 tag was incorporated at one end.

The NEER oligonucleotide competitor 5'-GGC-CAGCGTCTGACGTTATGAG ⊥-3'(SEQ ID NO: 4; with an inverted T base as the 3' most nucleotide) was designed to completely match the non-desired allele (A at the position complementary to base 23 of the IKBA amplicon in SEQ ID NO:2). Additionally, the NEER competitor was non-extendable and exonuclease resistant due to the inverted base (⊥) at the 3' end of the primer corresponding to basepair 23 of the IKBA amplicon. The inverted T base corresponds to a reverse linked nucleotide having an internal 3'-3' linkage therein (as opposed to the natural 5'-3' linkage) that imparts nuclease resistance to a particular oligonucleotide to which it is reverse linked.

The PCR reaction was run under the following conditions.

| 94° C. | 10 min |
|---|---|
| Forty-five cycles of: | |
| 94° C. | 20 sec |
| 64° C. | 30 sec |
| 72° C. | 30 sec |
| Followed by: | |
| 72° C. | 3 min |
| 4° C. | hold |

TABLE 1

Composition of NEER-ASPCR reaction

| Reagents | Final reaction concentration |
|---|---|
| water (HPLC grade) | N/A |
| 10x HotStar Taq PCR buffer containing 15 mM $MgCl_2$ (QIAGEN) | 1x/1.5 mM $MgCl_2$ |
| dNTP mix (GIBCO), 25 mM each | 200 µM each |
| Enzyme HotStar Taq Polymerase (5 U/uL from Qiagen) | 0.2 U/5 µl rxn |
| *Forward and Reverse PCR Primer mix, 1 uM each primer | 200 nM |
| **NEER oligonucleotide | 1 to 4 µM |
| genomic DNA 2.5 ng/uL | 2.5 ng/rxn |

Base-Specific Fragmentation Analysis of NEER-ASPCR Reactions.

A. SAP Treatment:

In this step, the remaining residual dNTPs from the PCR reaction described above in Example 1 are dephosphorylated (deactivated) to ensure that no residual dNTPs from the PCR amplification reaction will be incorporated during subsequent transcription using R&DNA Polymerase (Epicentre; Madison, Wis.).

A master mix of 0.3 µl of shrimp alkaline phosphatase (SAP; 1 U/µl; Amersham-Pharmacia) and 1.7 µl of 1×PCR buffer (Qiagen, Valencia, Calif.; contains 1.5 mM $MgCL_2$, Tris-Cl, KCl, $NH_4SO_4$, pH 8.7, 20° C.) per reaction was made for the total number of samples to be treated. Two microliters of the mixture were added to each well of the microtiter plate containing a PCR reaction (approximately 4 µl volume). The microtiter plate was sealed with Microseal A (ABgene; Rochester, N.Y.) and then subjected to a cycle at 37° C. for 20 minutes, followed by 85° C. for 5 minutes and stored at 4° C.

B. Transcription Reaction:

For each transcription reaction, 2 µl of the SAP-treated PCR sample was mixed with 2 µl of transcription cocktail. Two transcription cocktails were prepared. The dTTP cocktail contained dTTP, rATP, rGTP and rCTP. The dCTP cocktail contained dCTP, rATP, rGTP and rUTP. The nucleotide concentration was 1 mM of each rNTP (Roche Diagnostic Corp, Indianapolis, Ind.) and 2.5 mM of the dNTP (Amersham; Piscataway, N.J.). Each transcription cocktail also contained: 40 mM Tris-acetate, pH 8.0, 40 mM potassium-acetate, 10 mM magnesium-acetate and 8 mM spermidine (Used at a 1:5 final dilution of a 5× stock buffer from Epicentre Madison, Wis.), 5 mM dithiothreitol (DTT; Epicentre; Madison, Wis.), and 20 Units of T7 R&DNA polymerase (Epicentre). The water used was RNAse-free (Sigma Aldrich, St. Louis, Mo.).

To complete the transcription reaction on a new microtiter plate, 2 µl of either the dCTP cocktail or the dTTP cocktail was added along with 2 µl of SAP treated PCR sample per well. The plate was sealed with Microseal A (ABgene; Rochester, N.Y.) and incubated at 37° C. for 2 hours in a thermocycler. It was then stored at 4° C.

The size of the transcript was confirmed by running 1 µl of each transcription reaction sample on a 2% agarose gel. The dCTP and the dTTP cocktail reactions gave the expected size product.

C. Base-Specific RNase A Cleavage

To achieve base-specific fragmentation, an RNase A cocktail was prepared by mixing RNase A powder (Roche Diagnostics Corp.; Indianapolis, Ind.) in RNase free water (SIGMA-ALDRICH) to a concentration of 10 mg/ml. The solution was stored at 4° C. until use. To each well of the microtiter plate containing a transcription reaction (as described above), 2.5 µl of the RNase A mix was added. The RNase reaction was incubated at 37° C. for 1 hour and then reaction products were stored at 4° C.

D. Sample Preparation

To prepare the samples for MALDI-TOF analysis, 20.0 µl of ddH2O was added to each sample within the 384-well plate. 2×3 mg of cation exchange resin X12 (Spectro-CLEAN™; Sequenom; San Diego, Calif.) was added to each well using the resin-dispenser and rotated for 5 min. Samples were then frozen at −20° C. overnight. The next morning, the samples were spun down for 5 minutes at 640×g (2000 rpm, centrifuge IEC Centra CL3R, rotor CAT.244). The samples were then transferred onto a SpectroChip™ array chip (Sequenom; San Diego, Calif.) for MALDI-TOF analysis by robotically dispensing 16 nl of each sample onto the silicon chip. The entire SpectroChip™ array chip was transferred into a Bruker/Sequenom mass spectrometer, which allowed automated measurement of the samples. Positive ions were analyzed and ~50 single shot spectra were accumulated. All samples were analyzed in linear time-of-flight mode using delayed ion extraction and a total acceleration voltage of 20 kV.

NEER-AS-PCR Haplotyping

A 220 bp region from the IKBA gene locus was amplified using NEER-AS-PCR reaction conditions as set forth above. Reactions were performed with the AS-PCR forward primers and NEER competitors, with a 5×-20× excess of NEER competitor as shown in Table 2. Reaction numbers 5-8, corresponding to SEQ ID NOS:8-9 have mismatches at the penultimate base of the forward primers.

TABLE 2

| Reaction No. | AS-PCR forward primer 3' end | NEER competitor |
|---|---|---|
| 1 | C (SEQ ID NO: 1) | none |
| 2 | C (SEQ ID NO: 1) | invT (SEQ ID NO: 4) |
| 3 | T (SEQ ID NO: 6) | none |
| 4 | T (SEQ ID NO: 6) | ddC (SEQ ID NO: 7) |
| 5 | AC (SEQ ID NO: 8) | none |
| 6 | AC (SEQ ID NO: 8) | invT (SEQ ID NO: 4) |
| 7 | AT (SEQ ID NO: 9) | none |
| 8 | AT (SEQ ID NO: 9) | ddC (SEQ ID NO: 7) |

Following NEER-ASPCR reactions, samples were analyzed by base-specific fragmentation analysis as described above. The MALDI-TOF spectra were analyzed using SpectroCLEAVE™ version 5.4.4 software for determination of the polymorphic base at position 147. SpectroCLEAVE™ version 5.4.4 software performs functions similar to those of the SNP Discovery portion of the MassARRAY™ Discovery software, and analyzes mass spectra according to the methods and algorithms provided herein. For example, for reaction #6 from Table 2, a 220 bp amplicon from the IKBA gene locus was amplified using a forward Allele-C specific primer ending with a penultimate mismatch (AC), and a NEER competitor oligonucleotide having an inverted T base at the end. The reverse PCR primer contained the T7 polymerase sequence. Transcription of the amplified amplicon was conducted using a "dCTP cocktail" having dCTP, rATP, rTTP and rGTP. RNAse A fragmentation of this 220 bp amplicon produced a fragment of 3923 Da, suggesting the presence of a compomer C6G3T2 (potential G allele at position 147). In addition, it was found that the three expected peaks indicating the presence of the A-allele were missing, which confirms the presence of the G allele exclusively and specifically (i.e., no allele leakage detected).

The spectra produced either a clear homozygous call (denoted by a "+" in the homo call column of Tables 3 and 4) or an ambiguous call where the spectra indicated the presence of both alleles, due to the leakage of the AS-PCR reaction (indicated by a "−" in the homo call column). N/A in the homo cell column indicates the SNP was not identified under these particular conditions. Eight reference sequence FASTA files were created for comparison with the spectra representing the possible haplotypes based on the various permutations of SNPs at positions 23, 39 and 147 of SEQ ID NO:2. The results of the analysis are shown in Tables 3 and 4 for two of the reference sequences with an A or G at position 147, respectively.

TABLE 3

Reference sequence with an A at position 147

| AS-PCR Primer end | SNP found by SC @ 147 | Homo call |
|---|---|---|
| C | + | − |
| C inv T 20X | + | + |
| T | + | − |
| T ddC 20X | − | NA |
| AC | + | + |
| AC inv T 20X | + | + |
| AT | − | NA |
| AT ddC 20X | − | NA |

TABLE 4

Reference sequence with a G at position 147

| AS-PCR Primer end | SNP found by SC @ 147 | Homo call |
|---|---|---|
| C | + | − |
| C inv T 20X | − | NA |
| T | + | − |
| T ddC 20X | + | + |
| AC | − | NA |
| AC inv T 20X | − | NA |
| AT | + | + |
| AT ddC 20X | + | + |

The results of the analysis indicate that the sample had 2 haplotypes:
1) a T at position 23 with an A at position 147
2) a C at position 23 with a G at position 147

In addition, the NEER-ASPCR achieved results indicated that amplification in the presence of a competitor provides sufficient allele-specificity such that homozygous calls were obtained from a sample that is heterozygous for the SNP at position 147.

Example 2

NEER Competitor Concentration Titration

This example demonstrates the significant effects of NEER competitors in enhancing the specificity of AS-PCR.

A 220 bp amplicon from the IKBA gene locus (SEQ ID NO:2) was PCR amplified in the NEER-ASPCR reaction as described in Example 1 using the NEER oligonucleotide competitor 5'-GGCCAGCGTCTGACGTTATGAG ⊥-3' (SEQ ID NO: 4) in excess concentration to the AS-PCR forward and reverse primers ranging from 7.5 fold (1.5 mM) to 20 fold (4 mM). An hME primer mass extension was performed at an internal SNP, nucleotide 147 of SEQ ID NO:2 previously genotyped as heterozygous for the DNA sample amplified.

Primer Mass Extension Analysis of NEER-ASPCR Reactions

Genotyping of the NEER-allele-specific amplified targets can be carried out using any known method for genotyping, such as either base-specific fragmentation mass spectrometry analysis (e.g., MassCLEAVE™ assay) or primer extension (e.g., MassEXTEND™ reaction). In this example, haplotyping of the IKBA amplicon was carried out using the primer extension assay and MALDI-TOF mass spectrometry analysis.

A. Neutralize Unincorporated dNTPs (SAP Treatment):

Using the NEER-ASPCR reaction products from Example 1, the remaining residual dNTPs from the PCR reaction described above in Example 1 are dephosphorylated (deactivated) to ensure that no residual dNTPs from the PCR amplification reaction will be incorporated during the subsequent primer extension reaction. The SAP enzyme was used to dephosphorylate unincorporated dNTPs from the amplification reaction as follows:

A master mix of 1.53 μl nanopure water, 0.17 μl hME buffer (10×; 260 mM Tris-HCl pH 9.5, and 6 mM MgCl$_2$ and 0.3 μl of shrimp alkaline phosphatase (SAP; 1 U/μl; Amersham-Pharmacia; Piscataway, N.J.) was prepared per sample. For a 384-well plate, the master mix contained 881.3 μl nanopure water, 97.9 μl hME buffer and 172.8 μl SAP. 2 μl of solution master mix was added to each PCR reaction in a 384-well microtiter plate (from Example 1), which produced a final volume of 7 μl. The microtiter plate was sealed with Microseal A (ABgene; Rochester, N.Y.) and then subjected to a cycle at 37° C. for 20 minutes, followed by 85° C. for 5 minutes and stored at 4° C.

B. Primer Extension Reaction (hME also Referred to as MassEXTEND™ Reaction):

The hME assay was designed to detect the sequence of the complementary strand at the polymorphic position, thus the primer extension product incorporated either an A or a G at basepair 147 of the IKBA amplicon (SEQ ID NO:2).

Table 2 lists the hME cocktail components and preparations for single and 384-well microplate reactions.

| Reagent | Stock Concentration | Final Reaction Concentration | Vol. for single reaction | Vol. for microplate |
|---|---|---|---|---|
| nanopure water | N/A | N/A | 1.728 μl | 915.70 μl |
| hME mix (dGTP/ddACT) | 10X hME buffer with 2.25 mM d/ddNTPs | with PCR buffer = 1X buffer with 50 μM d/ddNTPs | 0.200 μl | 105.98 μl |
| hME primer(s) | 100 μM each | 600 nM | 0.054 μl | 28.62 μl |
| hME Enzyme | 32 U/μl | 0.063 U/μl | 0.018 μl | 9.54 μl |
| Total | | | 2 μl | 1059.84 μl |

A master mix for the primer mass extension reactions was made as in Table 2, using ThermoSequenase (SEQUENOM catalog #10052; also available from Amersham Biosciences). The enzyme was kept at −20° C. until it was added to the mix. The template specific hME primer was 5'-ATATCCACACT-GCACACTGCCT-3' (SEQ ID NO: 5), which can hybridize to the strand complementary to SEQ ID NO:2, at nucleotide positions corresponding to 125-146 of SEQ ID NO:2, such that the nucleotide position 147 of SEQ ID NO:2 is the first nucleotide added to the hME primer in a primer extension reaction. The volume of the master mix included about 38% overhang (extra volume) to account for pipetting losses. 2 μl of master mix was added to each well of the microtiter plate containing the SAP-treated reactions. The plate was sealed with Microseal "A" film (MJ Research Inc., S. San Francisco, Calif.).

The reactions were thermocycled as follows:

| 94° C. | 2 min |
|---|---|
| Forty cycles of: | |
| 94° C. | 5 sec |
| 52° C. | 5 sec |
| 72° C. | 5 sec |
| Followed by: | |
| 4° C. | hold |

C. Desalting of the hME Reactions:

16.0 μl of ddH2O was added to each sample within the 384-well plate. Using the SpectroPREP™ multipipettor (Sequenom, San Diego Calif.), 3 mg of cation exchange resin X12 (SpectroCLEAN™ resin; Sequenom; San Diego, Calif.) was added to each well and rotated for 5 min. Samples were then frozen at −20° C. overnight. The next morning, the samples were spun down for 5 minutes at 640×g (2000 rpm, centrifuge IEC Centra CL3R, rotor CAT.244).

D. MALDI-TOF Analysis:

The samples were transferred onto a 384-well SpectroChip® array chip (Sequenom; San Diego, Calif.) for MALDI-TOF analysis using a nanodispenser to robotically dispensing approximately 16 nl of each sample onto the SpectroChip® array chip. The entire SpectroChip® array chip was transferred into a Bruker/Sequenom mass spectrometer, which allowed automated measurement of the samples. Positive ions were analyzed and ~100 single shot spectra were accumulated (e.g., 5 raster positions×20 shots/position). All samples were analyzed in linear time-of-flight mode using delayed ion extraction and a total acceleration voltage of 20 kV. See the "Dispensing Primer Mass Extension Reaction Products onto SpectroCHIPs" chapter in MassARRAY™ *Nanodispenser User's Guide* available from Sequenom (San Diego, Calif.) for instructions.

The mass of the primer used in the primer mass extension reaction was 5668.7 daltons. The allelic variant at nucleotide 147 of SEQ ID NO:2 resulted in the addition of ddATP to the primer to produce an extension product having a mass of 5965.9 daltons, or the addition of a dGTP and a ddATP to the primer having a mass of 6600.3 daltons.

The results from titration experiments indicate that the use of 10- to 20-fold excess of NEER competitor to the concentration of AS-PCR primers was suitable for SNP detection. Typically, for reactions using 200 mM of each PCR primer, 2-4 μM of NEER competitor produced allele-specificity greater than 75% up to about 98% or higher. Results were similar when 45 cycles and 50 cycles were performed.

Example 3

Haplotyping at a 2 Kilobase Locus

This Example demonstrates manipulation of the SNP Discovery Program to permit haplotyping.

A 1998 bp amplicon from the CEPT gene locus (SEQ ID NO:10) was PCR amplified in the NEER-ASPCR reaction as described in Example 1. The primers used for the NEER-AS-PCR reactions are shown in Table 6. The amplicon corresponds to the CEPT gene locus on chromosome 16 q13, position 5'-47292387-47290390-3' on the minus strand.

TABLE 6

| Primer Sequence | | SEQ ID NO: |
|---|---|---|
| AS-PCR primer | 5'-AAGAGCGGAGCTCTCCGAGTGA-3' | 11 |
| | 5'-CAGTAATACGACTCAGTATAGG-GAGAAGGCTAAGAGCGGAGCTCTCCGAGTGA-3' | 13 |
| | 5'-AAGAGCGGAGCTCTCCGAGTGC3' | 12 |
| | 5'-CAGTAATAGGACTCACTATAGGGAGA AGGCTAAGAGCGGAGCTCTCCGAGTGC-3' | 14 |
| Competitor primers | 5'-AAGAGCGGAGCTCTCCGAGTG[invA]-3' | 15 |
| | 5'-AAGAGCGGAGCTCTCCGAGTG[3ddC]-3' | 16 |
| 3' primers | 5'-CAGTAATACGACTCACTATAGGGAGAA-GGGTAGCTGGAGATTTGAGGATGGCAGG-3' | 17 |
| | 5'-AGCTGGAGATTTGAGGATGGCAGG-3' | 18 |

In the reactions a T7 promoter tag was present on either the 5' or 3' end primer. Primers SEQ ID NOS: 13, 14, and 18 contain the T7 tag 5'-CAGTAATACGACTCACTATAGGG-3' (SEQ ID NO:19) as the first 23 nucleotides at the 5' end of the primer. Alternatively, an SP6 tag can be used 5'-CGATT-TAGGAGACACTATAGAAGAG-3' (SEQ ID NO:20) in place of the T7 tag along with a mutant SP6 RNA polymerase that can incorporate a ddNTP.

The PCR reaction was run under the following conditions.

| 94° C. | 10 min |
|---|---|
| Fifty cycles of: | |
| 94° C. | 20 sec |
| 60° C. | 30 sec |
| 72° C. | 3 min |
| 72° C. | 3 min |
| Followed by: | |
| 4° C. | hold |

Following the NEER-AS-PCR reaction, samples were prepared and analyzed by base-specific fragmentation mass spectrometry reactions as described above in Example 1, except that 4 base-specific fragmentation reactions were conducted corresponding the T-specific or C-specific cleavage on the forward and reverse PCR products.

Base-Specific Fragmentation Mass Spectrometry Analysis of NEER-ASPCR Reactions

A. Neutralize Unincorporated dNTPs (SAP Treatment):

In this step, the remaining residual dNTPs from the PCR reaction are dephosphorylated (deactivated) to ensure that no residual dNTPs from the PCR amplification reaction will be incorporated during subsequent transcription using R&DNA Polymerase (Epicentre; Madison, Wis.).

A master mix of 0.3 µl of shrimp alkaline phosphatase (SAP; 1 U/µl; Amersham-Pharmacia) and 1.7 µl of 1×PCR buffer (Qiagen, Valencia, Calif.; contains 1.5 mM MgCL$_2$, Tris-Cl, KCl, NH$_4$SO$_4$, pH 8.7, 20° C.) per reaction was made for the total number of samples to be treated. Two microliters of the mixture were added to each well of the microtiter plate containing a PCR reaction (approximately 4 µl volume). The microtiter plate was sealed with Microseal A (ABgene; Rochester, N.Y.) and then subjected to a cycle at 37° C. for 20 minutes, followed by 85° C. for 5 minutes and stored at 4° C.

B. Transcription Reaction:

Four separate transcription and cleavage reactions were conducted. A T-specific cleavage reaction and a C-specific cleavage reaction was conducted on each of the forward and the reverse amplification products. For each transcription reaction, 2 µl of the SAP-treated PCR sample was mixed with 2 µl of transcription cocktail. Two transcription cocktails were prepared. The dTTP cocktail contained dTTP, rATP, rGTP and rCTP. The dCTP cocktail contained dCTP, rATP, rGTP and rUTP. The nucleotide concentration was 1 mM of each rNTP (Roche Diagnostic Corp, Indianapolis, Ind.) and 2.5 mM of the dNTP (Amersham; Piscataway, N.J.). Each transcription cocktail contained: 40 mM Tris-acetate, pH 8.0, 40 mM potassium-acetate, 10 mM magnesium-acetate and 8 mM spermidine (Used a 1:5 final dilution of a 5× stock buffer from Epicentre Madison, Wis.), 5 mM dithiothreitol (DTT; Epicentre; Madison, Wis.), and 20 Units of T7 R&DNA polymerase (Epicentre). The water used was RNAse-free (Sigma Aldrich, St. Louis, Mo.).

To complete the transcription reaction for subsequent base-specific fragmentation analysis on a new microtiter plate, 2 µl of either the dCTP cocktail or the dTTP cocktail was added along with 2 µl of SAP treated PCR sample per well. The plate was sealed with Microseal A (ABgene; Rochester, N.Y.) and incubated at 37° C. for 2 hours in a thermocycler. It was then stored at 4° C.

The size of the transcript was confirmed by running 1 µl of each transcription reaction sample on a 2% agarose gel. The dCTP and the dTTP cocktail reactions gave the expected size product.

C. Base-Specific RNase A Cleavage:

To achieve base-specific fragmentation, an RNase A cocktail was prepared by mixing RNase A powder (Roche Diagnostics Corp.; Indianapolis, Ind.) in RNase free water (SIGMA-ALDRICH) to a concentration of 10 mg/ml. The solution was stored at 4° C. until use. To each well of the microtiter plate containing a transcription reaction (as described above) 2.5 µl of the RNase A mix was added. The RNase reaction was incubated at 37° C. for 1 hour and then reaction products were stored at 4° C.

D. Sample Preparation

To prepare the samples for MALDI-TOF analysis, 20.0 µl of ddH$_2$O was added to each sample within the 384-well plate. 2×3 mg of cation exchange resin X12 (Spectro-CLEAN™ resin; Sequenom; San Diego, Calif.) was added to each well using the resin-dispenser and rotated for 5 min. Samples were then frozen at −20° C. overnight. The next morning, the samples were spun down for 5 minutes at 640×g (2000 rpm, centrifuge IEC Centra CL3R, rotor CAT.244). The samples were then transferred onto a SpectroChip™ array chip (Sequenom; San Diego, Calif.) for MALDI-TOF analysis by robotically dispensing 16 nl of each sample onto the silicon chip. The entire SpectroChip™ array chip was transferred into a Bruker/Sequenom mass spectrometer, which allowed automated measurement of the samples. Positive ions were analyzed and ~50 single shot spectra were accumulated. All samples were analyzed in linear time-of-flight mode using delayed ion extraction and a total acceleration voltage of 20 kV.

NEER-AS-PCR Haplotyping

The protocol below describes the use of the MassAR-RAY™ Discovery software for SNP analysis, as set forth in the MassARRAY™ Discovery-RT Software Users Guide (version 1.1), that is available from Sequenom (San Diego, Calif.); this software analyzes mass spectra according to the methods and algorithms provided herein. Those of skill in the art will recognize that other programs and systems that utilize the algorithms provided herein can be used for the SNP haplotyping analysis described herein. The results of this analysis are shown below in Table 7.

MassARRAY™ Discovery Plate Editor

The MassARRAY™ Discovery Plate Editor (Plate Editor) is used to specify the layout and content of the plates before the SNP analysis run. Before the Plate Editor can be used, amplicons and samples must be entered into the MassARRAY™ SNP Discovery database.
1. On the Windows desktop, double-click the MassARRAY™ Discovery-RT folder to open it.
2. Double-click the SNP Discovery shortcut. The Discovery-RT Client window appears.
3. Click Plate Editor. The Connect Dialog dialog box appears.
4. Type your user name, password, and a data set name. Then, click OK.

Before samples can be selected for use on a plate, the labels or identifiers for those samples must first be added to the SNP Discovery database. Sample labels (identifiers) can be added one at a time manually, or can be imported from a text file.

Adding Sample Labels Manually
1. In the Plate Editor, choose Import Samples on the File menu. The Edit Sample Dialog dialog box appears.
2. Click a project to open it.
3. Right-click a project row under the Customer/Project column, and choose Add Empty Sample. A New Samples row appears.
4. Double-click in the New Samples box, and then type the name of the new sample.
5. Click OK.

Importing Amplicons (Reference Sequences)

A text file can be created that lists data for one or many amplicons, which allows for fast import of multiple amplicons into the Plate Editor. Bring amplicons into the SNP Discovery database by importing FASTA files (.fasta) or tab-delimited text files formatted in FASTA format (.txt). Create the import file using either Microsoft Notepad or Microsoft Excel. Files created in either application must contain the same information, but the syntax and formatting are different for each application.

Files Created in Microsoft Notepad

Amplicon import files created in Notepad must be properly formatted as follows:

>amplicon name || description [left primer length, right primer length] sequence In the syntax listed above, notice there are no spaces between the name of amplicon and the double bar or between the double bar and description text. Likewise, there is a comma but no space separating the left primer length and right primer length.

To Import Amplicons
1. In the Plate Editor, choose Import Amplicons on the File menu. The Edit Amplicon Dialog dialog box appears.
2. Right-click a row under the Customer/Project column, and choose Import Amplicons From Fasta File (if the file was created in Notepad) or Import Amplicons from Tab Delimited File (if the file was created in Excel). An Open dialog box appears.
3. Select a fasta or .txt file, and then click Open. By default, only FASTA files (.fasta) are displayed in the Open dialog box. To view text files (.txt), choose (.txt) from the File Type drop-down list. The selected file is imported into the database. The sequence contained in the file is listed under the currently selected project.
4. To edit any information in the imported amplicon file, double-click the appropriate box and type new information.
5. If any of the amplicons just imported are to be deleted, it must occur now.
6. Click OK to close the Edit Amplicons Dialog dialog box.

Creating a New Plate

Selecting an Assay

Each plate defined must include an assay. The composite assay informs the Discovery Analysis software as to which cleavage occurs in which plate position to correlate to each of the four reactions.
1. Click the Reaction tab.
2. Right-click a row under the Reaction column, and choose Load Composite Assay from DB. The Select a Composite Assay dialog box appears.
3. Select the Standard Cleavage Scheme assay, and then click OK.

The Reaction tab and plate layout are populated with the assay selected.

Adding Amplicons
1. Click the Amplicon tab.
2. Right-click a row under the Description column, and choose one of the following menu options:
   Replace Amplicons to replace one or more amplicons in the Description list.
   Append Amplicons to add one or more amplicons to the Description list. The Select Amplicons dialog box appears.
3. Double-click a project. The amplicons contained in that project are listed under Available Amplicons.
4. Select one or more amplicons, and then click the Move arrow.
5. Or, click Move All to move all of the amplicons under Available Amplicons into the Selected Amplicons box.
6. Click Import if amplicons are to be imported into the database. The Edit Amplicon Dialog dialog box appears. Once imported, the amplicons will be available for selection in the Select Amplicons dialog box.
7. Once amplicons have been selected, click Up and Down to move them into the correct order. The order in which the amplicons are listed in the Selected Amplicons box is the order in which they will be loaded into the Amplicon tab.
8. Click OK. The Amplicon tab and plate layout are populated with the selected amplicons.

Adding Samples
1. Click the Samples tab.
2. Right-click a row under the Sample column, and choose one of the following menu options:
   Replace Samples to replace one or more samples in the Samples list.
   Append Samples to add one or more samples to the Samples list. The Select Project dialog box appears.
3. Select a project, and then click OK. The Select Samples dialog box appears.
4. Double-click a project. A list of available samples appears under Available Samples.
5. Select one or more samples, and then click the Move arrow.
6. Or, click Move All to move all of the amplicons under Available Samples into the Selected Samples box.
7. Click Import if samples are to be imported into the database. The Edit Sample Dialog dialog box appears. Once imported, the samples will be available for selection in the Select Samples dialog box.
8. Once all the samples you want have been selected, click Up and Down to move them into the correct order. The order in which they are listed in the Selected Samples box is the order in which they will be loaded into the Samples tab.
9. Click OK. The Samples tab and plate layout are populated with the selected samples.

Saving Plates

After a plate has been defined (specify its layout and add reactions, amplicons, and samples), it should be saved to the SNP Discovery database.
1. On the File menu, choose Save. The Select Project dialog box appears.
2. Select a location for the plate, and type a name for the plate in the Composite Plate box.
3. Click OK. The plate is saved to the database.

Acquiring Spectra

ACQUIRE controls the MassARRAY™ Genotype Analyzer biflex mass spectrometer (genotype analyzer) to acquire spectra from SpectroCHIP array chips.

As each SpectroCHIP array chip is processed by the genotype analyzer mass spectrometer, the spectral data is automatically processed and saved to the MassARRAY™ SNP Discovery database.
1. On the MassARRAY™ Discovery RT workstation, start ACQUIRE and CALLER for Discovery.
2. On the Sun workstation, select a geometry file in the XACQ software.
3. On the Sun workstation, load the MassCLEAVE™ assay parameter file.
4. On the MassARRAY™ Discovery RT workstation, start Plate Editor and export plates.
5. On the Sun workstation, load SpectroCHIP array chips.
6. On the Sun workstation, set SpectroCHIP array chip geometry options.
7. On the MassARRAY™ Discovery RT workstation, start the automatic run.

Validating SNPs

Follow these instructions for all SNPs marked Auto Sel, Evaluate, Auto Sel*, or Auto Keep.
1. Run analysis of plate in Discovery-RT Client/Analyzer.
2. On the SNP Statistics tab, Right-click SNP #1, and select Annotate Sequence Variation to display graph labels on sequence variation peaks. For the selected SNP, the spectrum graph now marks the sequence variation peaks and lists their masses.
3. Right-click SNP #1 and select Display Sequence Variation to display its sequence variation. The View Sequence Variation dialog box appears.
4. In the View Sequence Variation dialog box, locate a signal pair that can support SNP #1. Ideally, a signal pair should contain two signals with a small mass shift, where both signals come from the same fragment. (In certain instances, it can not be possible to locate a signal pair with a small mass shift.) When selecting a signal pair during SNP validation, be sure the pair contains at least one confirming signal or at least one missing signal that is ranked "Homozygous Supporting" (shown in the Judgement column on the SNP Statistics tab). When selecting a signal pair, avoid selecting a signal that is marked (silent) in the View Sequence Variation dialog box.
5. On the SNP Statistics tab, click the confirming signal contained in the signal pair you chose from the Sequence Variations list.
6. Click the Display tab. The sample containing the confirming signal is automatically selected and its spectrum displayed.
7. Using the arrow keys on the keyboard, scroll through the samples and compare SNP samples listed to the samples of the other allele. For samples containing the SNP being evaluated, compare the peaks for the signal pair to determine if it supports the SNP. This step can be omitted for known SNP, in such a case go to 8.
8. If the spectra analyzed in Step 7 display signal pair peaks indicating that each signal in the pair corresponds well to the other, then it is a good supporting signal pair for the SNP. The SNP is valid. Do the following:
   For SNPs that are valid, click inside the Iterative box for the SNP, and then choose Man Sel from the drop-down list. The SNP is considered valid, and it remains in the SNP list.
9. If the spectra analyzed in Step 7 display signal pair peaks where each signal in the pair acts independently of the other for all samples, then the signal pair can not be supporting a valid SNP. Do the following:
   Repeat this process using a different signal pair. (Review the Sequence Variations list to choose a different signal pair.)
   For SNPs that are not valid, click inside the Iterative box for the SNP, and then choose Evaluate, Discard or Discard All from the drop-down list. The SNP is removed from the SNP list. (If you chose Discard All, the SNP and any related SNP candidates are removed from the list.) Continue validating the rest of the SNPs listed on the SNP Statistics tab once either of the following is determined:
   SNP #1 is a valid SNP.
   SNP #1 is not a valid SNP, but a subsequent SNP is valid.

Sequence Read

The Sequence Read tab provides an overview of the alleles for selected SNPs in all samples. Only those SNPs marked as Auto Sel, Auto Sel*, Auto Keep, Man Sel, or Man Keep in the Iterative column on the SNP Statistics tab are listed on the Sequence Read tab. SNPs are listed across the tab in order of their position in the sequence. If spectrum quality is sub par, adjustments can be made to the "Unknown Sum Weight Threshold" under "Sequence Parameters" found in the Analysis Params Tab to display all selected SNPs.

TABLE 7

Results of CETP haplotype analysis

| SNP ID | Position in SEQ ID NO: 10 | Chromosomal position | Sample Genotype | C Allele Haplotype | A Allele Haplotype |
|---|---|---|---|---|---|
| 158478 | 22 | 47292365 | CA | C | A |
| 158479 | 336 | 47292051 | GA | BLD | BLD |
| 158480 | 515 | 47291872 | GA | A | G |
| 158617 | 575 | 47291872 | AG | G | A |
| 289715 | 796 | 47291591 | ND | BLD | BLD |
| 230789 | 1483 | 47290904 | ND | BLD | BLD |
| 289716 | 1664 | 47290723 | TA | A | T |
| 289717 | 1676 | 47290711 | GA | A | G |
| Novel Deletion | 1940 | 47290441–47290447 | CdelC | delC | C |

ND: Not determined
BLD: Below detection limit

The 5 SNPs detected by the program were reported as homozygous as expected for a successful allele-specific amplification. The two 6-SNP haplotypes were assigned non-ambiguously as:

C-allele haplotype=CAGAAdeIC; and
A-allele haplotype=AGATGC.

Since modifications will be apparent to those of skill in this art, it is intended that this invention be limited only by the scope of the appended claims.

What is claimed is:

1. A method for haplotyping a plurality of polymorphic markers, comprising:
    a) amplifying a target DNA molecule, using two primers, wherein one of the primers is allele-specific, and wherein at least one of the primers comprises an RNA promoter in the presence of
        i. a competitor oligonucleotide comprising a modified 3'-end nucleotide selected from an inverted base, a dideoxynucleotide bound to the penultimate nucleotide by a methylphosphonate link, a ribonucleotide, a 3' Phosphate, a carbon chain spacer, or a peptide nucleic acid (PNA), wherein the competitor is an extension inhibitor of an unwanted allele, and
        ii. a mixture of thermostable DNA polymerases, wherein at least one of the polymerases comprises 3'-5' exonuclease activity, and
    obtaining a double stranded DNA molecule;
    b) fragmenting the double stranded DNA molecule, or an RNA product transcribed from the double stranded DNA molecule, at a plurality of specific and predictable sites;
    c) fragmenting or simulating fragmentation of a reference nucleic acid into fragments at the same plurality of specific and predictable sites of step b);
    d) comparing the fragments of step b) with the fragments or simulated fragments of step c); and
    e) from the comparison of fragments of d), haplotyping a plurality of linked SNPs on the target DNA molecule corresponding to a single or specific allele at one or more loci, in a single reaction.

2. The method of claim 1, comprising detecting a previously undiscovered SNP within the haplotype.

3. The method of claim 1, comprising haplotyping three or more linked SNPs on the target DNA molecule.

4. The method of claim 1, comprising haplotyping four or more linked SNPs on the target molecule.

5. The method of claim 1, comprising haplotyping two or more linked SNPs on the same gene.

6. The method of claim 1, comprising haplotyping three or more linked SNPs on the same gene.

7. The method of claim 1, wherein the target DNA is not amplified before step a).

8. The method of claim 1, wherein the amplification step is PCR amplification from a diluted DNA sample containing an amount of haploid genome equivalents selected from 10, 9, 8, 7, 6, 5, 4, 3, 2 or 1.

9. The method of claim 1, wherein the competitor oligonucleotide is added to the amplification reaction in an excess amount over a concentration of an Allele-Specific PCR amplification primer selected from among: 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold or 75-fold or more.

10. The method of claim 1, wherein the target DNA molecule corresponding to a single or specific allele is present in less than 10% of the nucleic acid present in a sample mixture.

11. The method of claim 1, wherein the target DNA molecule corresponding to a single or specific allele is present in less than 5% of the nucleic acid present in a sample mixture.

12. The method of claim 1, wherein both oligonucleotide primers comprise RNA promoter sequences.

13. The method of claim 1, wherein the haplotyping step comprises:
    f) determining mass signals of the fragments produced in b) and c);
    g) determining differences in the mass signals between the fragments produced in a) and the fragments produced in b); and
    h) determining a reduced set of sequence variation candidates from the differences in the mass signals and thereby determining sequence variations in the target DNA molecule compared to the reference nucleic acid.

14. The method of claim 13, wherein determining sequence variations comprises:
    i) identifying fragments that are different between the target DNA molecule and the reference nucleic acid;
    j) determining compomers corresponding to the identified different fragments in step h) that are compomer witnesses; and
    k) determining a reduced set of sequence variations corresponding to the compomer witnesses that are candidate sequences to determine the sequence variations in the target DNA molecule compared to the reference nucleic acid.

15. The method of claim 1, wherein the haplotyping step comprises mass spectrometric analysis.

16. The method of claim 1, wherein the mixture of thermostable DNA polymerases is selected from the group consisting of Taq/Pfu, Taq/Deep Vent, Taq/Vent, Taq/Pwo, Taq/Tgo, Klentaq1/Pfu, Klentaq1/Deep Vent, Klentaq1/Vent/Klentaq1/Pwo, and Klentaq1/Tgo.

17. The method of claim 1, wherein the amplified double stranded DNA molecule is more than 1 kb.

18. The method of claim 1, wherein the amplified double stranded DNA molecule is more than 2 kb.

19. The method of claim 1, wherein the amplified double stranded DNA molecule is more than 5 kb.

20. The method of claim 1, wherein the modified 3'-end nucleotide is an inverted base.

21. The method of claim 1, wherein the modified 3'-end nucleotide is a ribonucleotide.

22. The method of claim 1, wherein the modified 3'-end nucleotide is a 3' Phosphate.

23. The method of claim 1, wherein the modified 3'-end nucleotide is a carbon chain spacer.

24. The method of claim 1, wherein the modified 3'-end nucleotide is a peptide nucleic acid (PNA).

25. The method of claim 23, wherein the carbon chain spacer is selected from the group consisting of C-3, C-5, C-7, C-9 and C-12.

26. The method of claim 1, wherein the modified 3'-end nucleotide is a dideoxynucleotide bound to the penultimate nucleotide by a methylphosphonate link.

* * * * *